(12) United States Patent
Israelsson

(10) Patent No.: US 8,609,393 B2
(45) Date of Patent: Dec. 17, 2013

(54) FLUORESCENT PROTEINS AND GENES ENCODING THEM

(75) Inventor: Olle Israelsson, Solna (SE)

(73) Assignee: Innoventus Project AB, Uppsala (SE)

( * ) Notice: Subject to any disclaimer, the term of this patent is extended or adjusted under 35 U.S.C. 154(b) by 846 days.

(21) Appl. No.: 12/308,048

(22) PCT Filed: Jun. 8, 2007

(86) PCT No.: PCT/SE2007/000551
§ 371 (c)(1),
(2), (4) Date: Dec. 5, 2008

(87) PCT Pub. No.: WO2007/142582
PCT Pub. Date: Dec. 13, 2007

(65) Prior Publication Data
US 2009/0286314 A1 Nov. 19, 2009

Related U.S. Application Data

(60) Provisional application No. 60/811,769, filed on Jun. 8, 2006.

(30) Foreign Application Priority Data

Jun. 8, 2006 (SE) ...................................... 0601261

(51) Int. Cl.
*C07H 21/04* (2006.01)
*C07K 1/00* (2006.01)
*C12N 15/00* (2006.01)
*C12N 1/20* (2006.01)

(52) U.S. Cl.
USPC .................... 435/252.3; 530/350; 435/320.1; 536/23.2

(58) Field of Classification Search
None
See application file for complete search history.

(56) References Cited

FOREIGN PATENT DOCUMENTS

| WO | 2004/058973 A1 | 7/2004 |
| WO | 2008/094316 A2 | 8/2008 |

OTHER PUBLICATIONS

Branden et al. Introduction to Protein Structure, Garland Publishing Inc., New York, p. 247, 1991.*
Y.J. Passamaneck, et al."Live Imaging of Fluorescent Proteins in Chordate Embryos: From Ascidians to Mice", Microscopy Research and Technique, 2006, vol. 69, pp. 160-167.
Deheyn, D. et al.: "Optical, biochemical, and molecular characterization of new bioluminescence systems," May 9, 2007, Financial Performance Report, Program: AFOSR, Biomimetics, Biomaterials, and Biointerfacial Sciences, XP-002544859, [Retrieved from the Internet, Sep. 9, 2009].
Deheyn, D et al.: "Endogenous Fluorescent Protein (GFP) in Amphioxus," The Biological Bulletin Oct. 2007, Marine Biological Laboratory, vol. 213, No. 2, pp. 95-100, XP-002544858.
Baumann Diana et al: "A family of GFP-like proteins with different spectral properties in lancelet Branchiostoma floridae," Biology Direct, Bio Central Ltd, Lo. vol. 3, No. 1, Jul. 3, 2008, p. 28, XP-021039095.
Bomati Erin K. et al.: "Amphioxus encodes the largest known family of green fluorescent proteins, which have diversified into distinct functional classes," BMC Evolutionary Biology, Biomed Central Ltd., London, GB, vol. 9, No. 1, Apr. 21, 2009, p. 77, XP-021047763.
Li G. et al.: "Evolutionary and functional diversity of green fluorescent proteins in cephalochordates," Gene, Elservier, Amsterdam, NL, vol. 446, No. 1. Oct. 1, 2009, pp. 41-49, XP-026446254.
European Office Action issued in corresponding Application 07 748 214.9, dated Feb. 28, 2012.
Supplemental European Search Report issued in corresponding Application 07 74 8214, Sep. 9, 2009.

* cited by examiner

*Primary Examiner* — Yong Pak
(74) *Attorney, Agent, or Firm* — Bacon & Thomas, PLLC

(57) ABSTRACT

Fluorescent proteins comprising the following internal amino acid sequence

```
                                          (SEQ ID NO: 47)
  Gly Tyr Xaa Xaa Xaa Gln Tyr Leu Pro Xaa Pro
  1               5                       10
``` wherein
  Xaa in position 3 is Ala or Gly,
  Xaa in position 4 is Phe, His or Tyr,
  Xaa in position 5 is His, Tyr or Asn, or
  Xaa in position 10 is Phe or Tyr
are disclosed. Such proteins are e.g. isolated or recombinant fluorescent proteins from a Cephalochordata, such as *Branchiostoma floridae* or *Branchiostoma lanceolatum*, or isolated mutants or recombinant proteins that have at least 80% amino acid sequence identity with the fluorescent proteins. Isolated and purified structural genes encoding such fluorescent proteins are also disclosed.

3 Claims, 4 Drawing Sheets

SEQUENCE LISTING

```
<160> NUMBER OF SEQ ID NOS: 93

<210> SEQ ID NO 1
<211> LENGTH: 480
<212> TYPE: DNA
<213> ORGANISM: Branchiostoma floridae

<400> SEQUENCE: 1
atgcctcttc caactaccca cgagttgcac atctttggtt ccttcaatgg tgtggagttt      60
```

```
gacttggtgg gccgtggcga aggtaatcca aaggatgggt ctcagaacct acacctgaag    120
tccaccaagg gtgccctcca gttctcccca tggatgctgg tccctcacat cgggtacggc    180
ttctaccagt acctgcctta cccggacggc gaaatgtcgc cttaccaggc cgccatgtat    240
ggtggctcag ggtacctaat gcatcgcaca atgcaatatg aagacggtgc caagattagt    300
ggccactaca atacaccta cgagggaagc cacgtgaaag gagaatttca gctcattggg      360
accggattcc ctactgacgg tcctgtgatg accaaccagc tcaccgctgc ggactggtgc    420
gtggacaagt tgctgtaccc caacgacaag accattatca gcaagttcga ctggagctac    480
```

<210> SEQ ID NO 2
<211> LENGTH: 678
<212> TYPE: DNA
<213> ORGANISM: Branchiostoma floridae

<400> SEQUENCE: 2

```
atggcttcca tattggtgcc tcttccaaag acccacgagt tgcacatctt tggttccttc     60
aatggtgtta agtttgacat ggttggtgaa ggcaccggta accctaatga ggggtctgag    120
gagctaaaac tgaagtccac caatggtccc ctgaagttct cccctacat cctggtccct     180 cacctcgggt acgctttcaa ccagtacctg cccttccctg acgggatgtc gcctttccag    240
gccgccatgc aggacgaatc gggtatcaa gtgcatcgca cgttgcagta tgaagacggt     300
gccttcgtga ctgctaactt acgctacacc tacgagggaa gtcacatcaa aggggagttc    360
caggtgatcg ggaccggttt tcctcctgat ggtcctgtga tgaccaacaa gctcaccgct    420
ttggactgga gcgtggtcaa gtttgtgtac cccaacgaca gaccatcct cagcactttc     480 gacaaaacct acaccaccac cgatggcaaa cgctaccagt gcacatttcg tgaaaacaac    540
accttcgcca gccgatggc ggccgacatc ctgcagaagc agccgatgtt cattttccat     600
aagacggagc tccagcactc taacaacgcc gagctcacct tcaaggagaa gcagacagcc    660
ttctccgata tgaagtga                                                   678
```

<210> SEQ ID NO 3
<211> LENGTH: 479
<212> TYPE: DNA
<213> ORGANISM: Branchiostoma floridae

<400> SEQUENCE: 3

```
atgtctctgc ctacggccca tgactgccac atgttcggct ccatcaacgg ccacgagttt     60
gacctggtgg gcggtggaaa cgggaacccg aatgacggga cactggagac caaggtgcgc    120
tccaccaagg gtgccctgcc cttctcccc gtgatcctgg cccctaacct ggggtacggg     180
taccaccagt acctgccctt cccggccggg acctcaccgt accagcaggc catcaccaac    240
ggagtgtacc aaaagcaccg caccttcaag ttcgaggacg gcggcgtcat gaccatcaac    300
ttccgctaca cctactcagg gaacaagatc aagggagagt tccacgtact ggttggatcc    360
gggttccctg atgacggccc tgtgaagacc cactcactcc agcagcatga tcataacgtg    420
gagaggctga tggtgctggg agacaagacc atcggcagcg acaacatgtg gactttcac    479
```

<210> SEQ ID NO 4
<211> LENGTH: 473
<212> TYPE: DNA
<213> ORGANISM: Branchiostoma floridae

<400> SEQUENCE: 4

```
tctctgccta cgacccatga ctgccacatg ttcggctcca tcaacggcca cgagtttgac     60
```

```
ctggtgggcg gtggaaacgg gaacccgaat gacgggacgc tggagaccaa ggtgcgctcc    120
accaagggag ccctgccctt ctccccagtg atcctggccc ctaacctggg gtacgggtac    180
caccagtacc tgcccttccc ggccgggacc tcacccctacc agcaggccat caccaacgga    240
gggtaccaaa agcaccgcac gttcaagttc gaggacggcg gcgtcatgac catcaacttc    300
cgctacacct actcagggaa caagatcaag ggagagttcc acgtggttgg atccgggttc    360
ccagatgatg gccctgtgat gaccaactct ctccagcagc acgatcataa cgtggagagg    420
ctgatggtgc tgggagacaa gaccatcggc agcgacaaca tgtggacttt cac           473

<210> SEQ ID NO 5
<211> LENGTH: 672
<212> TYPE: DNA
<213> ORGANISM: Branchiostoma floridae

<400> SEQUENCE: 5
atgcctcttc caaagaccca cgagttgcac atctttggtt ccttcaatgg tgttgagttt     60
gacatggttg ctcgcggcat cggcaaccct aatgaggggt ctgaggaact gaacgcgaag    120
ttcaccaagg gtcccctgaa gttctccccc tacatcctgg tccctcacct cgggtacgct    180
tactaccagt acctgccctt ccctgacggg atgtcgcctt ccaggccgc catgcacgac     240 ggctcgggct atcaagtgca tcgcacgatt cagtatgaag acggtgcctc cgtgactgcc    300
cactaccgct acacctacga gggaagccac atcaagggg agtttcaggt gatcgggacc    360
ggatttcctc ctgacggtcc tgtgatgacc aacaagctca ccgctatgga ctggagcgtg    420
accaagatgc tgtacccgaa cgacaagacc atcctcagca ctgccgactg tagctacacc    480
accaccgagg gcaaacgcta ccagagcaaa atgcgtgaaa acaacacctt cgccaagccg    540
atggcggccg acatcctgca gaagcagccg atgttcgtgt ccgtaagac ggagctccag     600 cactccaaga ccgagctcac cttcaaggag tggcagaaag ccttcaccga tgtgataact    660
ggacatatct aa                                                        672

<210> SEQ ID NO 6
<211> LENGTH: 696
<212> TYPE: DNA
<213> ORGANISM: Branchiostoma floridae

<400> SEQUENCE: 6
atgtctgtcc cgacaaacct cgacttgcac atctacggct ccatcaacgg tatggagttc     60
gacatggtgg gcggtgggag tggcaaccca aaggatggat cgctggccgt aaacgtgaag    120
tccaccaaag gagctctgtg cgtttccccc ctgctggtgg gcccgcatct ggggtacggc    180
cactaccagt acctaccctt ccctgacggc gcgtcgcctt ccaggcagc cgtgaacaac    240 ggcgggtatc aaatgcatcg cagtttcaac ttcgaggacg gggccgtgct gactgccacc    300
tacaactact cctacagcgg cggcaagatc cagggagagt ttcatctggt gggcagcggt    360
ttccccgacg atagtccggt gatgaccaac gcgctgaccg gtctggacag gagcgtgtcc    420
aagctgatgt gcacgtccga tgacaagctc gtcgagtccg tgcactggag ctaccgcacc    480
agcagcggcg ggcgctaccg tgccacggtg cagaccaact tcaccttcgc aaagcccatc    540
gaagctggcc tgaagaacaa catgccgatg ttcgtgttcc gtcagctgga agtcaccggc    600
tccaaaaccg agatcggcct tcaggagcag caaaaggcgt tctccaccgt tctgatgcgt    660
ttatggttga aatgcaaaag agttgaaata ctttga                              696
```

<210> SEQ ID NO 7
<211> LENGTH: 693
<212> TYPE: DNA
<213> ORGANISM: Branchiostoma floridae

<400> SEQUENCE: 7

| | | | | | |
|---|---|---|---|---|---|
| tctgtcccga | caaacctcga | cttgcacatc | tacggctcca | tcaacggtat | ggagttcgac | 60 |
| atggtgggcg | gtggcagtgg | caacccaaag | gatggatcgc | tggccgtaaa | cgtgaagtcc | 120 |
| accaaaggag | cactgcgcgt | tcccccctg | ctggtgggcc | cgcatctggg | gtacggccac | 180 |
| taccagtacc | tacccttccc | cgacggcgcg | tcgccttccc | aggcagccgt | gaacaacggc | 240 |
| gggtatcaaa | tgcatcgcag | tttcaacttc | gaggacgggg | ccgtgctgac | tgccacctac | 300 |
| aactactcct | acagcggcgg | caagatccag | ggagagtttc | atctggtggg | cagcggtttc | 360 |
| cccgacgata | gtccggtgat | gaccaacgcg | ctgaccggtc | tggacaggag | cgtgtccaag | 420 |
| ctgatgtgca | cgtccgatga | caagctcgtc | gagtccgtgc | actggagcta | ccgcaccagc | 480 |
| agcggcgggc | gctaccgtgc | cacggtgcag | accaacttca | ccttcgcaaa | gcccatcgca | 540 |
| gctggcctga | gaacaacat | gccgatgttc | gtgttccgtc | agctggaagt | caccggctcc | 600 |
| aaaaccgaga | tcggccttca | ggagcagcaa | aaggcgttct | ccaccgttct | gatgcgttta | 660 |
| tggttgaaat | gcaaaagagt | tgaaatactt | tga | | | 693 |

<210> SEQ ID NO 8
<211> LENGTH: 699
<212> TYPE: DNA
<213> ORGANISM: Branchiostoma floridae

<400> SEQUENCE: 8

| | | | | | |
|---|---|---|---|---|---|
| atgtctgtcc | cgacaaacct | cgacttgcac | atctacggct | ccatcaacgg | tatggagttt | 60 |
| gacatggtgg | gcggtgggag | tggcaaccca | aatgacggat | cgctgagcgt | aaacgtgaag | 120 |
| tctaccaaag | gtgccctgcg | cgtttctcct | ctgctggtgg | gcccgcatct | ggggtacggc | 180 |
| cactaccagt | acctacccct | ccctgacggt | ccgtcgcctt | ccaggcagc | cgtgaacaac | 240 |
| ggcggatatc | aaatgcatcg | ctcttcaac | ttcgaggacg | tgccgtgct | gactgccacc | 300 |
| tacaactact | cctacagcgg | cggcaagatc | cagggagagt | ttcatgtact | ggtgggcagc | 360 |
| tgtttccccg | acgatagtcc | ggtgatgacc | aacgcgctga | ccggtttgga | caggagcgtg | 420 |
| gccaagctga | tgtgcgtgtc | cgatgacaag | cttgccgagt | tcgtggactg | gacctaccgc | 480 |
| accagcagcg | gcgggcgcta | ccgtgccacg | gtgcagacca | acttcacctt | cgcaaagccc | 540 |
| atcgcagctg | gcctgaagaa | caacatgccg | atgttcgtgt | tccgtcagct | ggaagtcacc | 600 |
| ggctccaaaa | ccgagatcag | ccttcaggag | cagcaaaagg | cgttctccac | cgttctggtg | 660 |
| cgtttatggt | tgaaatgtaa | aagagctgaa | atactttga | | | 699 |

<210> SEQ ID NO 9
<211> LENGTH: 660
<212> TYPE: DNA
<213> ORGANISM: Branchiostoma floridae

<400> SEQUENCE: 9

| | | | | | |
|---|---|---|---|---|---|
| atgcctcttc | caaagaccca | cgagttgcac | atctttggtt | ccttcaatgg | tgttgagttt | 60 |
| gacatggttg | gtcgcggcat | cggcaaccct | aatgaggggt | ctgaggaact | gaacgcgaag | 120 |
| ttcaccaagg | gtccctgaa | gttctcccc | tacatcctgg | tccccacct | cgggtacgct | 180 |
| tactaccagt | acctgcccctt | ccctgacggg | atgtcgcctt | tccaggccgc | catgcacgac | 240 |
| ggctcgggct | atcaagtgca | tcgcacgatt | cagtatgaag | acggtgcctc | cgtgactgcc | 300 |

```
cactaccgct acacctacga gggaagccac atcaaagggg agtttcaggt gatcgggacc    360
ggatttcctc ctgacggtcc tgtgatgacc aacaagctca ccgctatgga ctggagcgtg    420
accaagatgc tgtacccgaa cgacaagacc atcctcagca ctgtcgactg tagctacacc    480
accaccgagg gcaaacgcta ccagagcaaa atgcgtgaaa caacaccctt cgccaagccg    540
atggcggccg acatcctgca gaagcagccg atgttcgtgt tccgtaagac ggagctccag    600
cactccaaga ccgagctcac cttcaaggag tggcagaaag ccttcaccga tgtgatgtga    660
```

<210> SEQ ID NO 10
<211> LENGTH: 663
<212> TYPE: DNA
<213> ORGANISM: Branchiostoma floridae

<400> SEQUENCE: 10

```
atgcctcttc caaagaccca cgagttgcac atctttggtt ccttcaatgg tgttaagttt     60
gacatggttg gtgaaggcac cggtaaccct aatgaggggc tgaggagct aaaactgaag    120 tccaccaatg gtccctgaa gttctccccc tacatcctgg tccctcacct cgggtacgct    180
ttcaaccagt acctgccctt ccctgacggg atgtcgcctt ccaggccgc catgcaggac    240 gaatcggggt accaagtgca tcgcacgttg cagtatgaag acggtgcctt cgtgactgct    300
aacttacgct acacctacga gggaagtcac atcaaagggg agttccaggt gatcgggacc    360
ggttttcctc ctgatggtcc tgtgatgacc aacaagctca ccgctttgga ctggagcgtg    420
gtcaagtttg tgtaccccaa cgacaagacc atcctcagca ctttcgacaa acctacacc    480 accaccgagg gcaaacgcta ccagtgcaca tttcgtgaaa acagcacctt cgccaagccg    540
atggcggccg acatcctgca gaagcagccg atgttcatct tccataagac ggagctccag    600
cactccaaca atgccgagct caccttcaag gagaagcaga cagctttctc cgatatgaag    660
tga                                                                  663
```

<210> SEQ ID NO 11
<211> LENGTH: 669
<212> TYPE: DNA
<213> ORGANISM: Branchiostoma floridae

<400> SEQUENCE: 11

```
cctcttccaa cgactcacga ggtgcacgtc tatggctcta tcaacggtgt tgagtttgac     60
ttggtgggta gcggcaaagg caacccgaag gatggttctg aggagatcca agtgaagtcc    120
actaagggtc ccctcgggtt ctccccgccc gtcgtggtcc ccaacatcgg gtacggcttc    180
caccagtact gcccttccc cgacgggatg tcgccttcc aggccgccgc ggacgatggc    240
tcggggtacg tagtccatcg taatattcag tttgaagacg gcgcctcgct gactggcatc    300
taccgatatt cctacgatgc aggtcacatc aaaggagagt tcgtgtggt tggcagtggt    360 ttccctgctg acggtcctgt gatgaccaaa tcgctcacgg ctgtggactg gagcgtggct    420
accatgctgt cccgaacga caccaccgtt gtctccacca ttgactggac ttgccccact    480
accagcggca aacgctacca cgccacgtg aggaccaact acaccttcgc caagccgata    540 gcggcagca ttctccagaa gcagccaatg ttcgtgtttc gtaagacgga agtcaaggcc    600
tctgactccg agatcaacct caaggagtcg cagaaggcct tcatgacct cgttggtata    660 tgtatttga                                                            669
```

<210> SEQ ID NO 12
<211> LENGTH: 654

```
<212> TYPE: DNA
<213> ORGANISM: Branchiostoma floridae

<400> SEQUENCE: 12
atgcctctgc ccgcaaccca tgaaatccac cttcacggct ctgtcaacgg ccacgagttc      60
gacttggtgg gcagtggaaa aggtgacccg aaagccggct cgctggtgac cgaagtgaaa     120
tccaccatgg gtcgcctgaa gttctctcct cacttgatga tcccccacct cgggtacggg     180
tactaccagt acctccccta cccggacgga ccctcgcctt ccagaccgc catgctcgat      240 ggatcggggt ataaagtcca ccgtgtgttc aactttgagg acgtggcgt gttgtccatc      300 gactacaatt atgcctacga ggggactcac atcaagtccg actttaagct gatgggaagc     360
ggtttccctg acgacggccc agtcatgacc agccaaattg tcgaccagga cggctgcgtg     420
tccaagaaga cgtatcttaa cgacaacacc atcgtggaca gcttcgactg gtcttacaat     480
ctgcagaatg ggaagcgcta cagggctcga gtgacgagca actacatctt cgggaagccc     540
ctcgcggccg atgtaatgaa gaagcagccg gtcttcgtgt accgcaagtg ctacgtgaag     600
tctacccaga ccgagatcac cctggacgag agggagaagg cgttctacga agtg          654

<210> SEQ ID NO 13
<211> LENGTH: 696
<212> TYPE: DNA
<213> ORGANISM: Branchiostoma floridae

<400> SEQUENCE: 13
atgtctgttc cgacaaacct cgacctgcac atctatggct ccatcaacgg tatggagttc      60
gacatggtgg gcggtgggag tggcaaccca aggacggat cgctgagcgt aaatgtgaag      120
tcaaccaaag gtgccctgcg cgtttctcct ctgctggtgg gcccgcatct ggggtacggc     180
cactaccagt acctaccctt ccctgacgat ccgtcgcctt ccaggcagc cgtgaacaac      240 ggcgggaatc aaatgcatcg ctcttttcaac ttcgaggacg tgccgtgct gactgccacc     300 tacaactact cctacagcgg cggcaagatc cagggagagt ttcatctggt gggcagctgt     360
ttccccaacg atagtccggt gatgaccaac gcgctgaccg tctggacag agcgtggcc      420 aagctgatgt gcgtgtccga tgacaagctt gccgagttcg tggactggac ctaccgcacc     480
agcagcggcg ggcgctaccg tgccacggtg cagaccaact tcaccttcgc aaagcccatc     540
gcagctggcc tgaagaacaa catgccgatg ttcgtgttcc gtcagctgga agtcaccggc     600
tccaaaaccg agatcggcct tcaggagcag caaaaggcgt tctccaccgt tctggtgcgt     660
tcatggttga aatataaaag agctgaaata cttttga                              696

<210> SEQ ID NO 14
<211> LENGTH: 657
<212> TYPE: DNA
<213> ORGANISM: Branchiostoma floridae

<400> SEQUENCE: 14
atgtctctcc ctacgactca cgaccttcac atcttcggct ccgtcaatgg cgcggagttc      60
gacctggtgg gaggcggaaa gggcaacccg aacgatggaa cgctggagac cagtgtgaaa     120
tccacccggg gcgccctgcc ctgctccccg ctgctgatcg acccaacct ggggtacggc      180 ttctaccagt acctgccctt ccctggcggc gcctcaccct ccaaaccgc catcacggac      240 ggagggtacc aggttcaccg tgtgttcaag tttgaagacg cggagtgct gagttgcaac     300 ttccgctaca cctacgaggg cggcaagatc aaagggagt tccagctgat cgggtcaggt     360
ttccctgccg gcgggcctgt gatgtccggc ggactgacca ccctggacag gagcgtggcc     420
```

```
aaactgcagt gctcggacga ccgcaccatc accggcacta caactggag cttctgcacc    480 accgatggga agcgccacca ggcggatgtg cagacgaact acaccttcgc caagccgctc    540
ccggccggtc tgaaggagaa gatgccgatc ttcctggggc accagatcga ggtcaaggcg    600
tccaagaccg agatcaccct gagcgagaaa gtgaaggcct catcgacac tgtgtaa       657
```

<210> SEQ ID NO 15
<211> LENGTH: 762
<212> TYPE: DNA
<213> ORGANISM: Branchiostoma floridae

<400> SEQUENCE: 15

```
atgcacgcta caaaacacac tgtaggttgt tatccactgt atctagggca ccagtctctc     60
cctaccactc acgaccttca catcttcggc tccgtcaatg gcgcggagtt cgacctggtg    120
ggaggcggaa agggcaaccc gaacgatgga acgctggaga ccagtgtgaa atccacccgg    180
ggcgccctgc cctgctcccc gctgctgatc ggacccaacc tggggtacgg cttctaccag    240
tacctgccct ccctggcgg cgcctcaccc ttccaaaccg ccatcacgga cggagggtac     300
caggttcacc gtgtgttcaa gtttgaagac ggcgagtgc tgaattgcaa cttccgcaac    360
ttccgctaca cctacgaggg cggcaagatc aaagggagt ccagctgat cgggtcaggt     420 ttccctgccg gcgggcctgt gatgcccggc ggactgacca ccctggacag gagcgtggcc    480
aaactgcagt gctcggacga ccgcaccatc accggcacta caactggag cttctgcacc    540 accgatggga agcgccacca ggcggatgtg cagacgaact acacttcgcc aagccgctcc   600
ggccggtctc aaggagaaga tgccggtctt ctggggcac cagatcgagg tcaaagcgtc    660
caagaccgag atcaccctga gcgagaaagt gaaggcttc atcgacactg tgtgaagttc    720
aagttcgccg actgtgttaa gcccagaatt cagtcctgtt aa                     762
```

<210> SEQ ID NO 16
<211> LENGTH: 668
<212> TYPE: DNA
<213> ORGANISM: Branchiostoma floridae

<400> SEQUENCE: 16

```
tctctcccaa cggctcacga ccttcacatc ttcggctccg tcaatggcgc ggagttcgac     60
ctggtgggag gcggaaaggg caacccgaac gatgaacgc tggagaccag tgtgaaatcc    120 accggggcg ccctgccctg ctccccgctg ctgatcggac ccaacctggg gtacggcttc    180
taccagtacc tgcccttccc tggcggcgcc tcacccttcc aaaccgccat cacggacgga    240
ggttaccagg ttcaccgtgt gttcaagttt gaagacggcg agtgctgaa ttgcaacttc     300 cgctacacct acgaggggg caagatcaaa ggggagttcc agctgatcgg gtcaggtttc    360
cctgccggcg gtcctgtgat gtccggcgga ctgaccaccc tggacaggag cgtggccaaa    420
ctgcagtgct cggacgactg caccatcacc ggcactaaca actggagctt ctgcaccacc    480
gatgggaagc gccatcaggc ggatgtgcag acgaactaca tcttcgccaa gccgctcccg    540
gccggtctga aggagaagat gccgatcttc ctggggcacc agatcgaggt caaggcgtcc    600
aagaccgaga tcaccctgtg cgagaaagtg aaggccttca tcgacactgt gatctgcttg    660
agatttag                                                            668
```

<210> SEQ ID NO 17
<211> LENGTH: 669
<212> TYPE: DNA
<213> ORGANISM: Branchiostoma floridae

<400> SEQUENCE: 17

```
atgagtccaa tttcacctct ccaacgact cacgaggtgc acgtctatgg ctctatcaac      60
ggtgttgagt ttgacttggt gggtagcggc aaaggcaacc cgaaggatgg ttctgaggag    120
atccaagtga agtccactaa gggtcccctc ggattctccc cgtacatcgt ggtgcccaac    180
atcgggtacg gcttccacca gtacctgccc ttcccagacg ggatgtcgcc tttccaggcc    240
gctgcggacg atggctcggg ctacgtagtc catcgtacga ttcagtttga agacggtgcc    300
tcgctgactg gcaactaccg atattcctac gatggaggcc acatcaaagg agagtttcat    360
gtggttggca gcggttttcc tggtgacggc cctgtgatga ccaaatcgct cacggctgtg    420
gactggagtg tggcgaccat gctcttccca acgacacca ccgttgtctc caccattgac    480
tggacttgcc ccactaccag cggcaaacgc taccatgcca cggtgaggac caactacacc    540
ttcgccaagc cgatagcggc cagcattctc cagaagcagc cgatgttcgt gttccgtaag    600
acggaagtta aggcctctga cgcggagatc aaccttaaga gtggcagaag ctttccatg    660
acctgtgag                                                            669
```

<210> SEQ ID NO 18
<211> LENGTH: 666
<212> TYPE: DNA
<213> ORGANISM: Branchiostoma floridae

<400> SEQUENCE: 18

```
atgcctctcc caacgaccca cgaattgcac atctttggtt ccttcaatgg tgtggagttt     60
gatatggttg gtcgcggcat cggcaaccct aatgacgggt atgaggagct aaacctgaag    120
tccaccaagg gtgccctcaa gttctccccc tggatcctgg tgcctcagat cgggtacggc    180
ttccaccagt acctgcctta cccggacgga atgtcgcctt ccaggccgc catgcaggac    240
ggctcagggt accaagtcca tcgcacgatg cagtttgaag acggtgcctc tctgactgcc    300
cacttccgct acacctacga gggaagccac atcaaagggg agtttcaggt gatcgggacc    360
ggattccctg ctgacggtcc tgtgatgacc aacaagctca ccgctgcgga ctggtgcgtg    420
gtcaagatgg tgtaccccaa cgacaagacc atcctcagca ctttcgactg gacctacacc    480
accaccgagg gcaaacgcta ccagagtacg gtgaggacca ctacaccctt cgccaagccg    540
atggccgcca acatcctgca gaagcagccg atgttcgtgt tccgtaagac ggagctccag    600
cactccaaga ccgagcttac cttcaaggag tggcagaaag ccttcaccga tgtgatggtg    660
tttttaa                                                              666
```

<210> SEQ ID NO 19
<211> LENGTH: 660
<212> TYPE: DNA
<213> ORGANISM: Branchiostoma floridae

<400> SEQUENCE: 19

```
atgcctctgc ccgcaaccca tgagatccac atctatggct ccgtcaacgg ccacgagttc     60
gacctggtgg gcggagggaa aggcgacccg aacgccggct cgctggtgac cgaagtaaaa    120
tccaccatgg gtcccctgaa gttctctccc cacttgatga tccccaccct cgggtacggg    180
tactaccagt acctcccccta cccggacgga ccatcgcctt ccagaccgc catgctcgat    240
ggatcggggt attcagtcca tcgcgtgttc gacttcgaag acggaggcaa gctgaccctc    300
gagtttaagt actcctacga gggttcccat atcaaggccg acatgaagtt cacgggaagc    360
ggtttccctg acgacggtcc agtcatgacc agccagattg tcgacgaaga cggctgcgtg    420
```

-continued

```
tctaagaaca ccatccataa cgacaacacc atcgtggaca acttcgactg gactaatgtc    480
ctacagaatg gaaagcgcta cagggcccac gtgaccagcc actacatctt cgggaagccc    540
ctcgcggccg atgtaatgaa gaagcagccg gtcttcgtgt accgcaagtg ctacgtgaag    600
tctaccaaga ccgagatcac cctggacgag cgagagaagg cgttctacga ggtggtttag    660
```

<210> SEQ ID NO 20
<211> LENGTH: 660
<212> TYPE: DNA
<213> ORGANISM: Branchiostoma floridae

<400> SEQUENCE: 20

```
atgcctctgc ccgcaactca tgaaatccac ctccacggct ccatcaacgg ccacgagttc    60
gacctggctg gcggtggaaa aggcgacccg aacgccggct cgctggtgac cacagcgaaa   120
tccaccaagg gtcccctgaa gttctctccc cacttgatga tcccccacct cgggtacggg   180
tactaccagt acctccccta cccggacgga ccctcgcctt ccaggccac catgttggaa    240 ggatcggggt atacagtcca ccgcgtgttt gacttcgaag atggaggcaa gctgtccatc    300
gagtttaagt actcctacga gggttcccat attaaggccg acatgaagtt cacgggaacc    360
ggtttccctg aggatgggcc ggtcatgacc agccagattg tcgaccagga cggctgcgtg    420
tccaagaaca cctacctcaa cgacaacacc atcgtggaca acttcgactg gacttacaat    480
ctgcagaacg gaaagcgcta cagagcccga gtgacgagcc actacatctt cgacaagccc    540
ttttcagccg atctcatgaa gaagcagccg gtcttcgtgt accgcaagtg ccacgtgaag    600
gcttccaaga ccgagatcaa cctcgacgag agggagaagg cgttctatga gtcggcttga    660
```

<210> SEQ ID NO 21
<211> LENGTH: 660
<212> TYPE: DNA
<213> ORGANISM: Branchiostoma floridae

<400> SEQUENCE: 21

```
atgcctctgc ccgcaaccca cgacatccac cttcacggct ccatcaacgg ccacgagttc    60
gacatggtgg ggggaggaaa aggcgacccg aacgccggct cgctggtgac cacagcgaaa   120
tccaccaagg gtccctgaa gttctctccc tacttgatga tcccccacct cgggtacggg    180
tactaccagt acctccccta cccggacgga ccctcgcctt ccagacctc catgttggaa    240 ggatcggggt atgcagtcta ccgcgtgttc gactttgaag acggaggcaa gctgactacc    300
gagtttaagt actcctacga gggttcccat atcaaggccg acatgaagct gatgggaagc    360
ggtttccctg acgacggccc agtcatgacc agccagattg tcgaccagga cggctgcgtg    420
tccaagaaga cgtatcttaa caacaacacc atcgtggaca gcttcgactg gagttacaac    480
ctgcagaatg ggaagcgcta cagggcccga gtgtcgagcc actacatctt cgacaagccc    540
ttttcagccg atctcatgaa gaagcagccg gtcttcgtgt accgcaagtg ccacgtgaag    600
gcttccaaga ccgaagtcac cctggacgag agggagaagg cgttctacga gctggcttag    660
```

<210> SEQ ID NO 22
<211> LENGTH: 660
<212> TYPE: DNA
<213> ORGANISM: Branchiostoma floridae

<400> SEQUENCE: 22

```
atgcctctgc ccgcaaccca tgaaatccac cttcacggct ccgtcaacgg ccacgagttc    60
gacttggtgg gcggtggaaa aggcgacccg aaagccggct cgctggtgac cgaagtgaaa   120
```

```
tccaccaagg gtcccctgaa gttttctccc cacttgatga tcccccacct cgggtacggg    180
tactaccagt acctccccta cccggacgga ccctcgcctt ccagaccgc catgctcgat     240 ggatcgggt acaaagtcca ccgtgtgttc aactttgagg acggtggcgt gttgtccatc    300
gagtacaatt attcctacga gggaactcac atcaagtccg actttaagct gatgggaagc   360
ggtttccctg acgacggccc agtcatgacc agccagattg tcgaccagga cggctgcgtg   420
tccaagaaga cgtatcttaa cgacaacacc atcgtggaca gcttcgactg gtcttacaac   480
ctacagaatg ggaagcgcta cagggcccga gtgacgagca actacatctt cgggaagcct   540
ctcgctgccg atgttatgaa gaagcagccg gtcttcgttt accgcaagtg ttacgtgaag   600
tctaccaaga ccgagatcac cctggacgag agggagaagg cgttctatga gctggcttag   660
```

<210> SEQ ID NO 23
<211> LENGTH: 657
<212> TYPE: DNA
<213> ORGANISM: Branchiostoma floridae

<400> SEQUENCE: 23

```
cctcttccaa caacccacga gttgcatatc tttggtacct tcaatggtgt cgagtatgac    60
atggtgggcc gtggcaaggg taaccctaat gatggatacg aagagctaaa cctgaagtcc   120
accaagggtc ccctcaagtt ctccccatgg atcctggtcc ctcagattgg gtacggcttc   180
caccagtacc tgccctaccc tgacgggatg tcgcctttcc aggccgccat gcacgatggc   240
tccggctatc aagtgcatcg cacgctggac tttgaagacg gtgccaccct gactgccgac   300
ttccgctaca cctacgaggg gagccacatc aaaggagagt ttaaggtgat cgggaccgga   360
ttccctgctg acggtcctgt gatgaccaac aagctcactg ctgcggactg tgtgtgaac    420 aagatgctgt acccggacga caagaccatc aacagcacct cgactggag ctacaccact    480 tccgagggca aacgctacca gagcacagtg agggaaaact acaccttcgc caagccaatg   540
gccgccaaca tcctgcagaa gcagccgatg ttcgtgttcc gtaagacgga gctccagcac   600
tccaagaccg agctcacctt caaggagtgg cagaaagcct tcaccgatgt gatgtaa       657
```

<210> SEQ ID NO 24
<211> LENGTH: 220
<212> TYPE: PRT
<213> ORGANISM: Branchiostoma floridae

<400> SEQUENCE: 24

```
Met Pro Leu Pro Thr Thr His Glu Leu His Ile Phe Gly Ser Phe Asn
 1               5                  10                  15

Gly Val Glu Phe Asp Leu Val Gly Arg Gly Glu Gly Asn Pro Lys Asp
             20                  25                  30

Gly Ser Gln Asn Leu His Leu Lys Ser Thr Lys Gly Ala Leu Gln Phe
         35                  40                  45

Ser Pro Trp Met Leu Val Pro His Ile Gly Tyr Gly Phe Tyr Gln Tyr
     50                  55                  60

Leu Pro Tyr Pro Asp Gly Glu Met Ser Pro Tyr Gln Ala Ala Met Tyr
 65                  70                  75                  80

Gly Gly Ser Gly Tyr Leu Met His Arg Thr Met Gln Tyr Glu Asp Gly
                 85                  90                  95

Ala Lys Ile Ser Gly His Tyr Lys Tyr Thr Tyr Glu Gly Ser His Val
            100                 105                 110

Lys Gly Glu Phe Gln Leu Ile Gly Thr Gly Phe Pro Thr Asp Gly Pro
        115                 120                 125
```

Val Met Thr Asn Gln Leu Thr Ala Ala Asp Trp Cys Val Asp Lys Leu
            130                 135                 140

Leu Tyr Pro Asn Asp Lys Thr Ile Ile Ser Lys Phe Asp Trp Ser Tyr
145                 150                 155                 160

Thr Thr Thr Asp Gly Lys Arg Tyr Gln Ala Lys Val Gln Thr Asn Phe
                165                 170                 175

Asp Phe Ala Lys Pro Met Ala Ala Asn Tyr Leu Gln Lys Gln Pro Met
                180                 185                 190

Phe Val Phe Arg Lys Thr Glu Leu Gln His Ser Lys Thr Glu Leu Lys
                195                 200                 205

Phe Lys Gln Trp Gln Lys Ala Phe His Asp Ile Met
210                 215                 220

<210> SEQ ID NO 25
<211> LENGTH: 228
<212> TYPE: PRT
<213> ORGANISM: Branchiostoma floridae

<400> SEQUENCE: 25

Met Ala Ser Ile Leu Val Pro Leu Pro Lys Thr His Glu Leu His Ile
1               5                   10                  15

Phe Gly Ser Phe Asn Gly Val Lys Phe Asp Met Val Gly Glu Gly Thr
                20                  25                  30

Gly Asn Pro Asn Glu Gly Ser Glu Glu Leu Lys Leu Lys Ser Thr Asn
                35                  40                  45

Gly Pro Leu Lys Phe Ser Pro Tyr Ile Leu Val Pro His Leu Gly Tyr
50                  55                  60

Ala Phe Asn Gln Tyr Leu Pro Phe Pro Asp Gly Met Ser Pro Phe Gln
65                  70                  75                  80

Ala Ala Met Gln Asp Glu Ser Gly Tyr Glu Asp Gly Ala Phe Val Thr
                85                  90                  95

Ala Asn Leu Arg Tyr Thr Tyr Glu Gly Ser His Ile Lys Gly Glu Phe
                100                 105                 110

Gln His Tyr Asn Val Asp Tyr Asn Ile Ile Leu Gln Val Ile Gly Thr
                115                 120                 125

Gly Phe Pro Pro Asp Gly Pro Val Met Thr Asn Lys Leu Thr Ala Leu
                130                 135                 140

Asp Trp Ser Val Val Lys Phe Val Tyr Pro Asn Asp Lys Thr Ile Leu
145                 150                 155                 160

Ser Thr Phe Asp Lys Thr Tyr Thr Thr Thr Asp Gly Lys Arg Tyr Gln
                165                 170                 175

Cys Thr Pro Arg Glu Asn Asn Thr Phe Ala Lys Pro Met Ala Ala Asp
                180                 185                 190

Ile Leu Gln Lys Gln Pro Met Phe Ile Phe His Lys Thr Glu Leu Gln
                195                 200                 205

His Ser Asn Asn Ala Glu Leu Thr Phe Lys Glu Lys Gln Thr Ala Phe
            210                 215                 220

Ser Asp Met Lys
225

<210> SEQ ID NO 26
<211> LENGTH: 164
<212> TYPE: PRT
<213> ORGANISM: Branchiostoma floridae

<400> SEQUENCE: 26

```
Met Ser Leu Pro Thr Ala His Asp Cys His Met Phe Gly Ser Ile Asn
1               5                   10                  15

Gly His Glu Phe Asp Leu Val Gly Gly Asn Gly Asn Pro Asn Asp
            20                  25                  30

Gly Thr Leu Glu Thr Lys Val Arg Ser Thr Lys Gly Ala Leu Pro Phe
            35                  40                  45

Ser Pro Val Ile Leu Ala Pro Asn Leu Gly Tyr Gly Tyr His Gln Tyr
    50                  55                  60

Leu Pro Phe Pro Ala Gly Thr Ser Pro Tyr Gln Gln Ala Ile Thr Asn
65                  70                  75                  80

Gly Val Pro Ser Cys Ser Arg Tyr Gln Lys His Arg Thr Phe Lys Phe
                85                  90                  95

Glu Asp Gly Gly Val Met Thr Ile Asn Phe Arg Tyr Thr Tyr Ser Gly
                100                 105                 110

Asn Lys Ile Lys Gly Glu Phe His Val Leu Val Gly Ser Gly Phe Pro
            115                 120                 125

Asp Asp Gly Pro Val Lys Thr His Ser Leu Gln Gln His Asp His Asn
    130                 135                 140

Val Glu Arg Leu Met Val Leu Gly Asp Lys Thr Ile Gly Ser Asp Asn
145                 150                 155                 160

Met Trp Thr Phe
```

<210> SEQ ID NO 27
<211> LENGTH: 150
<212> TYPE: PRT
<213> ORGANISM: Branchiostoma floridae

<400> SEQUENCE: 27

```
Ser Leu Pro Thr Thr His Asp Cys His Met Phe Gly Ser Ile Asn Gly
1               5                   10                  15

His Glu Phe Asp Leu Val Gly Gly Asn Gly Asn Pro Asn Asp Gly
            20                  25                  30

Thr Leu Glu Thr Lys Val Arg Ser Thr Lys Gly Ala Leu Pro Phe Ser
            35                  40                  45

Pro Val Ile Leu Ala Pro Asn Leu Gly Tyr Gly Tyr His Gln Tyr Leu
    50                  55                  60

Pro Phe Pro Ala Gly Thr Ser Pro Tyr Gln Gln Ala Ile Thr Asn Gly
65                  70                  75                  80

Gly Phe Glu Asp Gly Gly Val Met Thr Ile Asn Phe Arg Tyr Thr Tyr
                85                  90                  95

Ser Gly Asn Lys Ile Lys Gly Glu Phe His Val Val Gly Ser Gly
            100                 105                 110

Phe Pro Asp Asp Gly Pro Val Met Thr Asn Ser Leu Gln Gln His Asp
            115                 120                 125

His Asn Val Glu Arg Leu Met Val Leu Gly Asp Lys Thr Ile Gly Ser
    130                 135                 140

Asp Asn Met Trp Thr Phe
145                 150
```

<210> SEQ ID NO 28
<211> LENGTH: 216
<212> TYPE: PRT
<213> ORGANISM: Branchiostoma floridae

<400> SEQUENCE: 28

```
Met Pro Leu Pro Lys Thr His Glu Leu His Ile Phe Gly Ser Phe Asn
1               5                   10                  15
```

```
Gly Val Glu Phe Asp Met Val Ala Arg Gly Ile Gly Asn Pro Asn Glu
                20                  25                  30

Gly Ser Glu Glu Leu Asn Ala Lys Phe Thr Lys Gly Pro Leu Lys Phe
        35                  40                  45

Ser Pro Tyr Ile Leu Val Pro His Leu Gly Tyr Ala Tyr Tyr Gln Tyr
50                      55                  60

Leu Pro Phe Pro Asp Gly Met Ser Pro Phe Gln Ala Ala Met His Asp
65                  70                  75                  80

Gly Ser Gly Tyr Glu Asp Gly Ala Ser Val Thr Ala His Tyr Arg Tyr
                85                  90                  95

Thr Tyr Glu Gly Ser His Ile Lys Gly Glu Phe Gln Val Ile Gly Thr
            100                 105                 110

Gly Phe Pro Pro Asp Gly Pro Val Met Thr Asn Lys Leu Thr Ala Met
        115                 120                 125

Asp Trp Ser Val Thr Lys Met Leu Tyr Pro Asn Asp Lys Thr Ile Leu
130                 135                 140

Ser Thr Ala Asp Cys Ser Tyr Thr Thr Thr Glu Gly Lys Arg Tyr Gln
145                 150                 155                 160

Ser Lys Met Arg Glu Asn Asn Thr Phe Ala Lys Pro Met Ala Ala Asp
                165                 170                 175

Ile Leu Gln Lys Gln Pro Met Phe Val Phe Arg Lys Thr Glu Leu Gln
            180                 185                 190

His Ser Lys Thr Glu Leu Thr Phe Lys Glu Trp Gln Lys Ala Phe Thr
        195                 200                 205

Asp Val Met Ile Thr Gly His Ile
210                 215

<210> SEQ ID NO 29
<211> LENGTH: 236
<212> TYPE: PRT
<213> ORGANISM: Branchiostoma floridae

<400> SEQUENCE: 29

Met Ser Val Pro Thr Asn Leu Asp Leu His Ile Tyr Gly Ser Ile Asn
1               5                   10                  15

Gly Met Glu Phe Asp Met Val Gly Gly Ser Gly Asn Pro Lys Asp
                20                  25                  30

Ser Thr Lys Gly Ala Leu Cys Val Ser Pro Leu Leu Val Gly Pro His
        35                  40                  45

Leu Gly Tyr Gly His Tyr Gln Tyr Leu Pro Phe Pro Asp Gly Ala Ser
50                  55                  60

Pro Phe Gln Ala Ala Val Asn Asn Gly Gly Tyr Gln Met His Arg Ser
65                  70                  75                  80

Phe Asn Phe Glu Asp Gly Ala Val Leu Thr Ala Thr Tyr Asn Tyr Ser
                85                  90                  95

Tyr Ser Gly Gly Lys Ile Gln Gly Glu Phe His Lys Glu Ile Ile Glu
            100                 105                 110

Cys Leu His Val His Val Phe Gln Leu Val Gly Ser Gly Phe Pro Asp
        115                 120                 125

Asp Ser Pro Val Met Thr Asn Ala Leu Thr Gly Leu Asp Arg Ser Val
130                 135                 140

Ser Lys Leu Met Cys Thr Ser Asp Asp Lys Leu Val Glu Ser Val His
145                 150                 155                 160

Trp Ser Tyr Arg Thr Ser Ser Gly Gly Arg Tyr Arg Ala Thr Val Gln
                165                 170                 175
```

```
Thr Asn Phe Thr Phe Ala Lys Pro Ile Glu Ala Gly Leu Lys Asn Asn
            180                 185                 190

Met Pro Met Phe Val Phe Arg Gln Leu Glu Val Thr Gly Ser Lys Thr
            195                 200                 205

Glu Ile Gly Leu Gln Glu Gln Lys Ala Phe Ser Thr Val Leu Met
    210                 215                 220

Arg Leu Trp Leu Lys Cys Lys Arg Val Glu Ile Leu
225                 230                 235

<210> SEQ ID NO 30
<211> LENGTH: 243
<212> TYPE: PRT
<213> ORGANISM: Branchiostoma floridae

<400> SEQUENCE: 30

Ser Val Pro Thr Asn Leu Asp Leu His Ile Tyr Gly Ser Ile Asn Gly
1               5                   10                  15

Met Glu Phe Asp Met Val Gly Gly Ser Gly Asn Pro Lys Asp Gly
            20                  25                  30

Ser Leu Ala Val Asn Val Lys Ser Thr Lys Gly Ala Leu Arg Val Ser
            35                  40                  45

Pro Leu Leu Val Gly Pro His Leu Gly Tyr Gly His Tyr Gln Tyr Leu
    50                  55                  60

Pro Phe Pro Asp Gly Ala Ser Pro Phe Gln Ala Ala Val Asn Asn Gly
65              70                  75                  80

Gly Tyr Gln Met His Arg Ser Phe Asn Phe Glu Asp Gly Ala Val Leu
                85                  90                  95

Thr Ala Thr Tyr Asn Tyr Ser Tyr Ser Gly Gly Lys Ile Gln Gly Glu
            100                 105                 110

Phe His Lys Glu Ile Ile Glu Cys Leu His Val His Val Phe Gln Leu
        115                 120                 125

Val Gly Ser Gly Phe Pro Asp Asp Ser Pro Val Met Thr Asn Ala Leu
    130                 135                 140

Thr Gly Leu Asp Arg Ser Val Ser Lys Leu Met Cys Thr Ser Asp Asp
145                 150                 155                 160

Lys Leu Val Glu Ser Val His Trp Ser Tyr Arg Thr Ser Ser Gly Gly
                165                 170                 175

Arg Tyr Arg Ala Thr Val Gln Thr Asn Phe Thr Phe Ala Lys Pro Ile
            180                 185                 190

Ala Ala Gly Leu Lys Asn Asn Met Pro Met Phe Val Phe Arg Gln Leu
            195                 200                 205

Glu Val Thr Gly Ser Lys Thr Glu Ile Gly Leu Gln Glu Gln Gln Lys
    210                 215                 220

Ala Phe Ser Thr Val Leu Met Arg Leu Trp Leu Lys Cys Lys Arg Val
225                 230                 235                 240

Glu Ile Leu

<210> SEQ ID NO 31
<211> LENGTH: 243
<212> TYPE: PRT
<213> ORGANISM: Branchiostoma floridae

<400> SEQUENCE: 31

Met Ser Val Pro Thr Asn Leu Asp Leu His Ile Tyr Gly Ser Ile Asn
1               5                   10                  15

Gly Met Glu Phe Asp Met Val Gly Gly Gly Ser Gly Asn Pro Asn Asp
```

```
                        20                  25                  30
Gly Ser Leu Ser Val Asn Val Lys Ser Thr Lys Gly Ala Leu Arg Val
            35                  40                  45

Ser Pro Leu Leu Val Gly Pro His Leu Gly Tyr Gly His Tyr Gln Tyr
 50                  55                  60

Leu Pro Phe Pro Asp Gly Pro Ser Pro Phe Gln Ala Ala Val Asn Asn
65                   70                  75                  80

Gly Gly Tyr Gln Met His Arg Ser Phe Asn Phe Glu Asp Gly Ala Val
                    85                  90                  95

Leu Thr Ala Thr Tyr Asn Tyr Ser Tyr Ser Gly Gly Lys Ile Gln Gly
                100                 105                 110

Glu Phe His Val Val Thr Glu Cys Leu His Val His Val Phe Gln Leu
            115                 120                 125

Val Gly Ser Cys Phe Pro Asp Asp Ser Pro Val Met Thr Asn Ala Leu
        130                 135                 140

Thr Gly Leu Asp Arg Ser Val Ala Lys Leu Met Cys Val Ser Asp Asp
145                 150                 155                 160

Lys Leu Ala Glu Phe Val Asp Trp Thr Tyr Arg Thr Ser Ser Gly Gly
                165                 170                 175

Arg Tyr Arg Ala Thr Val Gln Thr Asn Phe Thr Phe Ala Lys Pro Ile
                180                 185                 190

Ala Ala Gly Leu Lys Asn Asn Met Pro Met Phe Val Phe Arg Gln Leu
            195                 200                 205

Glu Val Thr Gly Ser Lys Thr Glu Ile Ser Leu Gln Glu Gln Gln Lys
        210                 215                 220

Ala Phe Ser Thr Val Leu Val Arg Leu Trp Leu Lys Cys Lys Arg Ala
225                 230                 235                 240

Glu Ile Leu

<210> SEQ ID NO 32
<211> LENGTH: 220
<212> TYPE: PRT
<213> ORGANISM: Branchiostoma floridae

<400> SEQUENCE: 32

Met Pro Leu Pro Lys Thr His Glu Leu His Ile Phe Gly Ser Phe Asn
1               5                  10                  15

Gly Val Glu Phe Asp Met Val Gly Arg Gly Ile Gly Asn Pro Asn Glu
            20                  25                  30

Gln Gly Ser Glu Glu Leu Asn Ala Lys Phe Thr Lys Gly Pro Leu Lys
        35                  40                  45

Phe Ser Pro Tyr Ile Leu Val Pro His Leu Gly Tyr Ala Tyr Tyr Gln
 50                  55                  60

Tyr Leu Pro Phe Pro Asp Gly Met Ser Pro Gln Ala Ala Met His
65                   70                  75                  80

Asp Gly Ser Gly Tyr Gln Val His Arg Thr Ile Gln Tyr Glu Asp Gly
                    85                  90                  95

Ala Ser Val Thr Ala His Tyr Arg Tyr Thr Tyr Glu Gly Ser His Ile
                100                 105                 110

Lys Gly Glu Phe Gln Val Ile Gly Thr Gly Phe Pro Pro Asp Gly Pro
            115                 120                 125

Val Met Thr Asn Lys Leu Thr Ala Met Asp Trp Ser Val Thr Lys Met
        130                 135                 140

Leu Tyr Pro Asn Asp Lys Thr Ile Leu Ser Thr Val Asp Cys Ser Tyr
145                 150                 155                 160
```

```
Thr Thr Thr Glu Gly Lys Arg Tyr Gln Ser Lys Met Arg Glu Asn Asn
            165                 170                 175

Thr Phe Ala Lys Pro Met Ala Ala Asp Ile Leu Gln Lys Gln Pro Met
            180                 185                 190

Phe Val Phe Arg Lys Thr Glu Leu Gln His Ser Lys Thr Glu Leu Thr
            195                 200                 205

Phe Lys Glu Trp Gln Lys Ala Phe Thr Asp Val Met
            210                 215             220

<210> SEQ ID NO 33
<211> LENGTH: 231
<212> TYPE: PRT
<213> ORGANISM: Branchiostoma floridae

<400> SEQUENCE: 33

Met Pro Leu Pro Lys Thr His Glu Leu His Ile Phe Gly Ser Phe Asn
1               5                   10                  15

Gly Val Lys Phe Asp Met Val Gly Glu Gly Thr Gly Asn Pro Asn Glu
            20                  25                  30

Gly Ser Glu Glu Leu Lys Leu Lys Ser Thr Asn Gly Pro Leu Lys Phe
        35                  40                  45

Ser Pro Tyr Ile Leu Val Pro His Leu Gly Tyr Ala Phe Asn Gln Tyr
    50                  55                  60

Leu Pro Phe Pro Asp Gly Met Ser Pro Phe Gln Ala Ala Met Gln Asp
65                  70                  75                  80

Glu Ser Gly Tyr Gln Val His Arg Thr Leu Gln Tyr Glu Asp Gly Ala
                85                  90                  95

Phe Val Thr Ala Asn Leu Arg Tyr Thr Tyr Glu Gly Ser His Ile Lys
            100                 105                 110

Gly Glu Phe Gln His Tyr Asn Val Asp Tyr Asn Ile Ile Leu Gln Val
        115                 120                 125

Ile Gly Thr Gly Phe Pro Pro Asp Gly Pro Val Met Thr Asn Lys Leu
    130                 135                 140

Thr Ala Leu Asp Trp Ser Val Val Lys Phe Val Tyr Pro Asn Asp Lys
145                 150                 155                 160

Thr Ile Leu Ser Thr Phe Asp Lys Thr Tyr Thr Thr Glu Gly Lys
                165                 170                 175

Arg Tyr Gln Cys Thr Phe Arg Glu Asn Ser Thr Phe Ala Lys Pro Met
            180                 185                 190

Ala Ala Asp Ile Leu Gln Lys Gln Pro Met Phe Ile Phe His Lys Thr
            195                 200                 205

Glu Leu Gln His Ser Asn Asn Ala Glu Leu Thr Phe Lys Glu Lys Gln
        210                 215                 220

Thr Ala Phe Ser Asp Met Lys
225                 230

<210> SEQ ID NO 34
<211> LENGTH: 230
<212> TYPE: PRT
<213> ORGANISM: Branchiostoma floridae

<400> SEQUENCE: 34

Pro Leu Pro Thr Thr His Glu Val His Val Tyr Gly Ser Ile Asn Gly
1               5                   10                  15

Val Glu Phe Asp Leu Val Gly Ser Gly Lys Gly Asn Pro Lys Asp Gln
            20                  25                  30
```

Gly Ser Glu Glu Ile Gln Val Lys Ser Thr Lys Gly Pro Leu Gly Phe
                35                  40                  45

Ser Pro Val Val Val Pro Asn Ile Gly Tyr Gly Phe His Gln Tyr
 50                  55                  60

Leu Pro Phe Pro Asp Gly Met Ser Pro Phe Gln Ala Ala Ala Asp Asp
 65                  70                  75                  80

Gly Ser Gly Tyr Val Val His Arg Asn Ile Gln Phe Glu Asp Gly Ala
                 85                  90                  95

Ser Leu Thr Gly Ile Tyr Arg Tyr Ser Tyr Asp Ala Gly His Ile Lys
                100                 105                 110

Gly Glu Phe Arg Tyr Val Ser Asp Ile Phe Gln Val Val Gly Ser Gly
                115                 120                 125

Phe Pro Ala Asp Gly Pro Val Met Thr Lys Ser Leu Thr Ala Val Asp
130                 135                 140

Trp Ser Val Ala Thr Met Leu Phe Pro Asn Asp Thr Thr Val Val Ser
145                 150                 155                 160

Thr Ile Asp Trp Thr Cys Pro Thr Thr Ser Gly Lys Arg Tyr His Ala
                165                 170                 175

Thr Val Arg Thr Asn Tyr Thr Phe Ala Lys Pro Ile Ala Gly Ser Ile
                180                 185                 190

Leu Gln Lys Gln Pro Met Phe Val Phe Arg Lys Thr Glu Val Lys Ala
                195                 200                 205

Ser Asp Ser Glu Ile Asn Leu Lys Glu Ser Gln Lys Ala Phe His Asp
210                 215                 220

Leu Val Gly Ile Cys Ile
225                 230

<210> SEQ ID NO 35
<211> LENGTH: 218
<212> TYPE: PRT
<213> ORGANISM: Branchiostoma floridae

<400> SEQUENCE: 35

Met Pro Leu Pro Ala Thr His Glu Ile His Leu His Gly Ser Val Asn
 1               5                  10                  15

Gly His Glu Phe Asp Leu Val Gly Ser Gly Lys Gly Asp Pro Lys Ala
                20                  25                  30

Gly Ser Leu Val Thr Glu Val Lys Ser Thr Met Gly Arg Leu Lys Phe
                35                  40                  45

Ser Pro His Leu Met Ile Pro His Leu Gly Tyr Gly Tyr Tyr Gln Tyr
 50                  55                  60

Leu Pro Tyr Pro Asp Gly Pro Ser Pro Phe Gln Thr Ala Met Leu Asp
 65                  70                  75                  80

Gly Ser Gly Tyr Lys Val His Arg Val Phe Asn Phe Glu Asp Gly Gly
                 85                  90                  95

Val Leu Ser Ile Asp Tyr Asn Tyr Ala Tyr Glu Gly Thr His Ile Lys
                100                 105                 110

Ser Asp Phe Lys Leu Met Gly Ser Gly Phe Pro Asp Asp Gly Pro Val
                115                 120                 125

Met Thr Ser Gln Ile Val Asp Gln Asp Gly Cys Val Ser Lys Lys Thr
130                 135                 140

Tyr Leu Asn Asp Asn Thr Ile Val Asp Ser Phe Asp Trp Ser Tyr Asn
145                 150                 155                 160

Leu Gln Asn Gly Lys Arg Tyr Arg Ala Arg Val Thr Ser Asn Tyr Ile
                165                 170                 175

```
Phe Gly Lys Pro Leu Ala Ala Asp Val Met Lys Lys Gln Pro Val Phe
            180                 185                 190

Val Tyr Arg Lys Cys Tyr Val Lys Ser Thr Gln Thr Glu Ile Thr Leu
        195                 200                 205

Asp Glu Arg Glu Lys Ala Phe Tyr Glu Val
    210                 215

<210> SEQ ID NO 36
<211> LENGTH: 231
<212> TYPE: PRT
<213> ORGANISM: Branchiostoma floridae

<400> SEQUENCE: 36

Met Ser Val Pro Thr Asn Leu Asp Leu His Ile Tyr Gly Ser Ile Asn
1               5                   10                  15

Gly Met Glu Phe Asp Met Val Gly Gly Ser Gly Asn Pro Lys Asp
            20                  25                  30

Gly Ser Leu Ser Val Asn Val Lys Ser Thr Lys Gly Ala Leu Arg Val
        35                  40                  45

Ser Pro Leu Leu Val Gly Pro His Leu Gly Tyr Gly His Tyr Gln Tyr
    50                  55                  60

Leu Pro Phe Pro Asp Asp Pro Ser Pro Phe Gln Ala Ala Val Asn Asn
65                  70                  75                  80

Gly Gly Asn Gln Met His Arg Ser Phe Asn Phe Glu Asp Gly Ala Val
                85                  90                  95

Leu Thr Ala Thr Tyr Asn Tyr Ser Tyr Ser Gly Gly Lys Ile Gln Gly
            100                 105                 110

Glu Phe His Leu Val Gly Ser Cys Phe Pro Asn Asp Ser Pro Val Met
        115                 120                 125

Thr Asn Ala Leu Thr Gly Leu Asp Arg Ser Val Ala Lys Leu Met Cys
    130                 135                 140

Val Ser Asp Asp Lys Leu Ala Glu Phe Val Asp Trp Thr Tyr Arg Thr
145                 150                 155                 160

Ser Ser Gly Gly Arg Tyr Arg Ala Thr Val Gln Thr Asn Phe Thr Phe
                165                 170                 175

Ala Lys Pro Ile Ala Ala Gly Leu Lys Asn Asn Met Pro Met Phe Val
            180                 185                 190

Phe Arg Gln Leu Glu Val Thr Gly Ser Lys Thr Glu Ile Gly Leu Gln
        195                 200                 205

Glu Gln Gln Lys Ala Phe Ser Thr Val Leu Val Arg Ser Trp Leu Lys
    210                 215                 220

Tyr Lys Arg Ala Glu Ile Leu
225                 230

<210> SEQ ID NO 37
<211> LENGTH: 218
<212> TYPE: PRT
<213> ORGANISM: Branchiostoma floridae

<400> SEQUENCE: 37

Met Ser Leu Pro Thr Thr His Asp Leu His Ile Phe Gly Ser Val Asn
1               5                   10                  15

Gly Ala Glu Phe Asp Leu Val Gly Gly Lys Gly Asn Pro Asn Asp
            20                  25                  30

Gly Thr Leu Glu Thr Ser Val Lys Ser Thr Arg Gly Ala Leu Pro Cys
        35                  40                  45

Ser Pro Leu Leu Ile Gly Pro Asn Leu Gly Tyr Gly Phe Tyr Gln Tyr
```

```
                    50                  55                  60
Leu Pro Phe Pro Gly Gly Ala Ser Pro Phe Gln Thr Ala Ile Thr Asp
 65                  70                  75                  80

Gly Gly Tyr Gln Val His Arg Val Phe Lys Phe Glu Asp Gly Gly Val
                 85                  90                  95

Leu Ser Cys Asn Phe Arg Tyr Thr Tyr Glu Gly Gly Lys Ile Lys Gly
                100                 105                 110

Glu Phe Gln Leu Ile Gly Ser Gly Phe Pro Ala Gly Gly Pro Val Met
            115                 120                 125

Ser Gly Gly Leu Thr Thr Leu Asp Arg Ser Val Ala Lys Leu Gln Cys
130                 135                 140

Ser Asp Asp Arg Thr Ile Thr Gly Thr Asn Asn Trp Ser Phe Trp Thr
145                 150                 155                 160

Thr Asp Gly Lys Arg His Gln Ala Asp Val Gln Thr Asn Tyr Thr Phe
                165                 170                 175

Ala Lys Pro Leu Pro Ala Gly Leu Lys Glu Lys Met Pro Ile Phe Leu
            180                 185                 190

Gly His Gln Ile Glu Val Lys Ala Ser Lys Thr Glu Ile Thr Leu Ser
        195                 200                 205

Glu Lys Val Lys Ala Phe Ile Asp Thr Val
    210                 215

<210> SEQ ID NO 38
<211> LENGTH: 253
<212> TYPE: PRT
<213> ORGANISM: Branchiostoma floridae

<400> SEQUENCE: 38

Met His Ala Thr Lys His Thr Val Gly Cys Tyr Pro Leu Tyr Leu Gly
  1               5                  10                  15

His Gln Ser Leu Pro Thr Thr His Asp Leu His Ile Phe Gly Ser Val
                 20                  25                  30

Asn Gly Ala Glu Phe Asp Leu Val Gly Gly Lys Gly Asn Pro Asn
             35                  40                  45

Asp Gly Thr Leu Glu Thr Ser Val Lys Ser Thr Arg Gly Ala Leu Pro
 50                  55                  60

Cys Ser Pro Leu Leu Ile Gly Pro Asn Leu Gly Tyr Gly Phe Tyr Gln
 65                  70                  75                  80

Tyr Leu Pro Phe Pro Gly Gly Ala Ser Pro Phe Gln Thr Ala Ile Thr
                 85                  90                  95

Asp Gly Gly Tyr Gln Val His Arg Val Phe Lys Phe Glu Asp Gly Gly
                100                 105                 110

Val Leu Asn Cys Asn Phe Arg Asn Phe Arg Tyr Thr Tyr Glu Gly Gly
            115                 120                 125

Lys Ile Lys Gly Glu Phe Gln Leu Ile Gly Ser Gly Phe Pro Ala Gly
130                 135                 140

Gly Pro Val Met Pro Gly Gly Leu Thr Thr Leu Asp Arg Ser Val Ala
145                 150                 155                 160

Lys Leu Gln Cys Ser Asp Asp Arg Thr Ile Thr Gly Thr Asn Asn Trp
                165                 170                 175

Ser Phe Trp Thr Thr Asp Gly Lys Arg His Gln Ala Asp Val Gln Thr
            180                 185                 190

Asn Tyr Thr Ser Pro Ser Arg Ser Gly Arg Ser Gln Gly Glu Asp Ala
        195                 200                 205

Gly Leu Pro Gly Ala Pro Asp Arg Gly Gln Ser Val Gln Asp Arg Asp
```

```
                   210                 215                 220

His Pro Glu Arg Glu Ser Glu Gly Leu His Arg His Cys Val Lys Phe
225                 230                 235                 240

Lys Phe Ala Asp Cys Val Lys Pro Arg Ile Gln Ser Cys
                245                 250
```

<210> SEQ ID NO 39
<211> LENGTH: 221
<212> TYPE: PRT
<213> ORGANISM: Branchiostoma floridae

<400> SEQUENCE: 39

```
Ser Leu Pro Thr Ala His Asp Leu His Ile Phe Gly Ser Val Asn Gly
1               5                   10                  15

Ala Glu Phe Asp Leu Val Gly Gly Lys Gly Asn Pro Asn Asp Gly
                20                  25                  30

Thr Leu Glu Thr Ser Val Lys Ser Thr Arg Gly Ala Leu Pro Cys Ser
            35                  40                  45

Pro Leu Leu Ile Gly Pro Asn Leu Gly Tyr Gly Phe Tyr Gln Tyr Leu
    50                  55                  60

Pro Phe Pro Gly Gly Ala Ser Pro Phe Gln Thr Ala Ile Thr Asp Gly
65                  70                  75                  80

Gly Tyr Gln Val His Arg Val Phe Lys Phe Glu Asp Gly Val Leu
                85                  90                  95

Asn Cys Asn Phe Arg Tyr Thr Tyr Glu Gly Gly Lys Ile Lys Gly Glu
            100                 105                 110

Phe Gln Leu Ile Gly Ser Gly Phe Pro Ala Gly Gly Pro Val Met Ser
        115                 120                 125

Gly Gly Leu Thr Thr Leu Asp Arg Ser Val Ala Lys Leu Gln Cys Ser
    130                 135                 140

Asp Asp Cys Thr Ile Thr Gly Thr Asn Asn Trp Ser Phe Cys Thr Thr
145                 150                 155                 160

Asp Gly Lys Arg His Gln Ala Asp Val Gln Thr Asn Tyr Ile Phe Ala
                165                 170                 175

Lys Pro Leu Pro Ala Gly Leu Lys Glu Lys Met Pro Ile Phe Leu Gly
            180                 185                 190

His Gln Ile Glu Val Lys Ala Ser Lys Thr Glu Ile Thr Leu Cys Glu
        195                 200                 205

Lys Val Lys Ala Phe Ile Asp Thr Asp Leu Leu Glu Ile
    210                 215                 220
```

<210> SEQ ID NO 40
<211> LENGTH: 222
<212> TYPE: PRT
<213> ORGANISM: Branchiostoma floridae

<400> SEQUENCE: 40

```
Met Ser Pro Ile Ser Pro Leu Pro Thr Thr His Glu Val His Val Tyr
1               5                   10                  15

Gly Ser Ile Asn Gly Val Glu Phe Asp Leu Val Gly Ser Gly Lys Gly
                20                  25                  30

Asn Pro Lys Asp Gly Ser Glu Glu Ile Gln Val Lys Ser Thr Lys Gly
            35                  40                  45

Pro Leu Gly Phe Ser Pro Tyr Ile Val Val Pro Asn Ile Gly Tyr Gly
    50                  55                  60

Phe His Gln Tyr Leu Pro Phe Pro Asp Gly Met Ser Pro Phe Gln Ala
65                  70                  75                  80
```

Ala Ala Asp Asp Gly Ser Gly Tyr Val Val His Arg Thr Ile Gln Phe
            85                  90                  95

Glu Asp Gly Ala Ser Leu Thr Gly Asn Tyr Arg Tyr Ser Tyr Asp Gly
        100                 105                 110

Gly His Ile Lys Gly Glu Phe His Val Val Gly Ser Gly Phe Leu Gly
        115                 120                 125

Asp Gly Pro Val Met Thr Lys Ser Leu Thr Ala Val Asp Trp Ser Val
130                 135                 140

Ala Thr Met Leu Phe Pro Asn Asp Thr Thr Val Val Ser Thr Ile Asp
145                 150                 155                 160

Trp Thr Cys Pro Thr Thr Ser Gly Lys Arg Tyr His Ala Thr Val Arg
                165                 170                 175

Thr Asn Tyr Thr Phe Ala Lys Pro Ile Ala Ala Ser Ile Leu Gln Lys
                180                 185                 190

Gln Pro Met Phe Val Phe Arg Lys Thr Glu Val Lys Ala Ser Asp Ala
                195                 200                 205

Glu Ile Asn Leu Lys Glu Trp Gln Lys Ala Phe His Asp Leu
210                 215                 220

<210> SEQ ID NO 41
<211> LENGTH: 220
<212> TYPE: PRT
<213> ORGANISM: Branchiostoma floridae

<400> SEQUENCE: 41

Met Pro Leu Pro Thr Thr His Glu Leu His Ile Phe Gly Ser Phe Asn
1               5                   10                  15

Gly Val Glu Phe Asp Met Val Gly Arg Gly Ile Gly Asn Pro Asn Asp
                20                  25                  30

Gly Tyr Glu Glu Leu Asn Leu Lys Ser Thr Lys Gly Ala Leu Lys Phe
            35                  40                  45

Ser Pro Trp Ile Leu Val Pro Gln Ile Gly Tyr Gly Phe His Gln Tyr
    50                  55                  60

Leu Pro Tyr Pro Asp Gly Met Ser Pro Phe Gln Ala Ala Met Gln Asp
65                  70                  75                  80

Gly Ser Gly Tyr Gln Val His Arg Thr Met Gln Phe Glu Asp Gly Ala
                85                  90                  95

Ser Leu Thr Ala His Phe Arg Tyr Thr Tyr Glu Gly Ser His Ile Lys
            100                 105                 110

Gly Glu Phe Gln Val Ile Gly Thr Gly Phe Pro Ala Asp Gly Pro Val
        115                 120                 125

Met Thr Asn Lys Leu Thr Ala Ala Asp Trp Cys Val Val Lys Met Val
130                 135                 140

Tyr Pro Asn Asp Lys Thr Ile Leu Ser Thr Phe Asp Trp Thr Tyr Thr
145                 150                 155                 160

Thr Glu Gly Lys Arg Tyr Gln Ser Thr Val Arg Thr Asn Tyr Thr Phe
                165                 170                 175

Ala Lys Pro Met Ala Ala Asn Ile Leu Gln Lys Gln Pro Met Phe Val
                180                 185                 190

Phe Arg Lys Thr Glu Leu Gln His Ser Lys Thr Glu Leu Thr Phe Lys
                195                 200                 205

Glu Trp Gln Lys Ala Phe Thr Asp Val Met Val Phe
210                 215                 220

<210> SEQ ID NO 42

```
<211> LENGTH: 169
<212> TYPE: PRT
<213> ORGANISM: Branchiostoma floridae

<400> SEQUENCE: 42

Met Pro Leu Pro Ala Thr His Glu Ile His Ile Tyr Gly Ser Val Asn
1               5                   10                  15

Gly His Glu Phe Asp Leu Val Gly Gly Lys Gly Asp Pro Asn Ala
            20                  25                  30

Gly Ser Leu Val Thr Glu Val Lys Ser Thr Met Gly Pro Leu Lys Phe
        35                  40                  45

Ser Pro His Leu Met Ile Pro His Leu Gly Tyr Gly Tyr Tyr Gln Tyr
    50                  55                  60

Leu Pro Tyr Pro Asp Gly Pro Ser Pro Phe Gln Thr Ala Met Leu Asp
65                  70                  75                  80

Gly Ser Gly Tyr Ser Val His Arg Val Phe Asp Phe Glu Asp Gly Gly
                85                  90                  95

Lys Leu Thr Leu Glu Phe Lys Tyr Ser Tyr Glu Gly Ser His Ile Lys
            100                 105                 110

Ala Asp Met Lys Phe Thr Gly Ser Gly Phe Pro Asp Asp Gly Pro Val
        115                 120                 125

Met Thr Ser Gln Ile Val Asp Glu Asp Gly Cys Val Ser Lys Asn Thr
130                 135                 140

Ile His Asn Asp Asn Thr Ile Val Asp Asn Phe Asp Trp Thr Asn Val
145                 150                 155                 160

Leu Gln Asn Gly Lys Arg Tyr Arg Ala
                165

<210> SEQ ID NO 43
<211> LENGTH: 233
<212> TYPE: PRT
<213> ORGANISM: Branchiostoma floridae

<400> SEQUENCE: 43

Met Pro Leu Pro Ala Thr His Glu Ile His Leu His Gly Ser Ile Asn
1               5                   10                  15

Gly His Glu Phe Asp Leu Ala Gly Gly Lys Gly Asp Pro Asn Ala
            20                  25                  30

Gly Ser Leu Val Thr Thr Ala Lys Ser Thr Lys Gly Pro Leu Lys Phe
        35                  40                  45

Ser Pro His Leu Met Ile Pro His Leu Gly Tyr Gly Tyr Tyr Gln Tyr
    50                  55                  60

Leu Pro Tyr Pro Asp Gly Pro Ser Pro Phe Gln Ala Thr Met Leu Glu
65                  70                  75                  80

Gly Ser Gly Tyr Thr Val His Arg Val Phe Asp Phe Glu Asp Gly Gly
                85                  90                  95

Lys Leu Ser Ile Glu Phe Lys Tyr Ser Tyr Glu Gly Ser His Ile Lys
            100                 105                 110

Ala Asp Met Lys Arg Ser Thr Ser Asp Thr Asn Val His Val Phe Leu
        115                 120                 125

Phe Gln Phe Thr Gly Thr Gly Phe Pro Glu Asp Gly Pro Val Met Thr
130                 135                 140

Ser Gln Ile Val Asp Gln Asp Gly Cys Val Ser Lys Asn Thr Tyr Leu
145                 150                 155                 160

Asn Asp Asn Thr Ile Val Asp Asn Phe Asp Trp Thr Tyr Asn Leu Gln
                165                 170                 175
```

Asn Gly Lys Arg Tyr Arg Ala Arg Val Thr Ser His Tyr Ile Phe Asp
            180                 185                 190

Lys Pro Phe Ser Ala Asp Leu Met Lys Gln Pro Val Phe Val Tyr
        195                 200                 205

Arg Lys Cys His Val Lys Ala Ser Lys Thr Glu Ile Asn Leu Asp Glu
    210                 215                 220

Arg Glu Lys Ala Phe Tyr Glu Ser Ala
225                 230

<210> SEQ ID NO 44
<211> LENGTH: 219
<212> TYPE: PRT
<213> ORGANISM: Branchiostoma floridae

<400> SEQUENCE: 44

Met Pro Leu Pro Ala Thr His Asp Ile His Leu His Gly Ser Ile Asn
1               5                   10                  15

Gly His Glu Phe Asp Met Val Gly Gly Lys Gly Asp Pro Asn Ala
            20                  25                  30

Gly Ser Leu Val Thr Thr Ala Lys Ser Thr Lys Gly Ala Leu Lys Phe
        35                  40                  45

Ser Pro Tyr Leu Met Ile Pro His Leu Gly Tyr Gly Tyr Gln Tyr
    50                  55                  60

Leu Pro Tyr Pro Asp Gly Pro Ser Pro Phe Gln Thr Ser Met Leu Glu
65                  70                  75                  80

Gly Ser Gly Tyr Ala Val Tyr Arg Val Phe Asp Phe Glu Asp Gly Gly
                85                  90                  95

Lys Leu Thr Thr Glu Phe Lys Tyr Ser Tyr Glu Gly Ser His Ile Lys
            100                 105                 110

Ala Asp Met Lys Leu Met Gly Ser Gly Phe Pro Asp Asp Gly Pro Val
        115                 120                 125

Met Thr Ser Gln Ile Val Asp Gln Asp Gly Cys Val Ser Lys Lys Thr
    130                 135                 140

Tyr Leu Asn Asn Asn Thr Ile Val Asp Ser Phe Asp Trp Ser Tyr Lys
145                 150                 155                 160

Leu Gln Asn Gly Lys Arg Tyr Arg Ala Arg Val Ser Ser His Tyr Ile
                165                 170                 175

Phe Asp Lys Pro Phe Ser Ala Asp Leu Met Lys Lys Gln Pro Val Phe
            180                 185                 190

Val Tyr Arg Lys Cys His Val Lys Ala Ser Lys Thr Glu Val Thr Leu
        195                 200                 205

Asp Glu Arg Glu Lys Ala Phe Tyr Glu Leu Ala
    210                 215

<210> SEQ ID NO 45
<211> LENGTH: 211
<212> TYPE: PRT
<213> ORGANISM: Branchiostoma floridae

<400> SEQUENCE: 45

Met Pro Leu Pro Ala Thr His Glu Ile His Leu His Gly Ser Val Asn
1               5                   10                  15

Gly His Glu Phe Asp Leu Val Gly Gly Lys Gly Asp Pro Lys Ala
            20                  25                  30

Ser Thr Lys Gly Pro Leu Lys Phe Ser Pro His Leu Met Ile Pro His
        35                  40                  45

Leu Gly Tyr Gly Tyr Tyr Gln Tyr Leu Pro Tyr Pro Asp Gly Pro Ser

```
                 50                  55                  60
Pro Phe Gln Thr Ala Met Leu Asp Gly Ser Gly Tyr Lys Val His Arg
 65                  70                  75                  80

Val Phe Asn Phe Glu Asp Gly Val Leu Ser Ile Glu Tyr Asn Tyr
                 85                  90                  95

Ser Tyr Glu Gly Thr His Ile Lys Ser Asp Phe Lys Leu Met Gly Ser
                100                 105                 110

Gly Phe Pro Asp Asp Gly Pro Val Met Thr Ser Gln Ile Val Asp Gln
                115                 120                 125

Asp Gly Cys Val Ser Lys Lys Thr Tyr Leu Asn Asp Asn Thr Ile Val
130                 135                 140

Asp Ser Phe Asp Trp Ser Tyr Lys Leu Gln Asn Gly Lys Arg Tyr Arg
145                 150                 155                 160

Ala Arg Val Thr Ser Asn Tyr Ile Phe Gly Lys Pro Leu Ala Ala Asp
                165                 170                 175

Val Met Lys Lys Gln Pro Val Phe Val Tyr Arg Lys Cys Tyr Val Lys
                180                 185                 190

Ser Thr Lys Thr Glu Ile Thr Leu Asp Glu Arg Glu Lys Ala Phe Tyr
                195                 200                 205

Glu Leu Ala
    210

<210> SEQ ID NO 46
<211> LENGTH: 218
<212> TYPE: PRT
<213> ORGANISM: Branchiostoma floridae

<400> SEQUENCE: 46

Pro Leu Pro Thr Thr His Glu Leu His Ile Phe Gly Thr Phe Asn Gly
  1               5                  10                  15

Val Glu Tyr Asp Met Val Gly Arg Gly Lys Gly Asn Pro Asn Asp Gly
                 20                  25                  30

Tyr Glu Glu Leu Asn Leu Lys Ser Thr Lys Gly Pro Leu Lys Phe Ser
                 35                  40                  45

Pro Trp Ile Leu Val Pro Gln Ile Gly Tyr Gly Phe His Gln Tyr Leu
 50                  55                  60

Pro Tyr Pro Asp Gly Met Ser Pro Phe Gln Ala Met His Asp Gly
 65                  70                  75                  80

Ser Gly Tyr Gln Val His Arg Thr Leu Asp Phe Glu Asp Gly Ala Thr
                 85                  90                  95

Leu Thr Ala Asp Phe Arg Tyr Thr Tyr Glu Gly Ser His Ile Lys Gly
                100                 105                 110

Glu Phe Lys Val Ile Gly Thr Gly Phe Pro Ala Asp Gly Pro Val Met
                115                 120                 125

Thr Asn Lys Leu Thr Ala Ala Asp Trp Cys Val Asn Lys Met Leu Tyr
130                 135                 140

Pro Asp Asp Lys Thr Ile Asn Ser Thr Phe Asp Trp Ser Tyr Thr Thr
145                 150                 155                 160

Ser Glu Gly Lys Arg Tyr Gln Ser Thr Val Arg Glu Asn Tyr Thr Phe
                165                 170                 175

Ala Lys Pro Met Ala Ala Asn Ile Leu Gln Lys Gln Pro Met Phe Val
                180                 185                 190

Phe Arg Lys Thr Glu Leu Gln His Ser Lys Thr Glu Leu Thr Phe Lys
                195                 200                 205

Glu Trp Gln Lys Ala Phe Thr Asp Val Met
```

<210> SEQ ID NO 47
<211> LENGTH: 11
<212> TYPE: PRT
<213> ORGANISM: Branchiostoma sp.
<220> FEATURE:
<221> NAME/KEY: VARIANT
<222> LOCATION: (3)..(10)
<223> OTHER INFORMATION: Xaa in position 3 is Ala or Gly
      Xaa in position 4 is Phe, His or Tyr
      Xaa in position 5 is His, Tyr or Asn
      Xaa in position 10 is Phe or Tyr

<400> SEQUENCE: 47

Gly Tyr Xaa Xaa Xaa Gln Tyr Leu Pro Xaa Pro
1               5                   10

<210> SEQ ID NO 48
<211> LENGTH: 1570
<212> TYPE: DNA
<213> ORGANISM: Branchiostoma lanceolatum

<400> SEQUENCE: 48

| | | | | | |
|---|---|---|---|---|---|
| acaatcatgc | ctctcccagc | aacccacgag | ttacacatct | ttggctccat | caatagtttg | 60 |
| gagtttgacc | tggtgggtcg | tggcaccggc | aacccaaagg | aaggttatga | ggaactccac | 120 |
| ctgaagtcca | ccaagagtgc | cctccagttc | tccccatgga | tcctggtccc | tcaaatcggg | 180 |
| tacggctttt | accagtacct | gcccttcccc | gatggagcga | tgtcgccttt | tcaggccgct | 240 |
| atgaacgatg | gctccggata | ccaagtccat | cgcacaatgc | agtttgaaga | cggtgcaacc | 300 |
| ctgactggca | tctaccgcta | tacctacgag | ggaaccccaca | tcaaaggaga | gtttcaggtg | 360 |
| atcgggactg | gtttccctgc | tgacggccct | gtgatgacca | actcgctgac | cgctgcggac | 420 |
| tggtgcgtga | ccaagattgt | atacccgaac | gagaatacca | tcatcgacaa | attcgactgg | 480 |
| acctacacca | ctacaagtgg | caagcgctac | cagagcaatg | tgcggtccaa | cttcaccttt | 540 |
| gccaagccga | tcgcggccaa | catcctgcag | aagcagccga | tgttcgtgtt | ccgtaagacg | 600 |
| gagctaaagc | actccaagac | cgagctcaac | ttcaaggagt | ggcagacggc | ctttagcgat | 660 |
| gtgatgtgag | catctagtgt | attttcacat | ttggctggga | ataccccaaa | gaaacatgtc | 720 |
| cattttcttt | atagaaccca | attctgatat | ggagcaagga | cataaaacat | ttcacctac | 780 |
| gagtattatt | cgtctgtcaa | ttttcattgt | atttgtttga | aaacttatat | tatcgaacta | 840 |
| tgttttaacc | attggactac | agactttttgg | caggcatgct | ttagagcctt | tattttagaa | 900 |
| tgacacttta | ctcaacgacg | aaggtactaa | tactacttcc | tctggtcatt | gttttacttt | 960 |
| ggaaagggtg | tttaaacagt | caaatgtaaa | taagattgga | tgttttcat | catagttgtt | 1020 |
| ttgatactgc | ggtgaatgcg | tgctttcgct | atcttatata | ttacaataca | atacgaccac | 1080 |
| atatgattag | cagaacagta | ctacgagttt | acctttagga | tcaaaatgtc | agattacgtt | 1140 |
| aattctttcc | taatcaagtg | gatgtagtag | aggttgtacc | gccttagcag | aagacaaaat | 1200 |
| gaaaacataa | aaatacaaat | acttgacgga | cgtgcagtca | ttctctcatt | ggtcgaaccg | 1260 |
| ataaatgtga | tggacagtca | ggatcagtct | attacggctt | ggattttcta | tctgttctca | 1320 |
| aaacacaaag | acatcgtatc | tgtgctcctt | taacgtcgat | gtgtagtggt | attgtgttat | 1380 |
| taaagtttat | tgtgtaggaa | ttactagaaa | ttggagtatt | ttctagtcaa | gcctctagcc | 1440 |
| tcataaaatg | ctctggatgc | cataaaagat | ctatctgttt | gctgccatta | ttgtagttat | 1500 |
| tttgccttct | tgttattgca | aataaaggct | atgggtgcta | ctgcttaaaa | aaaaaaaaaa | 1560 |

```
aaaaaaaaaa                                                                  1570
```

<210> SEQ ID NO 49
<211> LENGTH: 1120
<212> TYPE: DNA
<213> ORGANISM: Branchiostoma lanceolatum

<400> SEQUENCE: 49

```
acaaccatgt ctctcccagc gacccacgag ttacacatct ttggctccat caatagtttg      60
gagtttgacc tggtgggtcg tggcaccggc aacccaaggg aaggttatga ggaactccac     120
ctgaagtcca ccaagagtgc cctccagttc tccccatgga tcctggtccc tcaaatcggg     180
tacggctttt accagtacct gcccttcccc gatggagcga tgtcgccttt tcaggccgct     240
atgaacgatg gctccggata ccaagtccat cgcacaatgc agtttgaaca cggtgcaacc     300
ctgactggca tctaccgcta tacctacgag ggaacccaca tcaaaggaga gtttcaggtg     360
atcgggactg gtttccctgc tgacggccct gtgatgacca ctcgctgac cgctgcggac     420
tggtgcgtga ccaagattgt atacccgaac gagaatacca tcatcgacaa attcgactgg     480
acctacacca ctacaagtgg caagcgctac atagcaatg tgcggtccaa cttcaccttt     540
gccaagccga tcgcggccaa catcctgcaa aagcagccga tgttcgtgtt ccgtaagacg     600
gagctaaagc attccaagac cgagctcaac ttcaaggagt ggcagacggc ctttggcgat     660
gtgatgtgag catctactgt attttcccat ttggctggga aataccacac aaacatgtcc     720
attttcttta tagaacccaa ttctgatatg gagcaaggga cataacaaca ttttcaccta     780
ccgaataata ttcgtctgtc aattctcatt gtaacttgtt tgaaaactta tattatcgaa     840
ctatgttctt acccattgga actaccgacc ttttggcagg catgcttata gatccttta     900
tttttagaat gacactctac tcaacgacga aggcactaat acctacttcc tcagtccatt     960
gttattacct gggaaatgtg tttaaacagt ccaaatgcca aataagaatt gaatggtctt    1020
gcaacatact tgcttttgaa cacttgccag ctaaatgcct gcctatcgcc tatcgtatta    1080
tttctacaag taaaagatta cggacccacc tatatggatt                           1120
```

<210> SEQ ID NO 50
<211> LENGTH: 775
<212> TYPE: DNA
<213> ORGANISM: Branchiostoma lanceolatum

<400> SEQUENCE: 50

```
acaaccatgt ctctcccagc gacacatgag ttacacatct ttggctcctt caacggtgtg      60
gactttgaca tggtgggtcg tggcaccggc aatccaaatg atggttatga ggagttaaac     120
ctgaagtcca ccaagggtgc cctccagttc tccccctgga tcctggtccc tcaaatcggg     180
tatggcttcc atcagtacct gcccttcccc gacgggatgt cgcctttcca ggccgccatg     240
aaagatggct ccggatacca agtccatcgc acaatgcagt tgaagacgg tgcctccctg     300
acttccaact accgctacac ctacgaggga agccacatca aggagagtt tcaggtgatc     360
gggactggtt tccctgctga cggtcctgtg atgaccaact cgctgaccgc tgcggactgg     420
tgcgtgacca agatgctgta ccccaacgac aaaaccatca tcagcacctt tgactggact     480
tacaccactg gaagtggcaa cgctaccag agcacagtgc ggaccaacta caccttgcc     540
aagccaatgg cggccaacat cctgaagaac cagccgatgt tcgtgttccg taagacggag     600
ctcaagcact ccaagaccga gctcaacttc aaggagtggc aaaaggcctt accgatgtg     660
atgtgagcgt ccagtttgtt acacttgact gggcccacac caaaagaaat attactcatt     720
```

```
agtttctgat aaaacccaaa aactgcagca aagagataaa acatttgtca cctac        775
```

<210> SEQ ID NO 51
<211> LENGTH: 893
<212> TYPE: DNA
<213> ORGANISM: Branchiostoma lanceolatum

<400> SEQUENCE: 51

```
acagtcatgc ctctcccagc aacacatgag ttacacatct ttggctcctt caacggtgtg     60
gactttgaca tggtgggtcg tggcaccggc aatccaaatg atggttatga ggagttaaac    120
ctgaagtcca ccaagggtgc cctccagttc tcccccctgga tcctggtccc gcaaatcggg   180
tatggcttcc atcagtatct gcccttcccc gacgggatgt caccttttcca ggctgccatg   240
aaagatggct ccggatacca agtccatcgc acaatgcagt ttgaagacgg tgcctccctg    300
acttccaact accgctacac ctacgaggga agccacatca aggagagtt tcaggtgatc     360
gggactggtt tccctgctga cggtcctgtg atgaccaact cgctgaccac tgcggactgg    420
tgcgtgacca agatgctgta ccccaacgac aaaaccatca tcagcacctt tgactggacc    480
tacaacactg caagtggcaa cgctaccag agcacggtgc gaaccaacta cccctttaac     540
aagccaatgg cggccaacat cctgaagaac cagccgatgt tcgtgttccg caagacggag    600
ctcaagcact ccaagaccga gctcaacttc aaggagtggc aaatggcctt tgccgatgtg    660
atgtgagcgt ccggtgtgtt acacttgact ggaaacaaac caaagaaac attacacatt    720
agtttatggt aaaaccaaat actgcagcaa agatatacaa aattgtcacc tacgaaatgt    780
caatgttcat tgttaaaaaa aatttatgat atccaagata tttacaccat ttgggctgca    840
aactgttggc aggcatgctt tagggtcatt attttcagaa tgggcaccta acg           893
```

<210> SEQ ID NO 52
<211> LENGTH: 1210
<212> TYPE: DNA
<213> ORGANISM: Branchiostoma lanceolatum

<400> SEQUENCE: 52

```
acagtcatgc ctctcccagc aacacacgag ttacacatct ttggttcctt caatggtgtg     60
gactttgaca tggtgggtca tggcaccggc aatccaaatg atggttatga ggagttaaac    120
ctgaagtcca ccaagggtgc cctccagttc tcccccctgga tcctggtccc tcaaatcggg   180
tatggcttcc accagtacct gcccttcccc gacgggatgt cgccttttca ggctgccatg    240
aaagatggct caggatacca agtccatcgc acaatgcagt ttgaagacgg tgcctccctg    300
acttccaact accgctacac ctacgaggga agccacatca aggagagtt tcaggtgaac     360
gggactggtt tccctgctga cggccctgtg atgaccaact cgctgaccac tgcggactgg    420
tgcgtgacca agatgctgta tcctaacgac aagaccatca tcagcacctt tgactggacc    480
tacaccactg aagtggcaa cgctaccag agcacagtgc ggaccaacta cccctttgcc     540
aagccaatgg cggccaacat cctgcagaac cagccgatgt tcgtgttccg caagacggag    600
ctcaagcact ccaagaccga gctcaacttc aaggagtggc aaaaggcttt tgccgatgtg    660
atgtgagcgt ccagtttgtt acacttgact ggaaacaaac caaagaaac attacacatt    720
agtttatggt aaaaccaaat actgcagcaa agatatacaa aattgtcacc tacgaatgtc    780
aatgttcatt gttaaaaaaa acttatgata tccaagatat ttacaccatt tggctgcaaa    840
ctgttgggca ggcatgcttt agggtcatta tttcagaatg gcacctacga aggtactaat    900
actgcttcct ctggtcattt ttttcacttc gaaagggcgt tttaacagtc aagtgtaaat    960
```

```
ataattggat gtttgtcatc atgattgctt tgatactgcg gtgaatgcgt gctttcgctt    1020
ttcttatatt ataacaatac taccttatgt gaataagcaa ggattgctag gtacggagct    1080
taccttagga tcggaaatgt tcagattacc tttaaatttt tcctgatcaa ttggatgtag    1140
tgaatggcct accagtccac cctagctccc atttacaaga tgactaaatt tttcttacac    1200
ccgggcggtc                                                           1210

<210> SEQ ID NO 53
<211> LENGTH: 891
<212> TYPE: DNA
<213> ORGANISM: Branchiostoma lanceolatum

<400> SEQUENCE: 53
acaaccatgt ctctcccagc gacccacgag ttacacatct ttggctccat caatagtttg      60
gagtttgacc tggtgggtcg tggcaccggc aacccaaagg aaggttatga ggaactccac     120
ctgaagtcca ccaagagtgc cctccagttc tccccatgga tcctggtccc tcaaatcggg     180
tacggctttt accagtacct gcccttcccc gatggagcga tgtcgccttt tcaggccgct     240
atgaacgatg gctccggata ccaagtccat cgcacgatgc agtttgaaga cggtgcaacc     300
ctgactggca tctaccgcta tacctacgag ggaacccaca tcaaaggaga gtttcaggtg     360
atcgggactg gtttccctgc tgacggcccct gtgatgacca ctcgctgac cgctgcggac     420 tggtgcgtga ccaagattgt atacccgaac gagaatacca tcatcgacaa attcgactgg     480
acctacacca ctacaagtgg caagcgctac cagagcaatg tgcggtccaa cttcaccttt     540
gccaagccga tcgcggccaa catcctgcag aagcagccga tgttcgtgtt ccgtaagacg     600
gagctaaagc actccaagac cgagctcaac ttcaaggagt ggcagacggc ctttagcgat     660
gtgatgtgag catctagtgt attttcacat ttggctggga aatacccaaa gaaacatgtc     720
cattttcttt atagaaccca attctgtatt ggagcaagga cataaaacat tttcacctac     780
gagtattatt cgtctgtcaa ttttcattgt atttgtttga aaacttatat tatcgaacta     840
tgttttaacc attggactac agactttttgg caggcatgct ttagagccct c             891

<210> SEQ ID NO 54
<211> LENGTH: 882
<212> TYPE: DNA
<213> ORGANISM: Branchiostoma lanceolatum

<400> SEQUENCE: 54
acaaacatgc ctcttccagc gacccatgag ttacacatct ttggctcctt caatggtgtg      60
gagtttgaca tggttggtcg cggcactggc aacccaaatg atgggtctga ggatttacac     120
ctgaagtcca ccaagggtgc cctccagttc tccccctgga tcctaatccc tcacatcggg     180
tacggctttc accagtacct gcccttttccc gacgggatgt cgccttttcca ggccgccatg     240 caagacggct ccggataccca agtgcatcgc actatgcagt ttgaagacgg tgcctccctg     300 actgcaaaact tccgctacac ctacgaggga agccacatca aggagagtt tcaggtgatc     360 gggtccggtt tccctgctga cggccctgtg atgaccaact cgctgaccgc tgtggactgg     420
tgcgtggcca agatgctgta ccccaacgac aagaccatca tagcaccctt tgactggacc     480
tacaccactg gaagtggcaa gcgctaccag agcacagtgc ggaccaacta cacctttgcc     540
aagccaatgg cggccaacat cctgaagaac cagccgatgt tcgtgttccg caagacggag     600
ctcaagcact ccaagaccga gctcaacttc aaggagtggc aaaaggcctt tgccgatgtg     660
atgtgagcgt ccggtgtgtt acacttgact ggaaacaaac caaagaaac gttacacatt     720
```

| | | | | |
|---|---|---|---|---|
| agtttatggt | aaaaccaaat | actgcagcaa | agatatacaa | aattgtcacc tacgaatgtc | 780 |
| aatgttcatt | gttaaaaaaa | aaacttatga | tatccaagat | atttacacca tttggctgca | 840 |
| aactgttggc | aggcatgctt | tagggtcatt | atttcagaat | gg | 882 |

<210> SEQ ID NO 55
<211> LENGTH: 1239
<212> TYPE: DNA
<213> ORGANISM: Branchiostoma lanceolatum

<400> SEQUENCE: 55

| | | | | |
|---|---|---|---|---|
| acaaacatgc | ctcttccagc | gacccacgat | ttacacatct | ccggctcaat caatggacat | 60 |
| gagtttgact | tggaagggtc | tggtaagggc | aatgaaaaag | aaggttatca ggagctccac | 120 |
| ctaaagtcca | acaggggtga | cctgtcattc | tccccctgga | tcctggtccc aaacaccggc | 180 |
| tacggtttct | accagtacct | gcccttcccc | gacggagcga | tgtcgcctta ccaggccgcc | 240 |
| atgcacgatg | gctccggata | cgtgatgcat | cgttcaatgc | agtttgagga tggtgccatg | 300 |
| ctgcattcag | accaccgcta | catctataag | ggaaaccata | tcaaaggaga gtttcggctg | 360 |
| accggaagcg | gtttccctgc | tgacggccct | gtgatgacca | actcgctgac cgctgcggac | 420 |
| tggtgcgtcg | acaagctgct | gtacccaaac | gacaacacca | taatcggcaa attcgactgg | 480 |
| acctacacca | ctaccagtgg | caagcgctac | aaagtgatg | tgcagaccaa cgtcacattt | 540 |
| ggcaagccaa | tagcggccga | cattttgaag | aagcagccaa | tgttcgtgtt ccgcatgatg | 600 |
| gaactcaagc | acaccaagac | tgagctcaac | ttcaagcagt | ggcagaaggc attccaggac | 660 |
| atcgcctgat | gcgctcgatc | ctcaagtgta | ttacattttg | cttgacaaca cctcttagaa | 720 |
| atatcctttt | tttttctgtc | aatacccaat | attgcaacaa | gaagatacaa gctttgtctc | 780 |
| agcagaactt | tatctaaaca | gtgtcgttct | agaactgata | atgatgggct cctacctttt | 840 |
| tatttttcaa | ttaaaacttt | ttaaaaatgt | gctttatcta | cgaaaatcca atgtatttac | 900 |
| atcattccgc | caaacatttt | ttctgggcaa | ttaccgcttc | ctcgatcata cttatgttct | 960 |
| cagatgggac | acctcactca | agagtataca | tttagatcac | tgcctcccca tattccgatt | 1020 |
| tatttttcat | cttcaagggg | gtgctggtaa | tagtcacatg | taaattctta cagtgaaatt | 1080 |
| ttttccatcg | gtttctacca | cttggcgttt | tggaatgcat | aggaactcgg aatgcctgca | 1140 |
| tttcttaacg | tattgtaatt | acaattacgg | actacgtttt | attcatcacg acgaaagaat | 1200 |
| ctctgcccat | atggaaaaaa | cccttccttc | tcttgaaat | | 1239 |

<210> SEQ ID NO 56
<211> LENGTH: 874
<212> TYPE: DNA
<213> ORGANISM: Branchiostoma lanceolatum

<400> SEQUENCE: 56

| | | | | |
|---|---|---|---|---|
| acaaacatgc | ctcttccagc | gacccacgat | ttacacatct | ccggctctat caatggacat | 60 |
| gagtttgact | tggagggcag | tggcaagggc | aatgcaaaag | aaggttatca ggagctccac | 120 |
| ctaaagtcca | acaggggtga | cctgtcattc | tccccctgga | tcctggtccc aaacatcggc | 180 |
| tacggcttct | accagtacct | gcccttcccc | gacggagcga | tgtcgcctta ccaggccgcc | 240 |
| atgcacgatg | gctccggcta | cgtgatgcat | cgtacaatgc | aatttgagga tggtgccatg | 300 |
| ctgcattcag | accaccgcta | tacctataag | ggaaaccata | tcaaaggaga gtttaggctg | 360 |
| accggaagtg | gtttccctgc | tgacggccct | gtgatgacca | actcgctgac cgctgcggac | 420 |
| tggtgcgtgg | acaagctgct | gtatcctact | gagaacaccc | taatcggcaa attcgactgg | 480 |

| | |
|---|---:|
| acttacacca ctaccagcgg caagcgctac caaagtgatg tgcagaccaa cgtcaccttt | 540 |
| gccaagccaa tggctgccga cattctgaag aagcagccga tgttcgtgtt tcgcaaggtc | 600 |
| gaactcaagc acaccaagac agagctcaac ttcaagcagt ggcagaaggc attccaggac | 660 |
| atcgtgtgat gcgctcgatc ctccagtgta ttacatttgc tttacaacac cctaagaaat | 720 |
| atccatattt ttctgttaat accaaatatt tcaataagaa tatacaaact ttgtctcggc | 780 |
| agaacttaat caaaacagag tcgttctaga acttagaata atggtctcct accattttt | 840 |
| tttcaatcga aacttttaa aaatgtgctt tgtt | 874 |

<210> SEQ ID NO 57
<211> LENGTH: 961
<212> TYPE: DNA
<213> ORGANISM: Branchiostoma lanceolatum

<400> SEQUENCE: 57

| | |
|---|---:|
| acaaccatgt ctctcccagc gacccacgat ttacacatct ccggctcaat caatggacat | 60 |
| gagtttgact tggaaggcag tgcaagggc aatgcaaaag aaggttatca ggagctccac | 120 |
| ctaaagtcca caagggtga cctgtcattc tccccctgga tcctggtccc aaacatcggc | 180 |
| tacggcttct accagtacct gcccttcccc gacggagcga tgtcgcctta ccaggccgcc | 240 |
| atgcacgatg gctccggata cgtgatgcat cgttcaatgc agtttgagga tggtgccatg | 300 |
| ctgcattcag accaccgcta catctataag ggaaaccata tcaaggaga gtttcggctg | 360 |
| accggaagcg gtttccctgc tgacggccct gtgatgacca actcgctgac cgctgcggac | 420 |
| tggtgcgtcg acaagctgct gtacccaaac gacaacacca taatcggcaa attcgactgg | 480 |
| acctacacca ctaccagtgg caagcgctac caaagtgatg tgcagaccaa cgtcacattt | 540 |
| ggcaagccaa tagcggccga cattttgaag aagcagccaa tgttcgtgtt ccgcaaggtg | 600 |
| gaactcaagc acaccaagac tgagctcaac ttcaagcagt ggcagaaggc attccaggac | 660 |
| atcgcctgat gcgctcgatc ctcaagtgta ttacatttgc ttgacaacac ccttagaaat | 720 |
| atccttttttt ttttctgtca atacccaata ttgcaacaag aagatacaaa ctttgtctca | 780 |
| gcagaacttt atcaaaacag tgtcgttcta gaactgataa tgatggtctc ctaccatttt | 840 |
| attttttcaa ttaaaacttt ttaaaaatgt gctttatcta cgaaaatcca atgtattttc | 900 |
| accattcgtc aaacattttt ttcctgggcc attaccgctt ctcgatcata cttatgtctc | 960 |
| a | 961 |

<210> SEQ ID NO 58
<211> LENGTH: 1712
<212> TYPE: DNA
<213> ORGANISM: Branchiostoma lanceolatum

<400> SEQUENCE: 58

| | |
|---|---:|
| acaaccatgt ctctcccagc gacccacgat ttacacatct ccggctctat caatggacat | 60 |
| gagtttgact tggagggcag tgcaagggc aatgcaaaag aaggttatca ggagctccac | 120 |
| ctaaagtcca caagggtga cctgtcattc tccccctgga tcctggtccc aaacatcggc | 180 |
| tacggcttct accagtacct gcccttcccc gacggagcga tgtcgcctta ccaggccgcc | 240 |
| atgcacgatg gctccggcta cgtgatgcat cgtacaatgc aatttgagga tggtgccatg | 300 |
| ctgcattcag accaccgcta tacctataag ggaaaccata tcaaggaga gtttaggctg | 360 |
| accgggagcg gtttccctgc tgacggccct gtgatgacca actcgctgac cgcggtggac | 420 |
| tggtgtgtgg ataagctgct gtaccccaac gagaacacca taatcggcaa attcgactgg | 480 |

| | |
|---|---|
| acctacacca ctaccagtgg caagcgctac caaagtgatg tgcagaccaa cgtcaccttt | 540 |
| gccaagccaa tagcggccga cattctgaag aagcagccga tgttcgtgtt ccgcaaggtg | 600 |
| gagctcaagc actccaagac cgagctcaac ttcaagcagt ggcagaaggc attccaggac | 660 |
| atcgtgtgat gcgctcgatc ctccagtgta ttacatttgc tttacaacat cctaagaaat | 720 |
| atccattttt ttctgttaat acccaatatt gcaacaagaa gatacaaact ttgtctcggc | 780 |
| agaacttaat caaacagtg tcgttctaga acctagaata atggtctcct accattttt | 840 |
| ttaaatcaaa acttttaaa aatgtgcttt gtttacgaat atctaatgta tttcaccatt | 900 |
| cgtcaaacat ttttttttcc tgggccatta ccgcttctcg ataatacttt tgttctcaag | 960 |
| atggacacct cactctagag tatacattca gatactgatt tcccatatcc gtttctttta | 1020 |
| atttcaaagg gtgttagtaa tcgtcaaatg taaatctaac tggatatttt ttatcgtttc | 1080 |
| taccactttg cttttggta tgcatagaga gctgaatgca tgcatttctt atcgtatgta | 1140 |
| ttacaaatac ttctgacctt cccgttttga aattaacaga tggatatgta ctatcgacaa | 1200 |
| tcctctctct ctctatagga tcaaatcaca tgctattgcc taatcgggaa agatgcagta | 1260 |
| gctgcacctt cgtagcttca catctatttg atacaatcta aattccaaat atatgagctc | 1320 |
| tgtttttaaa ttcgctcttg ggataacagt aaagcctgtc ggaaatccgc gtgtggttgt | 1380 |
| agaaaaatga ggctagctgt cggcgtattt ggaaaagggt cttcaaattg aatgcgtttc | 1440 |
| ccattcagta ccatcttcag acagatcact tagtaattca ggtaataaag atctggttcg | 1500 |
| taaaaatgca agtataaaca tcggttgagc tcaaacaggg agattgtaga aatatatgcg | 1560 |
| aaatatcttg gaatatcact gaagcttttt agtttcaaaa gtagcctcga agacagccct | 1620 |
| ataccctag actgttcatt aaatttcttt tggtagttca gcttgaatac ataaagattg | 1680 |
| ggggtactaa aaacaaaaaa aaaaaaaaaa aa | 1712 |

<210> SEQ ID NO 59
<211> LENGTH: 2155
<212> TYPE: DNA
<213> ORGANISM: Branchiostoma lanceolatum

<400> SEQUENCE: 59

| | |
|---|---|
| acaatcatgt ctctcccagc aacccacgat ttacacatct ccggctcaat caatggacat | 60 |
| gagtttgact tggaaggcag tggcaagggc aatgcaaaag aaggttatca ggagctccac | 120 |
| ctaaagtcca acaagggtga cctgtcattc tcccctggga tcctggtccc aaacatcggc | 180 |
| tacggcttct accagtacct gcccttcccc gacggagcga tgtcgcctta ccaggccgcc | 240 |
| atgcacgatg gctccggata cgtgatgcat cgttcaatgc agtttgagga tggtgccatg | 300 |
| ctgcattcag accaccgcta catctataag ggaaaccata tcaaggaga gtttcggctg | 360 |
| accggaagcg gtttccctgc tgacggccct gtgatgacca actcgctgac cgctgcggac | 420 |
| tggtgcgtcg acaagctgct gtacccaaac gacaacacca taatcggcaa attcgactgg | 480 |
| acctacacca ctaccagtgg caagcgctac caaagtgatg tgcagaccaa cgtcacattt | 540 |
| ggcaagccaa tagcggccga cattttgaag aagcagccaa tgttcgtgtt ccgcaaggtg | 600 |
| gaactcaagc acaccaagac tgagctcaac ttcaagcagt ggcagaaggc attccaggac | 660 |
| atcgcctgat gcgctcgatc ctcaagtgta ttacatttgc ttgacaacac ccttagaaat | 720 |
| atccttttt tttctgtcaa tacccaatat tgcaacaaga agatacaaac tttgtctcag | 780 |
| cagaacttta tcaaacagtg gtcgttctag aactgataat gatggtctcc taccatttta | 840 |
| ttttttcaat taaaactttt taaaaatgtg ctttatctac gaaaatccaa tgtatttca | 900 |

-continued

| | |
|---|---|
| ccattcgtca aacatttttt cctggccatt accgcttctc gatcatactt atgttctcaa | 960 |
| gatggacacc tcactctaga gtatacattt agatactgct tcccatatcc gtttcttttc | 1020 |
| atttcaaggg gtgttggtaa tagtcaaatg taaatcttgc aggatatttt tcatcgtttt | 1080 |
| taccactttg cttttggta tgccaggaca tcgcctgatg cgctcgatcc tcaagtgtat | 1140 |
| tacatttgct ggacaacacc cttagaaata tcctttttt ttcgttcaat accccatatt | 1200 |
| gcaacaagaa gatacaaact ttgtctcagc agaactttat caaaacagtg tcgttctaga | 1260 |
| actgataatg atggtctcct accattttat tttttcaatt aaaactttt aaaaatgtgc | 1320 |
| tttatctacg aaaatccaat gtattttcac cattcgtcaa acatttttc ctggccatta | 1380 |
| ccgcttctcg atcatactta tgttctcaag atggacacct cactctagag tatacattta | 1440 |
| gatactgctt cccatatccg tttcttttca tttcaagggg tgttggtaat agtcaaatgt | 1500 |
| aaatcttgca ggatatttt catcgttttt accactttgc ttttggtat gcatagagaa | 1560 |
| ctgaatgcat gcatttctta tcgtatgtaa tacaatacag accttcctgt tttattatca | 1620 |
| gcagatagat ctgcactatg aacaatcctc tctctagata taggatcaaa ttacatgcta | 1680 |
| ttgcctaatc aggtagatac agtagctgac ccccccgta gcttcaaatc tatatgatac | 1740 |
| aaatcaaaat tcaaaatata tgagctctgt tttaaattc gctcttggta taacaataaa | 1800 |
| gtctgtcgga aacccgcgtg tggttgtaag aaaacgaggt taactgtcgg cgtattttac | 1860 |
| aaatttaatg cgtttcccat taagtccctt tttcagaaag atcacttagt aattcaggta | 1920 |
| gtaaagatct ggttcgtaaa aatgttatga taaatatcgg ttaagctcaa aaagggtgat | 1980 |
| tgtagatata tatgcgaaat atcttcgaat atcactgaag ccttttagtt tcaaaagtcg | 2040 |
| cctccaagac aggcctatat cctacggctg ttcattaaac ttcttttgt ggttcaactt | 2100 |
| gaagaaataa aaagatgagg gtacttttaa aaaaaaaaa aaaaaaaaa aaaaa | 2155 |

<210> SEQ ID NO 60
<211> LENGTH: 721
<212> TYPE: DNA
<213> ORGANISM: Branchiostoma lanceolatum

<400> SEQUENCE: 60

| | |
|---|---|
| aacaacatgt ctctccctaa gacccacgat ttacacatct ccggctctgt caatggacat | 60 |
| gagtttgact tggagggcag tggcaagggc aatgcaaaag aaggttatca ggagctccac | 120 |
| ctaaagtcca acaggggtga cctgtcattc tccccttgga tcctggtccc aaacatcggc | 180 |
| tatggcttct accagtacct gcccttcccc gacggagcga tgtcgcctta ccaggccgcc | 240 |
| atgcacgatg gctccggata cgtgatgcat cgtgcaatgc ggtttgagga tggtgctatg | 300 |
| ctgcattcag accaccgcta tacctacaac ggaaacaata tcaaaggaga gtttcggctg | 360 |
| accgggagcg gtttccctgc tgacggccct gtgatgacca actcgctgac cgctgcggac | 420 |
| tggtgtgtgg acaagctgct gtaccccaac gagaacacca ttatcggcaa attcgactgg | 480 |
| acatacacca ctacaagtgg caagcgctac caaagtgatg tgcagaccaa cgtcaccttt | 540 |
| ggcaagccaa tatcggccga cattctgaag aagcagccga tgttcgtgtt ccgtaaggtg | 600 |
| gaactcaagc actccaagac cgagctcaac ttcaagcagt ggcagaaggc attccaggac | 660 |
| atcgtgtgat gcgctcgatc ctccagtgta ttacatttgc tttacaacac cctaaaaaaa | 720 |
| a | 721 |

<210> SEQ ID NO 61
<211> LENGTH: 925
<212> TYPE: DNA

<213> ORGANISM: Branchiostoma lanceolatum

<400> SEQUENCE: 61

```
acaaacatgc ctcttccagc gacccacgat ttacacatct ccggctctat caatggacat    60
gagtttgact tggagggcag tggcaagggc aatgcaaaag aaggttatca ggagctccac   120
ctaaaatcca acaagggtga cctgtcattc tccccctgga tcctggtccc aaacatcggc   180
tacggcttct accagtacct gcccttcccc gacggagcga tgtcgcctta ccaggccgcc   240
atgcacgatg gctccggata cgtgatgcat cgtgcaatgc ggtttgagga tggtgccatg   300
ctgcattcag accaccgcta tacctacaac ggaaaccata tcaaaggaga gtttcggctg   360
accgggagcg gtttccctgc tgacggccct gtgatgacca actcgctgac cgctgcggac   420
tggtgtgtgg ataagctgct gtacccccgac gagaacacca ttatcggcaa attcgactgg   480
acatacacca ctaccagtgg caagcgctac caaagtgatg tgcagaccaa cgtcacattt   540
gccaagccaa tatcggccga cattctgaag aagcagccga tgttcgtgtt ccgtaaggtg   600
gagctcaagc actccaagac cgagctcaac ttcaagcagt ggcaaaaggc attccaggac   660
atcgtgtgat gcgctcgatc ctccagtgta ttacatttgc tttacaacac cctaagaaat   720
ttttttttct gttaataccc aatattgcaa caagaagata caaacattgt attggcagaa   780
gttaatcaaa acagtgtcgt tctagaacta agaatgatgg tctcctatca ttttattttt   840
caatcaaaac ttttttaaaat tgtgctttgt ttacgaatat ccaatctata ttttcaccat   900
tcgtcaaaca tttttcctg gccat                                          925
```

<210> SEQ ID NO 62
<211> LENGTH: 926
<212> TYPE: DNA
<213> ORGANISM: Branchiostoma lanceolatum

<400> SEQUENCE: 62

```
acaaccatgt ctctcccagc gacccacgat ttacacatct ccggctctat caatggacat    60
gagtttgact tggagggcag tggcaagggc aatgcaaaag aaggttatca ggagctccac   120
ctaaaatcca acaagggtga cctgtcattc tccccctgga tcctggtccc aaacatcggc   180
tacggcttct accagtacct gcccttcccc gacggagcga tgtcgcctta ccaggccgcc   240
atgcacgatg gctccggata cgtgatgcat cgtgcaatgc ggtttgagga tggtgccatg   300
ctgcattcag accaccgcta tacctacaac ggaaaccata tcaaaggaga gtttcggctg   360
accgggagcg gtttccctgc tgacggccct gtgatgacca actcgctgac cgctgcggac   420
tggtgtgtgg ataagctgct gtacccccgac gagaacacca ttatcggcaa attcgactgg   480
acatacacca ctaccagtgg caagcgctac caaagtgatg tgcagaccaa cgtcacattt   540
gccaagccaa tatcggccga cattctgaag aagcagccga tgttcgtgtt ccgtaaggtg   600
gagctcaagc actccaagac cgagctcaac ttcaagcagt ggcaaaaggc attccaggac   660
atcgtgtgat gcgctcgatc ctccagtgta ttacatttgc tttacaacac cctaagaaat   720
ttttttttct gttaataccc aatattgcaa caagaagata caaacattgt attggcagaa   780
gttaatcaaa acagtgtcgt tctagaacta agaatgatgg tctcctatca ttttattttt   840
caatcaaaac ttttttaaaat tgtgctttgt ttacgaatat ccaatctata ttttcaccat   900
tcgtcaaaca tttttcct ggccat                                          926
```

<210> SEQ ID NO 63
<211> LENGTH: 726
<212> TYPE: DNA

<213> ORGANISM: Branchiostoma lanceolatum

<400> SEQUENCE: 63

| | | | | | |
|---|---|---|---|---|---|
| aacaacatgt | ctctccctaa | gacccacgat | ttacacatct | ccggctctgt | caatggacat | 60 |
| gagtttgact | tggagggcag | tggcaagggc | gatgcaaaag | aaggttatca | ggagctccac | 120 |
| ctaaagtcca | acaggggtga | cctgtcattc | tccccttgga | tcctggtccc | aaacatcggc | 180 |
| tatggcttct | accagtacct | gcccttcccc | gacggagcga | tgtcgcctta | ccaggccgcc | 240 |
| atgcacgatg | gctccggata | cgtgatgcat | cgtgcaatgc | ggtttgagga | tggtgctatg | 300 |
| ctgcattcag | accaccgcta | tacctacaac | ggaaacaata | tcaaaggaga | gtttcggctg | 360 |
| accgggagcg | gtttccctgc | tgacggccct | gtgatgacca | actcgctgac | cgctgcggac | 420 |
| tggtgtgtgg | acaagctgct | gtaccccaac | gagaacacca | ttatcggcaa | attcgactgg | 480 |
| acatacacca | ctacaagtgg | caagcgctac | caaagtgatg | tgcagaccaa | cgtcaccttt | 540 |
| ggcaagccaa | tatcggccga | cattctgaag | aagcagccga | tgttcgtgtt | ccgtaaggtg | 600 |
| gaactcaagc | actccaagac | cgagctcaac | ttcaagcagt | ggcagaaggc | attccaggac | 660 |
| atcgtgtgat | acgctcgatc | ctccagtgta | ttacatttgc | tttacaacac | cctaaaaaat | 720 |
| aaaaaa | | | | | | 726 |

<210> SEQ ID NO 64
<211> LENGTH: 598
<212> TYPE: DNA
<213> ORGANISM: Branchiostoma lanceolatum

<400> SEQUENCE: 64

| | | | | | |
|---|---|---|---|---|---|
| acaaccatgt | ctctcccagc | gacccatgag | ttgcacattt | ttgacaaaat | caatggccat | 60 |
| gagtttgaca | tgaggggtaa | aggcaccggt | aacccaaatg | acggttatga | ggaccttgac | 120 |
| ctgaagtcca | ccaaggatga | ccttccattc | tccccctgga | tcctggtcca | aaacatcggg | 180 |
| tacggcttta | accagtacct | gccctacccc | gacggagcga | tgtcgccttt | tcaggctgcc | 240 |
| atgtacaatg | gctccgggta | ccacgtccat | cgtgaaatgg | ggtttgaaga | cggtgccacg | 300 |
| gtgactggca | tctaccgcta | cacctacgag | ggaagccaca | tcaaaggaga | gtttcaggtg | 360 |
| gatgggaccg | gattccctgc | tgacggccct | gtgatgacca | actcgctcac | tgatcaggac | 420 |
| tggtccgtga | ccaagatgat | gtaccttgat | aacaaaaccg | tcactagcac | cgctgaccag | 480 |
| acctacacca | ctgcaagtgg | caagcgctac | cagggcacag | tgcggaccaa | caacaccttt | 540 |
| gccaagccga | tagcggccaa | catcctgcag | aagcagccgg | tattcgtgtc | ccgcaagc | 598 |

<210> SEQ ID NO 65
<211> LENGTH: 595
<212> TYPE: DNA
<213> ORGANISM: Branchiostoma lanceolatum

<400> SEQUENCE: 65

| | | | | | |
|---|---|---|---|---|---|
| aacaacatgt | ctctccctaa | gacccacgag | ttgcatattt | ttggcaaaat | caatggccat | 60 |
| gagtacgaca | tgaggggtaa | aggcacaggt | aacccaaatg | acggttatga | ggaccttgac | 120 |
| ctgaagtcca | aggatgacct | tccattctcc | cctggatcc | tggttcaaaa | catcggatac | 180 |
| ggctttaacc | agtacctgcc | ctaccccgac | ggagcgatgt | cgcctttcca | ggctgccatg | 240 |
| tgcgatggct | ccgggtacga | ggtccatcgt | gaaatggagt | ttgaagacgg | tgccacgctg | 300 |
| actggcatct | accgctacac | ctacgaggga | agcacatca | aaggagagtt | tcaggtggat | 360 |
| gggaccggtt | tccctgatga | cggccctgtg | atgaccgact | cgctcaccga | tctggactgg | 420 |

```
gtcgtgacca agatggtgta tcccgacgag aaaaccgtct tcagcacctc cgaccagacc    480
tacaccactg caagtggcaa gggttacaag agtacagtgc ggaccaacaa cattttttgcc    540 aagccaatgg cggccgacat gatgcagaac cagccgatat cgtgtcccg caagc          595
```

<210> SEQ ID NO 66
<211> LENGTH: 598
<212> TYPE: DNA
<213> ORGANISM: Branchiostoma lanceolatum

<400> SEQUENCE: 66

```
acaactatgt ctctcccagc gacccatgag ttgcacattt ttggcaaaat caatggccat     60
gagtacgaca tgaggggtaa aggcactggt aacccaaatg acggttatga ggaccttgac    120
ctgaagtcca ccaaggatga ccttccattc tcccccctgga tcctggtcca aaacatcggg    180
tacggcttta accagtactt gccctacccc gacggagcga tgtcgccttt ccaggctgcc    240
atgtgcgatg gctccgggta cgaggtccat cgtgaaatgg agtttgaaga cggtgccacg    300
gtgactggta tctaccgcta cacctacgag ggaagccaca tcaaggaga gtttcaggtg    360 gatgggaccg gtttccctga tgacggcct gtgatgaccg actcgctcac tgatctggac    420
tgggtcgtga ccaagatggt gtaccccgac gagaaaaccg tcttcagcac ctccgaccag    480
acctacacca ctacaagtgg caagggctac aagagcacag tgcggaccaa caacattttt    540
gccaagccaa tagcggccga catgatgcag agccagccgg tattcgtgtc ccgcaagc     598
```

<210> SEQ ID NO 67
<211> LENGTH: 598
<212> TYPE: DNA
<213> ORGANISM: Branchiostoma lanceolatum

<400> SEQUENCE: 67

```
acaaccatgt ctctcccagc gacccatgag ttgcacattt ttggcaaaat caatggccat     60
gagtttgaca tgaggggtaa aggcaccggt aacccaaatg acggttatga ggaccttgac    120
ctgaagtcca ccaaggatga ccttccattc tcccccctgga tcctggtcca aaacatcggg    180
tacggcttta accagtacct gccctacccc gacggagcga tgtcgccttt ccaggctgcc    240
atgtacaatg gctccgggta ccacgtccat cgtgaaatgg agtttgaaga cggtgccacg    300
ctgactggca tctaccgcta cacctacgag ggaagccaca tcaaggaga gtttcaggtg    360 gatgggaccg gtttccctgc tgacggcct gtgatgaccg actcgctcac tgatctggac    420
tgggtcgtga caagatggt gtatcccgac gacaaaaccg tcttcagcac ctctgaccag    480
acctacacca ctacaagtgg caagggctac agagcacag tgcggaccaa caacattttt    540
gccgagccga tagcggccga catgatgcag agccagccgg tattcgtgtc ccgcaagc     598
```

<210> SEQ ID NO 68
<211> LENGTH: 220
<212> TYPE: PRT
<213> ORGANISM: Branchiostoma lanceolatum

<400> SEQUENCE: 68

```
Met Pro Leu Pro Ala Thr His Glu Leu His Ile Phe Gly Ser Ile Asn
1               5                   10                  15

Ser Leu Glu Phe Asp Leu Val Gly Arg Gly Thr Gly Asn Pro Lys Glu
            20                  25                  30

Gly Tyr Glu Glu Leu His Leu Lys Ser Thr Lys Ser Ala Leu Gln Phe
        35                  40                  45

Ser Pro Trp Ile Leu Val Pro Gln Ile Gly Tyr Gly Phe Tyr Gln Tyr
```

```
            50                  55                  60
Leu Pro Phe Pro Asp Gly Ala Met Ser Pro Phe Gln Ala Ala Met Asn
 65                  70                  75                  80

Asp Gly Ser Gly Tyr Gln Val His Arg Thr Met Gln Phe Glu Asp Gly
                 85                  90                  95

Ala Thr Leu Thr Gly Ile Tyr Arg Tyr Thr Tyr Glu Gly Thr His Ile
                100                 105                 110

Lys Gly Glu Phe Gln Val Ile Gly Thr Gly Phe Pro Ala Asp Gly Pro
            115                 120                 125

Val Met Thr Asn Ser Leu Thr Ala Ala Asp Trp Cys Val Thr Lys Ile
130                 135                 140

Val Tyr Pro Asn Glu Asn Thr Ile Ile Asp Lys Phe Asp Trp Thr Tyr
145                 150                 155                 160

Thr Thr Thr Ser Gly Lys Arg Tyr Gln Ser Asn Val Arg Ser Asn Phe
                165                 170                 175

Thr Phe Ala Lys Pro Ile Ala Ala Asn Ile Leu Gln Lys Gln Pro Met
            180                 185                 190

Phe Val Phe Arg Lys Thr Glu Leu Lys His Ser Lys Thr Glu Leu Asn
            195                 200                 205

Phe Lys Glu Trp Gln Thr Ala Phe Ser Asp Val Met
210                 215                 220

<210> SEQ ID NO 69
<211> LENGTH: 220
<212> TYPE: PRT
<213> ORGANISM: Branchiostoma lanceolatum

<400> SEQUENCE: 69

Met Ser Leu Pro Ala Thr His Glu Leu His Ile Phe Gly Ser Ile Asn
  1               5                  10                  15

Ser Leu Glu Phe Asp Leu Val Gly Arg Gly Thr Gly Asn Pro Arg Glu
                 20                  25                  30

Gly Tyr Glu Glu Leu His Leu Lys Ser Thr Lys Ser Ala Leu Gln Phe
             35                  40                  45

Ser Pro Trp Ile Leu Val Pro Gln Ile Gly Tyr Gly Phe Tyr Gln Tyr
 50                  55                  60

Leu Pro Phe Pro Asp Gly Ala Met Ser Pro Phe Gln Ala Ala Met Asn
 65                  70                  75                  80

Asp Gly Ser Gly Tyr Gln Val His Arg Thr Met Gln Phe Glu His Gly
                 85                  90                  95

Ala Thr Leu Thr Gly Ile Tyr Arg Tyr Thr Tyr Glu Gly Thr His Ile
                100                 105                 110

Lys Gly Glu Phe Gln Val Ile Gly Thr Gly Phe Pro Ala Asp Gly Pro
            115                 120                 125

Val Met Thr Asn Ser Leu Thr Ala Ala Asp Trp Cys Val Thr Lys Ile
130                 135                 140

Val Tyr Pro Asn Glu Asn Thr Ile Ile Asp Lys Phe Asp Trp Thr Tyr
145                 150                 155                 160

Thr Thr Thr Ser Gly Lys Arg Tyr His Ser Asn Val Arg Ser Asn Phe
                165                 170                 175

Thr Phe Ala Lys Pro Ile Ala Ala Asn Ile Leu Gln Lys Gln Pro Met
            180                 185                 190

Phe Val Phe Arg Lys Thr Glu Leu Lys His Ser Lys Thr Glu Leu Asn
            195                 200                 205

Phe Lys Glu Trp Gln Thr Ala Phe Gly Asp Val Met
```

-continued

```
              210                 215                 220
```

<210> SEQ ID NO 70
<211> LENGTH: 219
<212> TYPE: PRT
<213> ORGANISM: Branchiostoma lanceolatum

<400> SEQUENCE: 70

```
Met Ser Leu Pro Ala Thr His Glu Leu His Ile Phe Gly Ser Phe Asn
1               5                   10                  15

Gly Val Asp Phe Asp Met Val Gly Arg Gly Thr Gly Asn Pro Asn Asp
                20                  25                  30

Gly Tyr Glu Glu Leu Asn Leu Lys Ser Thr Lys Gly Ala Leu Gln Phe
            35                  40                  45

Ser Pro Trp Ile Leu Val Pro Gln Ile Gly Tyr Gly Phe His Gln Tyr
        50                  55                  60

Leu Pro Phe Pro Asp Gly Met Ser Pro Phe Gln Ala Ala Met Lys Asp
65                  70                  75                  80

Gly Ser Gly Tyr Gln Val His Arg Thr Met Gln Phe Glu Asp Gly Ala
                85                  90                  95

Ser Leu Thr Ser Asn Tyr Arg Tyr Thr Tyr Glu Gly Ser His Ile Lys
            100                 105                 110

Gly Glu Phe Gln Val Ile Gly Thr Gly Phe Pro Ala Asp Gly Pro Val
        115                 120                 125

Met Thr Asn Ser Leu Thr Ala Ala Asp Trp Cys Val Thr Lys Met Leu
130                 135                 140

Tyr Pro Asn Asp Lys Thr Ile Ile Ser Thr Phe Asp Trp Thr Tyr Thr
145                 150                 155                 160

Thr Gly Ser Gly Lys Arg Tyr Gln Ser Thr Val Arg Thr Asn Tyr Thr
                165                 170                 175

Phe Ala Lys Pro Met Ala Ala Asn Ile Leu Lys Asn Gln Pro Met Phe
            180                 185                 190

Val Phe Arg Lys Thr Glu Leu Lys His Ser Lys Thr Glu Leu Asn Phe
        195                 200                 205

Lys Glu Trp Gln Lys Ala Phe Thr Asp Val Met
    210                 215
```

<210> SEQ ID NO 71
<211> LENGTH: 219
<212> TYPE: PRT
<213> ORGANISM: Branchiostoma lanceolatum

<400> SEQUENCE: 71

```
Met Pro Leu Pro Ala Thr His Glu Leu His Ile Phe Gly Ser Phe Asn
1               5                   10                  15

Gly Val Asp Phe Asp Met Val Gly Arg Gly Thr Gly Asn Pro Asn Asp
                20                  25                  30

Gly Tyr Glu Glu Leu Asn Leu Lys Ser Thr Lys Gly Ala Leu Gln Phe
            35                  40                  45

Ser Pro Trp Ile Leu Val Pro Gln Ile Gly Tyr Gly Phe His Gln Tyr
        50                  55                  60

Leu Pro Phe Pro Asp Gly Met Ser Pro Phe Gln Ala Ala Met Lys Asp
65                  70                  75                  80

Gly Ser Gly Tyr Gln Val His Arg Thr Met Gln Phe Glu Asp Gly Ala
                85                  90                  95

Ser Leu Thr Ser Asn Tyr Arg Tyr Thr Tyr Glu Gly Ser His Ile Lys
            100                 105                 110
```

Gly Glu Phe Gln Val Ile Gly Thr Gly Phe Pro Ala Asp Gly Pro Val
            115                 120                 125

Met Thr Asn Ser Leu Thr Thr Ala Asp Trp Cys Val Thr Lys Met Leu
    130                 135                 140

Tyr Pro Asn Asp Lys Thr Ile Ile Ser Thr Phe Asp Trp Thr Tyr Asn
145                 150                 155                 160

Thr Ala Ser Gly Lys Arg Tyr Gln Ser Thr Val Arg Thr Asn Tyr Thr
                165                 170                 175

Phe Asn Lys Pro Met Ala Ala Asn Ile Leu Lys Asn Gln Pro Met Phe
            180                 185                 190

Val Phe Arg Lys Thr Glu Leu Lys His Ser Lys Thr Glu Leu Asn Phe
        195                 200                 205

Lys Glu Trp Gln Met Ala Phe Ala Asp Val Met
        210                 215

<210> SEQ ID NO 72
<211> LENGTH: 219
<212> TYPE: PRT
<213> ORGANISM: Branchiostoma lanceolatum

<400> SEQUENCE: 72

Met Pro Leu Pro Ala Thr His Glu Leu His Ile Phe Gly Ser Phe Asn
1               5                   10                  15

Gly Val Asp Phe Asp Met Val Gly His Gly Thr Gly Asn Pro Asn Asp
            20                  25                  30

Gly Tyr Glu Glu Leu Asn Leu Lys Ser Thr Lys Gly Ala Leu Gln Phe
        35                  40                  45

Ser Pro Trp Ile Leu Val Pro Gln Ile Gly Tyr Gly Phe His Gln Tyr
    50                  55                  60

Leu Pro Phe Pro Asp Gly Met Ser Pro Phe Gln Ala Ala Met Lys Asp
65                  70                  75                  80

Gly Ser Gly Tyr Gln Val His Arg Thr Met Gln Phe Glu Asp Gly Ala
                85                  90                  95

Ser Leu Thr Ser Asn Tyr Arg Tyr Thr Tyr Glu Gly Ser His Ile Lys
            100                 105                 110

Gly Glu Phe Gln Val Asn Gly Thr Gly Phe Pro Ala Asp Gly Pro Val
        115                 120                 125

Met Thr Asn Ser Leu Thr Thr Ala Asp Trp Cys Val Thr Lys Met Leu
    130                 135                 140

Tyr Pro Asn Asp Lys Thr Ile Ile Ser Thr Phe Asp Trp Thr Tyr Thr
145                 150                 155                 160

Thr Gly Ser Gly Lys Arg Tyr Gln Ser Thr Val Arg Thr Asn Tyr Thr
                165                 170                 175

Phe Ala Lys Pro Met Ala Ala Asn Ile Leu Gln Asn Gln Pro Met Phe
            180                 185                 190

Val Phe Arg Lys Thr Glu Leu Lys His Ser Lys Thr Glu Leu Asn Phe
        195                 200                 205

Lys Glu Trp Gln Lys Ala Phe Ala Asp Val Met
        210                 215

<210> SEQ ID NO 73
<211> LENGTH: 220
<212> TYPE: PRT
<213> ORGANISM: Branchiostoma lanceolatum

<400> SEQUENCE: 73

Met Ser Leu Pro Ala Thr His Glu Leu His Ile Phe Gly Ser Ile Asn
1               5                   10                  15

Ser Leu Glu Phe Asp Leu Val Gly Arg Gly Thr Gly Asn Pro Lys Glu
            20                  25                  30

Gly Tyr Glu Glu Leu His Leu Lys Ser Thr Lys Ser Ala Leu Gln Phe
        35                  40                  45

Ser Pro Trp Ile Leu Val Pro Gln Ile Gly Tyr Gly Phe Tyr Gln Tyr
    50                  55                  60

Leu Pro Phe Pro Asp Gly Ala Met Ser Pro Phe Gln Ala Ala Met Asn
65                  70                  75                  80

Asp Gly Ser Gly Tyr Gln Val His Arg Thr Met Gln Phe Glu Asp Gly
                85                  90                  95

Ala Thr Leu Thr Gly Ile Tyr Arg Tyr Thr Tyr Glu Gly Thr His Ile
            100                 105                 110

Lys Gly Glu Phe Gln Val Ile Gly Thr Gly Phe Pro Ala Asp Gly Pro
        115                 120                 125

Val Met Thr Asn Ser Leu Thr Ala Ala Asp Trp Cys Val Thr Lys Ile
    130                 135                 140

Val Tyr Pro Asn Glu Asn Thr Ile Ile Asp Lys Phe Asp Trp Thr Tyr
145                 150                 155                 160

Thr Thr Thr Ser Gly Lys Arg Tyr Gln Ser Asn Val Arg Ser Asn Phe
                165                 170                 175

Thr Phe Ala Lys Pro Ile Ala Ala Asn Ile Leu Gln Lys Gln Pro Met
            180                 185                 190

Phe Val Phe Arg Lys Thr Glu Leu Lys His Ser Lys Thr Glu Leu Asn
        195                 200                 205

Phe Lys Glu Trp Gln Thr Ala Phe Ser Asp Val Met
    210                 215                 220

<210> SEQ ID NO 74
<211> LENGTH: 219
<212> TYPE: PRT
<213> ORGANISM: Branchiostoma lanceolatum

<400> SEQUENCE: 74

Met Pro Leu Pro Ala Thr His Glu Leu His Ile Phe Gly Ser Phe Asn
1               5                   10                  15

Gly Val Glu Phe Asp Met Val Gly Arg Gly Thr Gly Asn Pro Asn Asp
            20                  25                  30

Gly Ser Glu Asp Leu His Leu Lys Ser Thr Lys Gly Ala Leu Gln Phe
        35                  40                  45

Ser Pro Trp Ile Leu Ile Pro His Ile Gly Tyr Gly Phe His Gln Tyr
    50                  55                  60

Leu Pro Phe Pro Asp Gly Met Ser Pro Phe Gln Ala Ala Met Gln Asp
65                  70                  75                  80

Gly Ser Gly Tyr Gln Val His Arg Thr Met Gln Phe Glu Asp Gly Ala
                85                  90                  95

Ser Leu Thr Ala Asn Phe Arg Tyr Thr Tyr Glu Gly Ser His Ile Lys
            100                 105                 110

Gly Glu Phe Gln Val Ile Gly Ser Gly Phe Pro Ala Asp Gly Pro Val
        115                 120                 125

Met Thr Asn Ser Leu Thr Ala Val Asp Trp Cys Val Ala Lys Met Leu
    130                 135                 140

Tyr Pro Asn Asp Lys Thr Ile Ile Ser Thr Phe Asp Trp Thr Tyr Thr
145                 150                 155                 160

```
Thr Gly Ser Gly Lys Arg Tyr Gln Ser Thr Val Arg Thr Asn Tyr Thr
            165                 170                 175

Phe Ala Lys Pro Met Ala Ala Asn Ile Leu Lys Asn Gln Pro Met Phe
            180                 185                 190

Val Phe Arg Lys Thr Glu Leu Lys His Ser Lys Thr Glu Leu Asn Phe
            195                 200                 205

Lys Glu Trp Gln Lys Ala Phe Ala Asp Val Met
            210                 215

<210> SEQ ID NO 75
<211> LENGTH: 220
<212> TYPE: PRT
<213> ORGANISM: Branchiostoma lanceolatum

<400> SEQUENCE: 75

Met Pro Leu Pro Ala Thr His Asp Leu His Ile Ser Gly Ser Ile Asn
1               5                   10                  15

Gly His Glu Phe Asp Leu Glu Gly Ser Gly Lys Gly Asn Glu Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Thr Gly Tyr Gly Phe Tyr Gln Tyr
50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Ser Met Gln Phe Glu Asp Gly
            85                  90                  95

Ala Met Leu His Ser Asp His Arg Tyr Ile Tyr Lys Gly Asn His Ile
            100                 105                 110

Lys Gly Glu Phe Arg Leu Thr Gly Ser Gly Phe Pro Ala Asp Gly Pro
        115                 120                 125

Val Met Thr Asn Ser Leu Thr Ala Ala Asp Trp Cys Val Asp Lys Leu
        130                 135                 140

Leu Tyr Pro Asn Asp Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
            165                 170                 175

Thr Phe Gly Lys Pro Ile Ala Ala Asp Ile Leu Lys Lys Gln Pro Met
            180                 185                 190

Phe Val Phe Arg Met Met Glu Leu Lys His Thr Lys Thr Glu Leu Asn
            195                 200                 205

Phe Lys Gln Trp Gln Lys Ala Phe Gln Asp Ile Ala
            210                 215                 220

<210> SEQ ID NO 76
<211> LENGTH: 220
<212> TYPE: PRT
<213> ORGANISM: Branchiostoma lanceolatum

<400> SEQUENCE: 76

Met Pro Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Arg Gly Asp Leu Ser Phe
        35                  40                  45

Ser Pro Trp Ile Leu Val Pro Asn Ile Gly Tyr Gly Phe Tyr Gln Tyr
```

```
                50                  55                  60
Leu Pro Phe Pro Asp Gly Ala Met Ser Pro Tyr Gln Ala Ala Met His
 65                  70                  75                  80

Asp Gly Ser Gly Tyr Val Met His Arg Thr Met Gln Phe Glu Asp Gly
                 85                  90                  95

Ala Met Leu His Ser Asp His Arg Tyr Thr Tyr Lys Gly Asn His Ile
                100                 105                 110

Lys Gly Glu Phe Arg Leu Thr Gly Ser Gly Phe Pro Ala Asp Gly Pro
                115                 120                 125

Val Met Thr Asn Ser Leu Thr Ala Ala Asp Trp Cys Val Asp Lys Leu
                130                 135                 140

Leu Tyr Pro Thr Glu Asn Thr Leu Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Ala Lys Pro Met Ala Ala Asp Ile Leu Lys Lys Gln Pro Met
                180                 185                 190

Phe Val Phe Arg Lys Val Glu Leu Lys His Thr Lys Thr Glu Leu Asn
                195                 200                 205

Phe Lys Gln Trp Gln Lys Ala Phe Gln Asp Ile Val
210                 215                 220

<210> SEQ ID NO 77
<211> LENGTH: 220
<212> TYPE: PRT
<213> ORGANISM: Branchiostoma lanceolatum

<400> SEQUENCE: 77

Met Ser Leu Pro Ala Thr His Asp Leu His Ile Ser Gly Ser Ile Asn
  1               5                  10                  15

Gly His Glu Phe Asp Leu Glu Gly Ser Gly Lys Gly Asn Ala Lys Glu
                 20                  25                  30

Gly Tyr Gln Glu Leu His Leu Lys Ser Asn Lys Gly Asp Leu Ser Phe
                 35                  40                  45

Ser Pro Trp Ile Leu Val Pro Asn Ile Gly Tyr Gly Phe Tyr Gln Tyr
 50                  55                  60

Leu Pro Phe Pro Asp Gly Ala Met Ser Pro Tyr Gln Ala Ala Met His
 65                  70                  75                  80

Asp Gly Ser Gly Tyr Val Met His Arg Ser Met Gln Phe Glu Asp Gly
                 85                  90                  95

Ala Met Leu His Ser Asp His Arg Tyr Ile Tyr Lys Gly Asn His Ile
                100                 105                 110

Lys Gly Glu Phe Arg Leu Thr Gly Ser Gly Phe Pro Ala Asp Gly Pro
                115                 120                 125

Val Met Thr Asn Ser Leu Thr Ala Ala Asp Trp Cys Val Asp Lys Leu
                130                 135                 140

Leu Tyr Pro Asn Asp Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Gly Lys Pro Ile Ala Ala Asp Ile Leu Lys Lys Gln Pro Met
                180                 185                 190

Phe Val Phe Arg Lys Val Glu Leu Lys His Thr Lys Thr Glu Leu Asn
                195                 200                 205

Phe Lys Gln Trp Gln Lys Ala Phe Gln Asp Ile Ala
```

210                 215                 220

<210> SEQ ID NO 78
<211> LENGTH: 220
<212> TYPE: PRT
<213> ORGANISM: Branchiostoma lanceolatum

<400> SEQUENCE: 78

Met Ser Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Thr Met Gln Phe Glu Asp Gly
                85                  90                  95

Ala Met Leu His Ser Asp His Arg Tyr Thr Tyr Lys Gly Asn His Ile
            100                 105                 110

Lys Gly Glu Phe Arg Leu Thr Gly Ser Gly Phe Pro Ala Asp Gly Pro
        115                 120                 125

Val Met Thr Asn Ser Leu Thr Ala Val Asp Trp Cys Val Asp Lys Leu
    130                 135                 140

Leu Tyr Pro Asn Glu Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Ala Lys Pro Ile Ala Ala Asp Ile Leu Lys Lys Gln Pro Met
            180                 185                 190

Phe Val Phe Arg Lys Val Glu Leu Lys His Ser Lys Thr Glu Leu Asn
        195                 200                 205

Phe Lys Gln Trp Gln Lys Ala Phe Gln Asp Ile Val
    210                 215                 220

<210> SEQ ID NO 79
<211> LENGTH: 220
<212> TYPE: PRT
<213> ORGANISM: Branchiostoma lanceolatum

<400> SEQUENCE: 79

Met Ser Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Ser Met Gln Phe Glu Asp Gly
                85                  90                  95

Ala Met Leu His Ser Asp His Arg Tyr Ile Tyr Lys Gly Asn His Ile
            100                 105                 110

```
Lys Gly Glu Phe Arg Leu Thr Gly Ser Gly Phe Pro Ala Asp Gly Pro
        115                 120                 125

Val Met Thr Asn Ser Leu Thr Ala Ala Asp Trp Cys Val Asp Lys Leu
    130                 135                 140

Leu Tyr Pro Asn Asp Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Gly Lys Pro Ile Ala Ala Asp Ile Leu Lys Lys Gln Pro Met
            180                 185                 190

Phe Val Phe Arg Lys Val Glu Leu Lys His Thr Lys Thr Glu Leu Asn
        195                 200                 205

Phe Lys Gln Trp Gln Lys Ala Phe Gln Asp Ile Ala
    210                 215                 220

<210> SEQ ID NO 80
<211> LENGTH: 220
<212> TYPE: PRT
<213> ORGANISM: Branchiostoma lanceolatum

<400> SEQUENCE: 80

Met Ser Leu Pro Lys Thr His Asp Leu His Ile Ser Gly Ser Val Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Arg Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Ala Met Arg Phe Glu Asp Gly
                85                  90                  95

Ala Met Leu His Ser Asp His Arg Tyr Thr Tyr Asn Gly Asn Asn Ile
            100                 105                 110

Lys Gly Glu Phe Arg Leu Thr Gly Ser Gly Phe Pro Ala Asp Gly Pro
        115                 120                 125

Val Met Thr Asn Ser Leu Thr Ala Ala Asp Trp Cys Val Asp Lys Leu
    130                 135                 140

Leu Tyr Pro Asn Glu Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Gly Lys Pro Ile Ser Ala Asp Ile Leu Lys Lys Gln Pro Met
            180                 185                 190

Phe Val Phe Arg Lys Val Glu Leu Lys His Ser Lys Thr Glu Leu Asn
        195                 200                 205

Phe Lys Gln Trp Gln Lys Ala Phe Gln Asp Ile Val
    210                 215                 220

<210> SEQ ID NO 81
<211> LENGTH: 220
<212> TYPE: PRT
<213> ORGANISM: Branchiostoma lanceolatum

<400> SEQUENCE: 81
```

```
Met Pro Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65              70                  75                  80

Asp Gly Ser Gly Tyr Val Met His Arg Ala Met Arg Phe Glu Asp Gly
                85                  90                  95

Ala Met Leu His Ser Asp His Arg Tyr Thr Tyr Asn Gly Asn His Ile
                100                 105                 110

Lys Gly Glu Phe Arg Leu Thr Gly Ser Gly Phe Pro Ala Asp Gly Pro
            115                 120                 125

Val Met Thr Asn Ser Leu Thr Ala Ala Asp Trp Cys Val Asp Lys Leu
    130                 135                 140

Leu Tyr Pro Asp Glu Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Ala Lys Pro Ile Ser Ala Asp Ile Leu Lys Lys Gln Pro Met
            180                 185                 190

Phe Val Phe Arg Lys Val Glu Leu Lys His Ser Lys Thr Glu Leu Asn
        195                 200                 205

Phe Lys Gln Trp Gln Lys Ala Phe Gln Asp Ile Val
    210                 215                 220

<210> SEQ ID NO 82
<211> LENGTH: 220
<212> TYPE: PRT
<213> ORGANISM: Branchiostoma lanceolatum

<400> SEQUENCE: 82

Met Ser Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65              70                  75                  80

Asp Gly Ser Gly Tyr Val Met His Arg Ala Met Arg Phe Glu Asp Gly
                85                  90                  95

Ala Met Leu His Ser Asp His Arg Tyr Thr Tyr Asn Gly Asn His Ile
                100                 105                 110

Lys Gly Glu Phe Arg Leu Thr Gly Ser Gly Phe Pro Ala Asp Gly Pro
            115                 120                 125

Val Met Thr Asn Ser Leu Thr Ala Ala Asp Trp Cys Val Asp Lys Leu
    130                 135                 140

Leu Tyr Pro Asp Glu Asn Thr Ile Ile Gly Lys Phe Asp Trp Thr Tyr
145                 150                 155                 160
```

```
Thr Thr Thr Ser Gly Lys Arg Tyr Gln Ser Asp Val Gln Thr Asn Val
            165                 170                 175

Thr Phe Ala Lys Pro Ile Ser Ala Asp Ile Leu Lys Lys Gln Pro Met
        180                 185                 190

Phe Val Phe Arg Lys Val Glu Leu Lys His Ser Lys Thr Glu Leu Asn
    195                 200                 205

Phe Lys Gln Trp Gln Lys Ala Phe Gln Asp Ile Val
    210                 215                 220

<210> SEQ ID NO 83
<211> LENGTH: 220
<212> TYPE: PRT
<213> ORGANISM: Branchiostoma lanceolatum

<400> SEQUENCE: 83

Met Ser Leu Pro Lys Thr His Asp Leu His Ile Ser Gly Ser Val Asn
1               5                   10                  15

Gly His Glu Phe Asp Leu Glu Gly Ser Gly Lys Gly Asp Ala Lys Glu
            20                  25                  30

Gly Tyr Gln Glu Leu His Leu Lys Ser Asn Arg Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Ala Met Arg Phe Glu Asp Gly
                85                  90                  95

Ala Met Leu His Ser Asp His Arg Tyr Thr Tyr Asn Gly Asn Asn Ile
            100                 105                 110

Lys Gly Glu Phe Arg Leu Thr Gly Ser Gly Phe Pro Ala Asp Gly Pro
        115                 120                 125

Val Met Thr Asn Ser Leu Thr Ala Ala Asp Trp Cys Val Asp Lys Leu
    130                 135                 140

Leu Tyr Pro Asn Glu Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Gly Lys Pro Ile Ser Ala Asp Ile Leu Lys Lys Gln Pro Met
            180                 185                 190

Phe Val Phe Arg Lys Val Glu Leu Lys His Ser Lys Thr Glu Leu Asn
        195                 200                 205

Phe Lys Gln Trp Gln Lys Ala Phe Gln Asp Ile Val
    210                 215                 220

<210> SEQ ID NO 84
<211> LENGTH: 197
<212> TYPE: PRT
<213> ORGANISM: Branchiostoma lanceolatum

<400> SEQUENCE: 84

Met Ser Leu Pro Ala Thr His Glu Leu His Ile Phe Asp Lys Ile Asn
1               5                   10                  15

Gly His Glu Phe Asp Met Arg Gly Lys Gly Thr Gly Asn Pro Asn Asp
            20                  25                  30

Gly Tyr Glu Asp Leu Asp Leu Lys Ser Thr Lys Asp Asp Leu Pro Phe
        35                  40                  45

Ser Pro Trp Ile Leu Val Gln Asn Ile Gly Tyr Gly Phe Asn Gln Tyr
```

```
                    50                  55                  60
Leu Pro Tyr Pro Asp Gly Ala Met Ser Pro Phe Gln Ala Ala Met Tyr
 65                  70                  75                  80

Asn Gly Ser Gly Tyr His Val His Arg Glu Met Gly Phe Glu Asp Gly
                     85                  90                  95

Ala Thr Val Thr Gly Ile Tyr Arg Tyr Thr Tyr Glu Gly Ser His Ile
                    100                 105                 110

Lys Gly Glu Phe Gln Val Asp Gly Thr Gly Phe Pro Ala Asp Gly Pro
                115                 120                 125

Val Met Thr Asn Ser Leu Thr Asp Gln Asp Trp Ser Val Thr Lys Met
            130                 135                 140

Met Tyr Leu Asp Asn Lys Thr Val Thr Ser Thr Ala Asp Gln Thr Tyr
145                 150                 155                 160

Thr Thr Ala Ser Gly Lys Arg Tyr Gln Gly Thr Val Arg Thr Asn Asn
                165                 170                 175

Thr Phe Ala Lys Pro Ile Ala Ala Asn Ile Leu Gln Lys Gln Pro Val
            180                 185                 190

Phe Val Ser Arg Lys
            195

<210> SEQ ID NO 85
<211> LENGTH: 196
<212> TYPE: PRT
<213> ORGANISM: Branchiostoma lanceolatum

<400> SEQUENCE: 85

Met Ser Leu Pro Lys Thr His Glu Leu His Ile Phe Gly Lys Ile Asn
  1               5                  10                  15

Gly His Glu Tyr Asp Met Arg Gly Lys Gly Thr Gly Asn Pro Asn Asp
             20                  25                  30

Gly Tyr Glu Asp Leu Asp Leu Lys Ser Lys Asp Asp Leu Pro Phe Ser
         35                  40                  45

Pro Trp Ile Leu Val Gln Asn Ile Gly Tyr Gly Phe Asn Gln Tyr Leu
 50                  55                  60

Pro Tyr Pro Asp Gly Ala Met Ser Pro Phe Gln Ala Ala Met Cys Asp
 65                  70                  75                  80

Gly Ser Gly Tyr Glu Val His Arg Glu Met Glu Phe Glu Asp Gly Ala
                 85                  90                  95

Thr Leu Thr Gly Ile Tyr Arg Tyr Thr Tyr Glu Gly Ser His Ile Lys
                100                 105                 110

Gly Glu Phe Gln Val Asp Gly Thr Gly Phe Pro Asp Asp Gly Pro Val
            115                 120                 125

Met Thr Asp Ser Leu Thr Asp Leu Asp Trp Val Val Thr Lys Met Val
        130                 135                 140

Tyr Pro Asp Glu Lys Thr Val Phe Ser Thr Ser Asp Gln Thr Tyr Thr
145                 150                 155                 160

Thr Ala Ser Gly Lys Gly Tyr Lys Ser Thr Val Arg Thr Asn Asn Ile
                165                 170                 175

Phe Ala Lys Pro Met Ala Ala Asp Met Met Gln Asn Gln Pro Ile Phe
            180                 185                 190

Val Ser Arg Lys
            195

<210> SEQ ID NO 86
<211> LENGTH: 197
<212> TYPE: PRT
```

<213> ORGANISM: Branchiostoma lanceolatum

<400> SEQUENCE: 86

```
Met Ser Leu Pro Ala Thr His Glu Leu His Ile Phe Gly Lys Ile Asn
1               5                   10                  15
Gly His Glu Tyr Asp Met Arg Gly Lys Gly Thr Gly Asn Pro Asn Asp
            20                  25                  30
Gly Tyr Glu Asp Leu Asp Leu Lys Ser Thr Lys Asp Asp Leu Pro Phe
        35                  40                  45
Ser Pro Trp Ile Leu Val Gln Asn Ile Gly Tyr Gly Phe Asn Gln Tyr
    50                  55                  60
Leu Pro Tyr Pro Asp Gly Ala Met Ser Pro Phe Gln Ala Ala Met Cys
65                  70                  75                  80
Asp Gly Ser Gly Tyr Glu Val His Arg Glu Met Glu Phe Glu Asp Gly
                85                  90                  95
Ala Thr Val Thr Gly Ile Tyr Arg Tyr Thr Tyr Glu Gly Ser His Ile
            100                 105                 110
Lys Gly Glu Phe Gln Val Asp Gly Thr Gly Phe Pro Asp Asp Gly Pro
        115                 120                 125
Val Met Thr Asp Ser Leu Thr Asp Leu Asp Trp Val Thr Lys Met
    130                 135                 140
Val Tyr Pro Asp Glu Lys Thr Val Phe Ser Thr Ser Asp Gln Thr Tyr
145                 150                 155                 160
Thr Thr Thr Ser Gly Lys Gly Tyr Lys Ser Thr Val Arg Thr Asn Asn
                165                 170                 175
Ile Phe Ala Lys Pro Ile Ala Ala Asp Met Met Gln Ser Gln Pro Val
            180                 185                 190
Phe Val Ser Arg Lys
        195
```

<210> SEQ ID NO 87
<211> LENGTH: 197
<212> TYPE: PRT
<213> ORGANISM: Branchiostoma lanceolatum

<400> SEQUENCE: 87

```
Met Ser Leu Pro Ala Thr His Glu Leu His Ile Phe Gly Lys Ile Asn
1               5                   10                  15
Gly His Glu Phe Asp Met Arg Gly Lys Gly Thr Gly Asn Pro Asn Asp
            20                  25                  30
Gly Tyr Glu Asp Leu Asp Leu Lys Ser Thr Lys Asp Asp Leu Pro Phe
        35                  40                  45
Ser Pro Trp Ile Leu Val Gln Asn Ile Gly Tyr Gly Phe Asn Gln Tyr
    50                  55                  60
Leu Pro Tyr Pro Asp Gly Ala Met Ser Pro Phe Gln Ala Ala Met Tyr
65                  70                  75                  80
Asn Gly Ser Gly Tyr His Val His Arg Glu Met Glu Phe Glu Asp Gly
                85                  90                  95
Ala Thr Leu Thr Gly Ile Tyr Arg Tyr Thr Tyr Glu Gly Ser His Ile
            100                 105                 110
Lys Gly Glu Phe Gln Val Asp Gly Thr Gly Phe Pro Ala Asp Gly Pro
        115                 120                 125
Val Met Thr Asp Ser Leu Thr Asp Leu Asp Trp Val Thr Lys Met
    130                 135                 140
Val Tyr Pro Asp Asp Lys Thr Val Phe Ser Thr Ser Asp Gln Thr Tyr
145                 150                 155                 160
```

-continued

```
Thr Thr Thr Ser Gly Lys Gly Tyr Gln Ser Thr Val Arg Thr Asn Asn
            165                 170                 175

Ile Phe Ala Glu Pro Ile Ala Ala Asp Met Met Gln Ser Gln Pro Val
        180                 185                 190

Phe Val Ser Arg Lys
        195

<210> SEQ ID NO 88
<211> LENGTH: 660
<212> TYPE: DNA
<213> ORGANISM: Branchiostoma lanceolatum
<220> FEATURE:
<221> NAME/KEY: mutation
<222> LOCATION: (356)..(357)
<223> OTHER INFORMATION: AA instead of CC in wild-type sequence

<400> SEQUENCE: 88
atgtctctcc cagcaaccca cgatttacac atctccggct caatcaatgg acatgagttt     60
gacttggaag gcagtggcaa gggcaatgca aaagaaggtt atcaggagct ccacctaaag    120
tccaacaagg gtgacctgtc attctccccc tggatcctgg tcccaaacat cggctacggc    180
ttctaccagt acctgccctt ccccgacgga gcgatgtcgc cttaccaggc cgccatgcac    240
gatggctccg gatacgtgat gcatcgttca atgcagtttg aggatggtgc catgctgcat    300
tcagaccacc gctacatcta aagggaaac catatcaaag gagagtttcg gctgaaagga    360
agcggtttcc ctgctgacgg ccctgtgatg accaactcgc tgaccgctgc ggactggtgc    420
gtcgacaagc tgctgtaccc aaacgacaac accataatcg gcaaattcga ctggacctac    480
accactacca gtggcaagcg ctaccaaagt gatgtgcaga ccaacgtcac atttggcaag    540
ccaatagcgg ccgacatttt gaagaagcag ccaatgttcg tgttccgcaa ggtggaactc    600
aagcacacca agactgagct caacttcaag cagtggcaga aggcattcca ggacatcgcc    660

<210> SEQ ID NO 89
<211> LENGTH: 660
<212> TYPE: DNA
<213> ORGANISM: Branchiostoma lanceolatum
<220> FEATURE:
<221> NAME/KEY: mutation
<222> LOCATION: (356)..(357)
<223> OTHER INFORMATION: AA instead of CC in wild-type sequence
<220> FEATURE:
<221> NAME/KEY: mutation
<222> LOCATION: (524)..(524)
<223> OTHER INFORMATION: C instead of A in wild-type sequence

<400> SEQUENCE: 89
atgtctctcc cagcaaccca cgatttacac atctccggct caatcaatgg acatgagttt     60
gacttggaag gcagtggcaa gggcaatgca aaagaaggtt atcaggagct ccacctaaag    120
tccaacaagg gtgacctgtc attctccccc tggatcctgg tcccaaacat cggctacggc    180
ttctaccagt acctgccctt ccccgacgga gcgatgtcgc cttaccaggc cgccatgcac    240
gatggctccg gatacgtgat gcatcgttca atgcagtttg aggatggtgc catgctgcat    300
tcagaccacc gctacatcta aagggaaac catatcaaag gagagtttcg gctgaaagga    360
agcggtttcc ctgctgacgg ccctgtgatg accaactcgc tgaccgctgc ggactggtgc    420
gtcgacaagc tgctgtaccc aaacgacaac accataatcg gcaaattcga ctggacctac    480
accactacca gtggcaagcg ctaccaaagt gatgtgcaga ccaccgtcac atttggcaag    540
ccaatagcgg ccgacatttt gaagaagcag ccaatgttcg tgttccgcaa ggtggaactc    600
```
aagcacacca agactgagct caacttcaag cagtggcaga aggcattcca ggacatcgcc    660

<210> SEQ ID NO 90
<211> LENGTH: 660
<212> TYPE: DNA
<213> ORGANISM: Branchiostoma lanceolatum
<220> FEATURE:
<221> NAME/KEY: mutation
<222> LOCATION: (356)..(357)
<223> OTHER INFORMATION: AA instead of CC in wild-type sequence
<220> FEATURE:
<221> NAME/KEY: mutation
<222> LOCATION: (469)..(469)
<223> OTHER INFORMATION: A instead of G in wild-type sequence
<220> FEATURE:
<221> NAME/KEY: mutation
<222> LOCATION: (471)..(471)
<223> OTHER INFORMATION: G instead of C in wild-type sequence
<220> FEATURE:
<221> NAME/KEY: mutation
<222> LOCATION: (524)..(524)
<223> OTHER INFORMATION: C instead of A in wild-type sequence

<400> SEQUENCE: 90
atgtctctcc cagcaaccca cgatttacac atctccggct caatcaatgg acatgagttt    60
gacttggaag gcagtggcaa gggcaatgca aagaaggtt atcaggagct ccacctaaag    120
tccaacaagg gtgacctgtc attctccccc tggatcctgg tcccaaacat cggctacggc    180
ttctaccagt acctgccctt ccccgacgga gcgatgtcgc cttaccaggc cgccatgcac    240
gatggctccg gatacgtgat gcatcgttca atgcagtttg aggatggtgc catgctgcat    300
tcagaccacc gctacatcta aagggaaac catatcaaag gagagtttcg gctgaaagga    360
agcggtttcc ctgctgacgg ccctgtgatg accaactcgc tgaccgctgc ggactggtgc    420
gtcgacaagc tgctgtaccc aaacgacaac accataatcg gcaaattcaa gtggacctac    480
accactacca gtggcaagcg ctaccaaagt gatgtgcaga ccaccgtcac atttggcaag    540
ccaatagcgg ccgacatttt gaagaagcag ccaatgttcg tgttccgcaa ggtggaactc    600
aagcacacca agactgagct caacttcaag cagtggcaga aggcattcca ggacatcgcc    660

<210> SEQ ID NO 91
<211> LENGTH: 220
<212> TYPE: PRT
<213> ORGANISM: Branchiostoma lanceolatum
<220> FEATURE:
<221> NAME/KEY: MUTAGEN
<222> LOCATION: (119)..(119)
<223> OTHER INFORMATION: Lys instead of Thr in wild-type sequence

<400> SEQUENCE: 91

Met Ser Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Ser Met Gln Phe Glu Asp Gly
                85                  90                  95

Ala Met Leu His Ser Asp His Arg Tyr Ile Tyr Lys Gly Asn His Ile
            100                 105                 110

```
Lys Gly Glu Phe Arg Leu Lys Gly Ser Gly Phe Pro Ala Asp Gly Pro
            115                 120                 125

Val Met Thr Asn Ser Leu Thr Ala Ala Asp Trp Cys Val Asp Lys Leu
        130                 135                 140

Leu Tyr Pro Asn Asp Asn Thr Ile Ile Gly Lys Phe Asp Trp Thr Tyr
145                 150                 155                 160

Thr Thr Thr Ser Gly Lys Arg Tyr Gln Ser Asp Val Gln Thr Asn Val
                165                 170                 175

Thr Phe Gly Lys Pro Ile Ala Ala Asp Ile Leu Lys Lys Gln Pro Met
            180                 185                 190

Phe Val Phe Arg Lys Val Glu Leu Lys His Thr Lys Thr Glu Leu Asn
        195                 200                 205

Phe Lys Gln Trp Gln Lys Ala Phe Gln Asp Ile Ala
            210                 215                 220

<210> SEQ ID NO 92
<211> LENGTH: 220
<212> TYPE: PRT
<213> ORGANISM: Branchiostoma lanceolatum
<220> FEATURE:
<221> NAME/KEY: MUTAGEN
<222> LOCATION: (119)..(119)
<223> OTHER INFORMATION: Lys in stead of Thr in wild-type sequence
<220> FEATURE:
<221> NAME/KEY: MUTAGEN
<222> LOCATION: (175)..(175)
<223> OTHER INFORMATION: Thr in stead of Asn in wild-type sequence

<400> SEQUENCE: 92

Met Ser Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Ile Gly Tyr Gly Phe Tyr Gln Tyr
    50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Ser Met Gln Phe Glu Asp Gly
                85                  90                  95

Ala Met Leu His Ser Asp His Arg Tyr Ile Tyr Lys Gly Asn His Ile
            100                 105                 110

Lys Gly Glu Phe Arg Leu Lys Gly Ser Gly Phe Pro Ala Asp Gly Pro
            115                 120                 125

Val Met Thr Asn Ser Leu Thr Ala Ala Asp Trp Cys Val Asp Lys Leu
        130                 135                 140

Leu Tyr Pro Asn Asp Asn Thr Ile Ile Gly Lys Phe Asp Trp Thr Tyr
145                 150                 155                 160

Thr Thr Thr Ser Gly Lys Arg Tyr Gln Ser Asp Val Gln Thr Thr Val
                165                 170                 175

Thr Phe Gly Lys Pro Ile Ala Ala Asp Ile Leu Lys Lys Gln Pro Met
            180                 185                 190

Phe Val Phe Arg Lys Val Glu Leu Lys His Thr Lys Thr Glu Leu Asn
        195                 200                 205

Phe Lys Gln Trp Gln Lys Ala Phe Gln Asp Ile Ala
            210                 215                 220
```

```
<210> SEQ ID NO 93
<211> LENGTH: 220
<212> TYPE: PRT
<213> ORGANISM: Branchiostoma lanceolatum
<220> FEATURE:
<221> NAME/KEY: MUTAGEN
<222> LOCATION: (119)..(119)
<223> OTHER INFORMATION: Lys instead of Thr in wild-type sequence
<220> FEATURE:
<221> NAME/KEY: MUTAGEN
<222> LOCATION: (157)..(157)
<223> OTHER INFORMATION: Lys instead of Asp in wild-type sequence
<220> FEATURE:
<221> NAME/KEY: MUTAGEN
<222> LOCATION: (175)..(175)
<223> OTHER INFORMATION: Thr instead of Asn in wild-type sequence

<400> SEQUENCE: 93

Met Ser Leu Pro Ala Thr His Asp Leu His Ile Ser Gly Ser Ile Asn
1               5                   10                  15

Gly His Glu Phe Asp Leu Glu Gly Ser Gly Lys Gly Asn Ala Lys Glu
            20                  25                  30

Gly Tyr Gln Glu Leu His Leu Lys Ser Asn Lys Gly Asp Leu Ser Phe
        35                  40                  45

Ser Pro Trp Ile Leu Val Pro Asn Ile Gly Tyr Gly Phe Tyr Gln Tyr
50                  55                  60

Leu Pro Phe Pro Asp Gly Ala Met Ser Pro Tyr Gln Ala Ala Met His
65                  70                  75                  80

Asp Gly Ser Gly Tyr Val Met His Arg Ser Met Gln Phe Glu Asp Gly
                85                  90                  95

Ala Met Leu His Ser Asp His Arg Tyr Ile Tyr Lys Gly Asn His Ile
            100                 105                 110

Lys Gly Glu Phe Arg Leu Lys Gly Ser Gly Phe Pro Ala Asp Gly Pro
        115                 120                 125

Val Met Thr Asn Ser Leu Thr Ala Ala Asp Trp Cys Val Asp Lys Leu
    130                 135                 140

Leu Tyr Pro Asn Asp Asn Thr Ile Ile Gly Lys Phe Lys Trp Thr Tyr
145                 150                 155                 160

Thr Thr Thr Ser Gly Lys Arg Tyr Gln Ser Asp Val Gln Thr Thr Val
                165                 170                 175

Thr Phe Gly Lys Pro Ile Ala Ala Asp Ile Leu Lys Lys Gln Pro Met
            180                 185                 190

Phe Val Phe Arg Lys Val Glu Leu Lys His Thr Lys Thr Glu Leu Asn
        195                 200                 205

Phe Lys Gln Trp Gln Lys Ala Phe Gln Asp Ile Ala
    210                 215                 220
```

US 8,609,393 B2

FLUORESCENT PROTEINS AND GENES ENCODING THEM

CROSS REFERENCE TO RELATED APPLICATIONS

This application claims benefit under 35 U.S.C. 119(e) of U.S. Provisional Patent Application Ser. No. 60/811,769 filed Jun. 8, 2006, the whole of which is incorporated herein by reference.

The present invention relates to a class of new fluorescent proteins and genes encoding them. The invention is particularly concerned with fluorescent proteins from Cephalochordata or amphioxus or lancelet and structural genes encoding such proteins.

BACKGROUND

Fluorescent proteins (FPs), in particular green fluorescent proteins, are commonly used fluorescent makers in molecular biology to monitor gene expression and protein localization in living organisms and in medical diagnostic applications.

Fluorescent proteins are found in a variety of marine organisms ranging from the jellyfish *Aequorea victoria*, to the Indo-Pacific coral *Discosoma*. Due to their genetically encoded fluorescence, fluorescent proteins have become most important marker molecules and tools in cell biology. Becoming spontaneously fluorescent without any requirements for cofactors, substrates or other gene products, FPs have revolutionized research in many areas of biology.

During recent years FPs have also gathered strong appreciation as powerful tools for the drug discovery process. As fluorescent probes, FPs enable both real-time and non-invasive reporting in living cells. This ability provides a basis for cell-based monitoring of FP-linked targets upon administration of external drugs. The impact of FPs has been revolutionary; FPs have not only facilitated visualization of intricate cellular architecture but they have also acted as markers of protein dynamics and behavior in cell biology. These applications have been translated to drug discovery where fluorescence proteins have been utilized in fluorescence and confocal imaging, HTS/HCS screening assays and for in vivo diagnostics. FPs cannot only be used in early stage target characterization but also in retrieving non-invasive 'whole organism' data and in evaluating lead compound toxicology.

Limitations of most fluorescent proteins are generally associated with molecular brightness and/or stability. Moreover, many FPs have additional complications involving protein folding, chromophore maturation and self-association. Although FPs have vastly improved over the years, mainly by introducing mutations, they still exhibit major limitations.

There is an interest in obtaining new fluorescent proteins with different properties compared to known fluorescent proteins. For instance, there are no fluorescent proteins on the market that can be used in paraffin sections at room temperature for immunohistochemical purposes since they lose their fluorescence intensity under such conditions.

DESCRIPTION OF THE INVENTION

The present invention provides a class of new fluorescent proteins with different properties compared to known proteins, e.g. they can be used in paraffin sections at room temperature for immunohistochemical purposes since they retain their fluorescence intensity under such conditions.

One aspect of the invention is directed to an isolated and purified structural gene encoding a fluorescent protein from a Cephalochordata, or encoding a mutant or recombinant protein that has at least 80% amino acid sequence identity with the fluorescent protein, and comprising the internal amino acid sequence

```
                                          (SEQ ID NO: 47)
    Gly Tyr Xaa Xaa Xaa Gln Tyr Leu Pro Xaa Pro
    1               5                   10
``` wherein
Xaa in position 3 is Ala or Gly,
Xaa in position 4 is Phe, His or Tyr,
Xaa in position 5 is His, Tyr or Asn, or
Xaa in position 10 is Phe or Tyr.

The term "structural gene" means the protein coding nucleotide sequence of a gene or polynucleotide.

The internal sequence SEQ ID NO:47 is found in all hitherto analyzed proteins of the new class of fluorescent proteins expressed by Cephalochordata, but some amino acid substitution, extension and/or deletion in this sequence may be possible, especially in the positions where there are variations in the amino acids, i.e. where the amino acid is Xaa.

A mutant or recombinant protein that has at least 80% amino acid sequence identity with a fluorescent protein defined in this invention may be truncated and/or have amino acid substitutions, insertions and/or deletions and have any percentage of amino acid identity with regard to the fluorescent protein defined in this invention between 80% and 99.9%, such as at least 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identity.

The Cephalochordata is also named amphioxus or lancelet and is herein exemplified by the species a) *Branchiostoma floridae* and b) *Branchiostoma lanceolatum*.

In an embodiment of the invention the structural gene is selected from the group consisting of SEQ ID NOs: 1-23.

In another embodiment of the invention the structural gene is selected from the group consisting of SEQ ID NOs: 48-67.

In still another embodiment of the invention the structural gene is selected from the group consisting of SEQ ID NOs: 88-90.

The nucleotide sequences SEQ ID NOs: 88-90 are examples of isolated and purified structural genes encoding mutant proteins of the invention. The exemplified mutant sequences have the sequence of the wild-type *Branchiostoma lanceolatum* nucleotide sequence SEQ ID NO: 59 from position 7 including position 666, and some point mutations. The nucleotide A in positions 356 and 357 of the mutant sequences SEQ ID NO: 88-90, respectively, has been inserted instead of the nucleotide C in the wild-type sequence, and further the nucleotide C in position 524 of the mutant sequences SEQ ID NOs: 89 and 90, respectively, has been inserted instead of the nucleotide A in the wild-type sequence. In addition, the mutant sequence SEQ ID NO: 90 has in position 469 the nucleotide A instead of G in the wild-type sequence and in position 471 the nucleotide G instead of C in the wild-type sequence.

Another aspect of the invention is directed to a vector comprising a structural gene according to the invention, such as a structural gene selected from the group consisting of SEQ ID NOs: 1-23, SEQ ID NOs: 48-67 and SEQ ID NOs: 88-90. The vector may be any vector which can comprise a structural gene of the invention and necessary flanking regions with regulatory elements necessary for expression of the desired fluorescent protein of the invention or a fusion protein comprising such a protein according to the invention. The regulatory elements necessary for expression are e.g. a suitable operon or promoter that is natural or foreign to the host selected for expression of the protein. Suitable vectors useful in the present invention are e.g. plasmids, cosmids and virus expression vectors.

Yet another aspect of the invention is directed to a host cell comprising a vector according to the invention or comprising a transgene including a structural gene according to the invention. The transgene should be operably inserted into the genome of the host to express the desired fluorescent protein of the invention or a fusion protein comprising such a protein according to the invention. Suitable host cells are both prokaryotic cells such as *Escherichia coli* cells, and eukaryotic cells such as mammalian, insect, yeast, and plant cells.

A further aspect of the invention is directed to a fluorescent protein comprising the internal amino acid sequence

```
                                              (SEQ ID NO: 47)
   Gly Tyr Xaa Xaa Xaa Gln Tyr Leu Pro Xaa Pro
   1           5                   10
``` wherein
Xaa in position 3 is Ala or Gly,
Xaa in position 4 is Phe, His or Tyr,
Xaa in position 5 is His, Tyr or Asn, or
Xaa in position 10 is Phe or Tyr.

The internal sequence SEQ ID NO:47 may possibly have some amino acid substitution, extension and/or deletion in this sequence, especially in the positions where there are variations in the amino acids, i.e. where the amino acid is Xaa.

In an embodiment of this aspect of the invention the protein of the invention is an isolated or recombinant fluorescent protein from a Cephalochordata, such as from the species a) *Branchiostoma floridae* or b) *Branchiostoma lanceolatum*, or an isolated mutant or recombinant protein that has at least 80% amino acid sequence identity with the fluorescent protein, and has the internal amino acid sequence

```
                                              (SEQ ID NO: 47)
   Gly Tyr Xaa Xaa Xaa Gln Tyr Leu Pro Xaa Pro
   1           5                   10
``` wherein
Xaa in position 3 is Ala or Gly,
Xaa in position 4 is Phe, His or Tyr,
Xaa in position 5 is His, Tyr or Asn, or
Xaa in position 10 is Phe or Tyr.

In analyzed wild-type proteins according to the invention, the C-terminal Pro in SEQ ID NO: 47 is followed by Asp Gly, Ala Gly, Asp Asp or Gly Gly.

A mutant or recombinant protein that has at least 80% amino acid sequence identity with a fluorescent protein defined in this invention may be truncated and/or have amino acid substitutions, insertions and/or deletions and have any percentage of amino acid identity with regard to the fluorescent protein defined in this invention between 80% and 99.9%, such as at least 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identity.

In an embodiment of the invention the fluorescent protein is a protein that has an amino acid sequence selected from the group consisting of SEQ ID NOs: 24-46.

In another embodiment of the invention the fluorescent protein is a protein that has an amino acid sequence selected from the group consisting of SEQ ID NOs: 67-87.

In still another embodiment of the invention the fluorescent protein has an amino acid sequence selected from the group consisting of SEQ ID NOs: 91-93.

The amino acid sequences SEQ ID NOs: 91-93 are examples of mutant proteins of the invention that have the amino acid sequence SEQ ID NO: 79 of the wild-type *Branchiostoma lanceolatum* and some point mutations. In the amino acid sequences SEQ ID NOs: 91-93, the Thr of the wild-type protein in position 119 has been replaced by Lys, and further in the sequences SEQ ID NOs: 92 and 93, the amino acid Asn of the wild-type protein in position 175 has been replaced by Thr. Additionally, the amino acid Asp of the wild-type protein in position 157 has been replaced by Lys in the sequence SEQ ID NO: 93.

The recombinant fluorescent proteins comprised by the present invention may be in monomeric, dimeric or multimeric, such as tetrameric, form.

Use of Fluorescent Proteins According to the Invention

Due to the inherent property of FPs to spontaneously become fluorescent, and in all organisms and in all types of cells, FPs have become invaluable tools in many biological and medical disciplines. A wide range of applications of the FPs have been developed that can be classified into four areas; visualizing/monitoring of organisms, cells, proteins and molecular events. The fluorescent proteins and structural genes encoding the them according to the invention may be used in all hitherto known applications of fluorescent proteins, such as those described below.

To visualize an organism, a structural gene encoding a FP can be introduced and together with appropriate regulatory sequences become expressed as an inheritable fluorescent marker in a variety of organisms ranging from virus, bacteria and yeast to plants, fish and mice. For example, infections of viruses and bacteria can be monitored, as well as the survival and spread of genetically modified organisms, GMOs. Since the FPs according to the invention can be functionally expressed in both prokaryotic and eukaryotic cells, and they have excellent stability, brightness and photoresistance, they are expected to be excellent for such applications.

To visualize cells or organelles, a structural gene encoding a FP may be introduced as a transgene in e.g. germ line cells and in vitro cultured cells. For example, monitoring of cell fate/lineages in transgenic animals, of cancer cells in vivo, of wound healing and of neurite outgrowth can be accomplished. Additional examples are marking of organelles (mitochondria, nuclei; etc) and GFP imaging: methodology and application to investigate cellular compartmentation in plants. (See e.g. for a review *J Exp Bot.* 2001 April; 52(356): 529-39.) The properties of the FPs according to the invention enables them to be used for paraffin-imbedded and section tissues.

To visualize proteins, a structural gene encoding a FP can be fused to a gene of interest producing a fusion protein that is tagged by the FP chromophore. The fusion protein can then be monitored in e.g. living cells in real time, thus enabling analyzes of cellular localization of individual proteins (numerous examples in the prior art).

Protein-protein interactions can be followed by labeling two different proteins with two different chromophores, and their interaction can be monitored by FRET (Fluorescence resonance energy transfer) or BRET (Bioluminescence Resonance Energy Transfer) in case of a bioluminescent donor to a fluorescent acceptor protein.

In drug screening protein-drug interactions are studied. Co-localization of fluorescent fusion proteins with intracellular localization markers are used as indicators of movements of intracellular fluorescent fusion proteins/peptides. The aggregation or internalization of fluorescent-tagged plasma membrane proteins (e.g. G-protein coupled receptors) can be used as drug screening assays.

In the literature there are numerous references to the use of FPs and genes encoding them as sensors for different purposes, such as sensors for protease activity: Detection of MMP activity in living cells by a genetically encoded surface-displayed FRET sensor. *Biochim Biophys Acta* 2007 March; 1773(3):400-7, *Epub* 2006 Nov. 11, and Development and application of a GFP-FRET intracellular caspase assay for drug screening. *J Biomol Screen.* 2000 October; 5(5):307-18; as sensors for atoms or ions: Genetic oxygen sensor: GFP as an indicator of intracellular oxygenation *Adv Exp Med. Biol.* 2005; 566:39-44, Elimination of environmental sensitivity in a cameleon FRET-based calcium sensor via replacement of the acceptor with Venus. *Cell Calcium.* 2005 April; 37(4):341-8, Construction of a whole-cell gene reporter for the fluorescent bioassay of nitrate. *Anal Biochem.* 2004 May 1; 328(1):60-6, and Transgenic mice expressing a pH and Cl-sensing yellow-fluorescent protein under the control of a potassium channel promoter. *Eur J. Neurosci.* 2002 January; 15(1):40-50; as sensors for organic molecules: A new green fluorescent protein-based bacterial biosensor for analyzing phenanthrene fluxes. *Environ Microbiol.* 2006 April; 8(4):697-708, and Live imaging of glucose homeostasis in nuclei of COS-7 cells. *J. Fluoresc.* 2004 September; 14(5):603-9; as sensors for electrical activity or neural cell activation: A hybrid approach to measuring electrical activity in genetically specified neurons". *Nat. Neurosci.* 2005 November; 8(11):1619-26. *Epub* 2005 October, and A genetically encoded optical probe of membrane voltage. *Neuron.* 1997 October; 19(4):735-41: as sensors for cell cycle: Characterization and gene expression profiling of a stable cell line expressing a cell cycle GFP sensor. *Cell Cycle.* 2005 January; 4(1):191-5. *Epub* 2005 Jan. 29; as sensors for promoters or gene activation; A high-throughput approach to promoter study using green fluorescent protein. *Biotechnol Prog.* 2004 November-December; 20(6):1634-40; and as sensors for apoptosis: Degradation of GFP-labelled POM121, a non-invasive sensor of nuclear apoptosis, precedes clustering of nuclear pores and externalization of phosphatidylserine. *Apoptosis.* 2004 May; 9(3):363-8.

The invention will now be illustrated by description of drawings and of embodiments and experiments of the invention, but it should be understood that the scope of for the invention is not limited to any described details.

SHORT DESCRIPTION OF THE DRAWINGS

FIG. 1 is a diagram that shows emission spectra after excitation at 500-520 nm of four FPs of the invention, namely Green Y-1=SEQ ID NO: 68; Yellow O-1=SEQ ID NO: 74; Orange O-2=SEQ ID NO: 75 and Red R-5=SEQ ID NO: 79.

DESCRIPTION OF EMBODIMENTS AND EXPERIMENTS OF THE INVENTION

Natural Occurrence of Fluorescent Proteins of the Invention

Proteins comprised by the definition of fluorescent proteins according to the invention occur naturally in the Cephalochordata (amphioxus) e.g. *Branchiostoma floridae* or *Branchiostoma lanceolatum*. They are expressed in supportive cells in the anteriormost of the body, e.g., cells in the coelom walls, the subepidermal canals, the oral cirri skeleton, and the oral cirri tufts. However, the number of different positive cell types varies between different individuals.

The proteins are found as either only a single fluorescent protein, or as a mixture of different fluorescent proteins.

All properties have been examined at room temperature unless otherwise stated.

Characteristics of the Fluorescent Proteins of the Invention

The fluorescence characteristics of selected FPs have been determined by confocal laser scanning microscopy on bacterial colonies with samples in 96-well plates and on proteins purified after expression in *E. coli*. Brightness was calculated as the product of quantum yield and molar extinction coefficient—determined by comparing the Coomassie Brilliant Blue staining intensity, after SDS-PAGE, of known amounts of EGFP (Enhanced Green Fluorescence Protein) with the new FPs. Purified EGFP has been employed as reference fluorescent protein.

Optical Properties of Fluorescent Proteins of the Invention

The purified proteins are yellow to orange in solution, and yellow to red in solid state.

The absorption maxima for the purified native proteins are at 210 nm (peptide bonds), 260 nm (aromatic amino acid residues), and 484-490 nm (fluorophore). Upon denaturation, the peak at 260 nm is shifted to 280 nm, and the fluorophore peak is almost completely lost.

The emission spectrum of fluorescent cells in situ and of purified proteins consists of peaks at 485, 500, 515, 530, 545, 560, 575, 590, 610 and 635 nm. The number of peaks varies between individuals and between different cell types in the same individual. The absorption maxima for each individual protein might be slightly shifted from these values due to overlaying of neighbouring peaks.

Excitation at 458 nm results in peaks at 485 and 500 nm (primary excitation), and 545-635 nm (presumably fluorescence resonance energy transfer, FRET) Excitation at 476 or 486 nm results in peaks at 515 and 530 nm (primary excitation), and 545-635 nm (presumably FRET). Excitation at 514 nm results in peaks at 545-635 nm (primary excitation).

Figure 1:
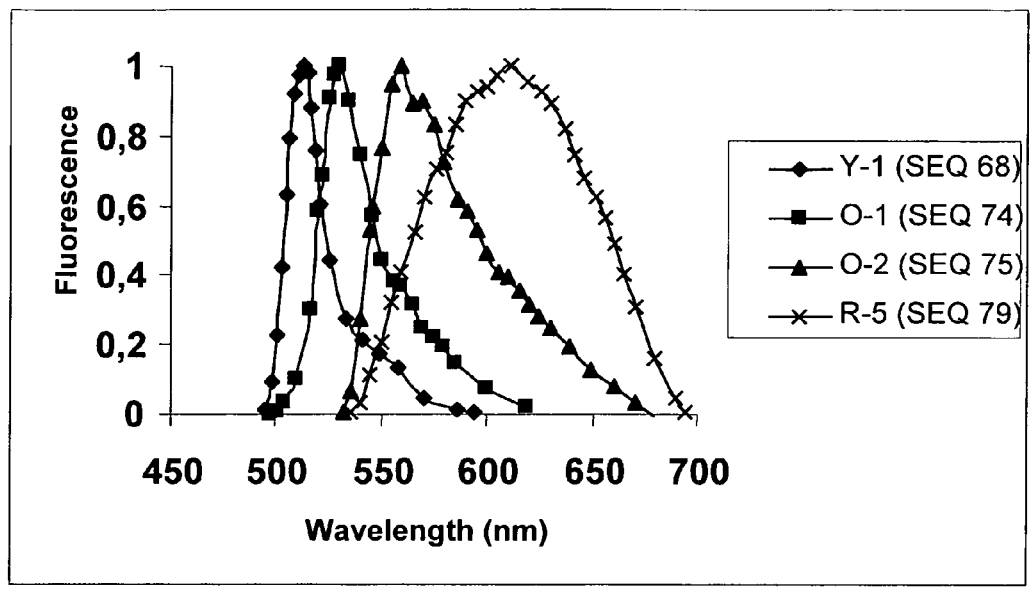

The excitation spectra of all analyzed new FPs are very similar with maxima around 510-520 nm, in accordance with the identity of the chromophore forming residues, but in spite of this similarity the emission spectra differ considerable as shown in FIG. 1. This property thus suggests a new mechanism for generation of colour diversity as compared to other known fluorescent proteins.

Resistance to Bleaching

Figure 2:
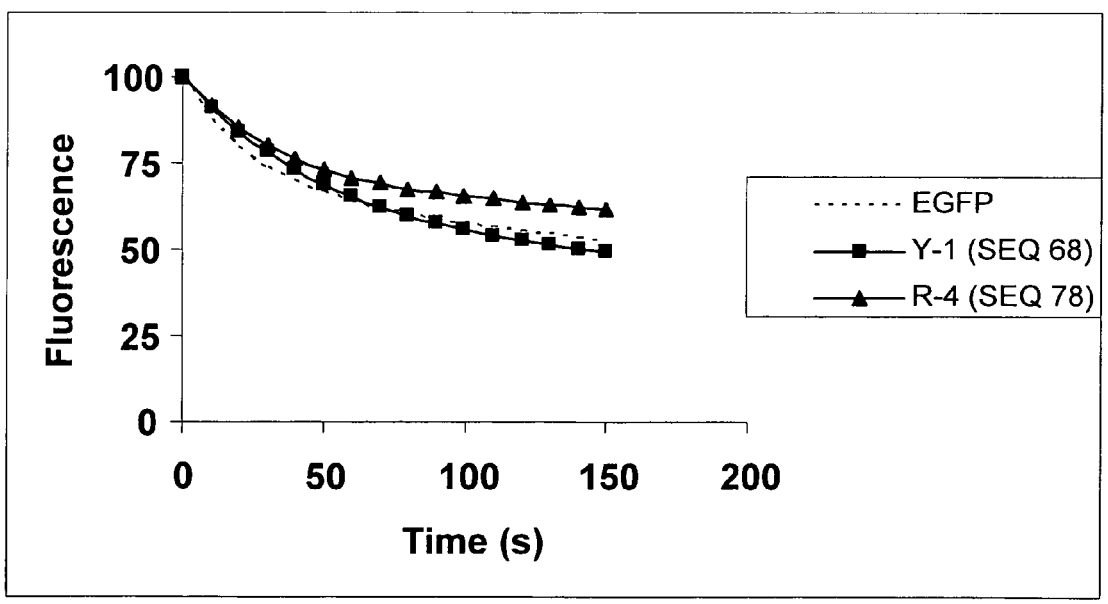
FIG. 2 is a diagram that shows the fluorescence plotted against time for the reference EGFP and two FPs of the invention, Green FP Y-1=SEQ ID NO: 68; Red FP R-4=SEQ ID NO: 78, indicating that the FPs are resistant to photobleaching.

The fluorescence has similar bleaching resistance in strong light as the most resistant fluorescent protein (EGFP (Enhanced Green Fluorescence Protein) and Emerald). The photostability, i.e. resistance to bleaching, was determined on proteins in solutions (Tris-HCl, pH 7.5) that were placed between a cover slip and a microscope slide and exposed to the highest possible light intensity in a fluorescent microscope (mercury lamp, 100× oil immersion). As shown in FIG. 2, the new FPs are very resistant to bleaching and display an even greater photostability than EGFP.

Maturation and Stoke's Shift

As other red fluorescent proteins, the new red variants go through a maturation stage before reaching the mature form that emits red light. In contrast to many other wild-type red FPs the maturation step is quite fast as red fluorescence can be observed in growing $E.\ coli$ colonies.

Another interesting feature of the red variants is the very large difference between absorption and emission max, the Stoke's shift is more than 100 nm.

Insensitivity to Environmental Effects

The fluorescence is pH dependent. Fluorescence occurs in weakly acidic, neutral and basic solutions but not in acidic and strongly basic solutions. The green fluorescence has a maximum at pH 10, at least 50% fluorescence between pKa1 and pKa2 (limits for >50% of maximal fluorescence; pKa1=7.7, and pKa2=11.6), and has almost a linear dependence of pH between pH 6-9.

Figure 3:
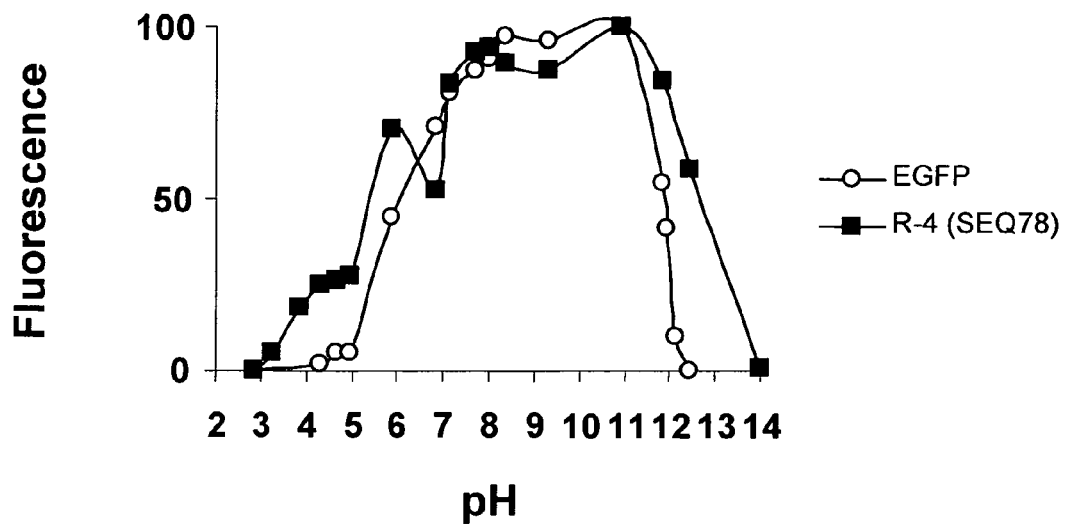
FIG. 3 is a diagram that shows the fluorescence plotted against pH for the reference EGFP and a red FP, R-4=SEQ ID NO: 78, of the invention, indicating that R-4 is insensitive to pH.

The new FPs are extremely stable and insensitive to environmental effects. The pH sensitivity has been analyzed with a red variant (R-4=SEQ ID NO: 78) and as shown in FIG. 3, the fluorescence of R-4 is maintained over a wider pH range than the fluorescence of EGFP.

Physical Properties of Fluorescent Proteins of the Invention

The apparent molecular weight of a native, proteinase K-treated protein is about 25 kDa (gel filtration) and of denaturated protein is about 30-35 kDa (SDS-PAGE). The green fluorescent proteins are slightly larger than the red ones. The protein oligomerizes and predominantly forms tetramers. However, trimers and pentamers, hexamers, dimers and octamers, and polymers are also present (in decreasing order of frequency).

Chemical Properties of Fluorescent Proteins of the Invention

The proteins are soluble in water, phosphate buffer and Tris buffer but not in acetone, ethanol, glycerol or xylene. The proteins can be precipitated with acetone or ethanol but not with ammonium sulfate (80% of saturated solution).

The fluorescence is lost upon denaturation.

The fluorescence resists proteinase K (0.1-1 mg/ml at 45° C. overnight), detergents (10% sodium dodecyl sulfate, and 0.1% triton X-100), aldehyde fixation (formaldehyde, and glutaraldehyde), chelates (1 M EDTA), many organic solvents (acetone, ethanol, glycerol, melted paraffin, and xylene), high salinity (80% saturated ammonium sulfate, 4 M sodium chloride, and saturated disodium hydrogen phosphate), low salinity (distilled water), heavy metal ions (copper chloride, lead nitrate, and silver nitrate), weak oxidizing agents (hydrogen peroxide, oxygen in air, potassium chromate in neutral solution, potassium dichromate in neutral solution, potassium ferricyanide, silver nitrate, and sodium chlorate in neutral solution), weak reducing agents (10 mM dithiothreitol, and pyrogallol in neutral solution), and moderately high temperatures (45° C. for 12 h, 65° C. for 1 h).

The fluorescence is destroyed by some organic solvents e.g. (benzyl alcohol-benzyl benzoate mixture, strong oxidizing agents (iodine, periodic acid potassium chromate in acid solution, potassium dichromate in acid solution, potassium permanganate, sodium chlorate in alkaline solution, and sodium hypochlorite in alkaline solution), strong reducing agents (pyrogallol in alkaline solution), and very high temperature (98° C.).

Stability of the Fluorescent Proteins

Figure 4:
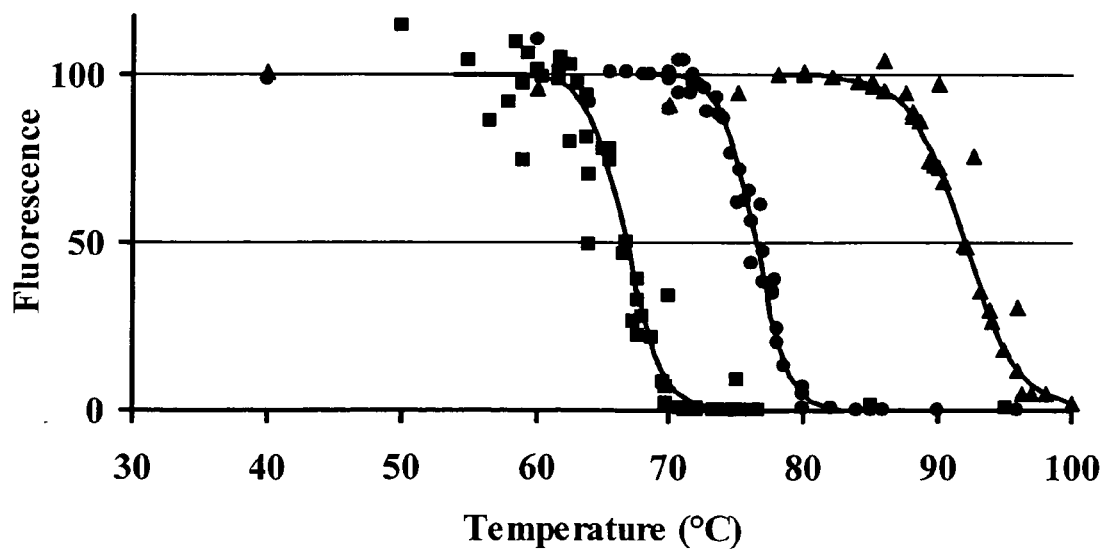
FIG. 4 is a diagram that shows the fluorescence plotted against temperature for the reference EGFP (squares) and Red FP (triangles), R-1=SEQ ID NO: 76, and Green FP (circles), Y-3=SEQ ID NO: 70, of the invention. The fluorescence was recorded after 1 h (and 1 min for EGFP) after incubation at the indicated temperature.
Figure 5:
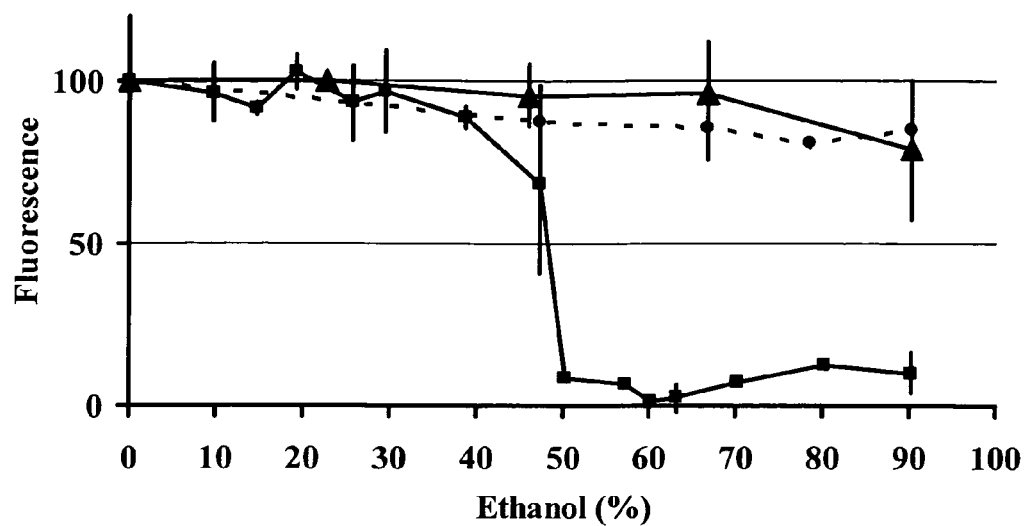
FIG. 5 is a diagram that shows the fluorescence plotted against concentration of ethanol for the reference EGFP (squares) and Red FP (triangles), R-1=SEQ ID NO: 76, and Green FP (circles), Y-3=SEQ ID NO: 70, of the invention. The fluorescence was recorded after 1 h after incubation at the indicated concentration of ethanol.

The stability of the FPs has been analyzed both in situ and using purified proteins after expression in $E.\ coli$. As shown in FIGS. 4 and 5, two of the recombinantly expressed proteins of the invention, Red FP (R-1=SEQ ID NO: 76) and Green FP (Y-3=SEQ ID NO: 70), are very thermostable and withstand high concentrations of ethanol. The new FPs are also stable in e.g. 6 M guanidine hydrochloride, and withstand many organic solvents making them useful in histochemical applications including those using paraffin imbedded and sectioned tissues.

Bright Red FPs

The brightness (product of quantum yield and molar extinction coefficient) has been calculated for two of the new red variants, and they are clearly among the brightest red wild-type proteins ever found. The Table below summarizes the fluorescence characteristics of selected members of the FPs of the invention.

TABLE

Fluorescence characteristics of selected FPs or the invention and a selection of reference proteins (from Ref. 1).

| Class | Protein | Excitation max (nm) | Emission max (nm) | Brightness | Photostability |
|---|---|---|---|---|---|
| Far-red | mPlum | 590 | 649 | 4.1 | 53 |
| Red | mCherry | 587 | 610 | 16 | 96 |
| | mStrawberry | 574 | 596 | 26 | 15 |
| | DsRed-mono | 556 | 586 | 3.5 | 16 |
| | R-4 | 520 | 615 | 20 | ND |
| | R-5 | 520 | 620 | 20 | 180 |
| Orange | mOrange | 548 | 562 | 49 | 9 |
| | mKO | 548 | 559 | 31 | 122 |
| | O-1 | 530 | 545 | ND | ND |
| | O-2 | 530 | 560 | ND | ND |
| Yellow green | Venus | 515 | 528 | 53 | 15 |
| | EYFP | 514 | 527 | 51 | 60 |
| | Y-1 | 518 | 530 | ND | 180 |
| | Y-3 | 518 | 530 | ND | ND |
| Green | EGFP | 489 | 507 | 34 | 174 |

ND: not determined
R-4 = SEQ ID NO: 78; R-5 = SEQ ID NO: 79; O-1 = SEQ ID NO: 74; O-2 = SEQ ID NO: 75; Y-1 = SEQ ID NO: 68; Y-3 = SEQ ID NO: 70.
Ref. 1 = Shaner, N. C. et al. A guide to choosing fluorescent proteins. Nature Methods 2 (12) 905-909, 2005.

Isolating Fluorescent Proteins from Cephalochordata

Several hundred specimens of lancelet, i.e. Cephalochordata, also named amphioxus, are collected. In this example *Branchiostoma lanceolatum* were collected. Their heads were cut off and mixed with an equal volume of a neutral buffer solution (e.g., 10 mM Tris, pH 7.5, 10 mM NaCl). The mixture was digested with proteinase K (final concentration of 0.1 mg/ml) at 40° C. over-night followed by centrifugation for 10 min at 16 000 rpm to remove any remaining debris. The supernatant was loaded on a Sephadex G-200 column (30-100 cm; equilibrated with the same buffer as used during the digestion) and gel filtrated. Fluorescent fractions were collected, pooled, and precipitated by addition of 1.8 volumes of acetone and centrifugation for 1 min at 16000 rpm. The supernatant was discharged. The pellet was washed with 65% acetone, briefly dried (allowing remaining acetone to evaporate), dissolved in water, denatured with sodium dodecyl sulfate (SDS; final concentration of 1%) and dithiothreitol (DTT; final concentration 100 mM) at 95° C. for 3 min, and loaded on a 2.5% SDS-PAGE gel. After the completed gel electrophoresis and Coomassie staining, the two bands at around 30 kDalton were cut out, eluted, and digested into fragments with trypsin. The fragments are analyzed with tandem mass spectrometry using MALDI-TOF (matrix assisted laser desorption-time of flight) to obtain their amino acid sequence. Degenerated oligonucleotide primers are designed from these amino acid sequences. These primers are used for 5'-RACE PCR (rapid amplification of cDNA ends polymerase chain reaction) on cDNA that is prepared from purified mRNA from lancelet heads. The PCR products are size separated by agarose electrophoresis. The different bands are cut out, purified, cloned, and sequenced. Oligonucleotide primers are designed from the obtained sequences and used for 3'RACE PCR on the same cDNA to obtain the complete coding region. The PCR products are cloned into an expression vector, and fluorescent transformants are selected and sequenced. All steps are performed at room-temperature unless otherwise stated.

Isolating Fluorescent Proteins from Genome Project

The known amino acid sequence of green fluorescent proteins (GFP) from copepods (obtained from GenBank) are used for searches through the unassembled trace files obtained from genomic sequencing of Florida lancelet (*Branchiostoma floridae*) (available at http://www.ensembl.org/). Nucleotide sequences containing putative GFP-like exons were selected. These sequences were elongated by successive searches with the sequences for new matching sequences and alignments of these new sequences to these already found. This is repeated for many cycles until either complete genes were obtained, or no more new sequences are found. The assembled genes are analyzed by a splicing prediction software [NetGene2 software (http://www.cbs.dtu.dk/services/NetGene2/)] and putative exons are converted into amino acid sequences. The obtained nucleotide sequences are analyzed for conserved regions. Degenerated oligonucleotide primers are designed for two different conserved regions (located in exon 3 and exon 6). These primers are used for nested 5'-RACE PCR on cDNA that is prepared from purified mRNA from lancelet heads. The PCR products are size separated by agarose electrophoresis. The different bands are cut out, purified, cloned, and sequenced. Oligonucleotide primers are designed from the obtained sequences and used for 3'RACE PCR on the same cDNA to obtain the complete coding region. The PCR products are cloned into an expression vector, and fluorescent transformants are selected and sequenced.

Cloning and Sequencing

RNA was prepared and through RT-PCR, using degenerate PCR-primers, and 5'- and 3'-RACE, full-length cDNA clones could subsequently be obtained by fluorescence screening of *E. coli* colonies. The obtained full-length clones represent yellow/green, orange and red FPs. No blue or pure green FPs were among the full-length clones, but a number of incomplete clones were sequenced that may represent these colours.

In total some 40 unique sequences encoding novel fluorescent proteins have been obtained so far. The individual proteins are structurally closely related and although distinct from other known fluorescent proteins they clearly belong to the same superfamily.

Mutant Proteins a. Aggregation State

Figure 6:
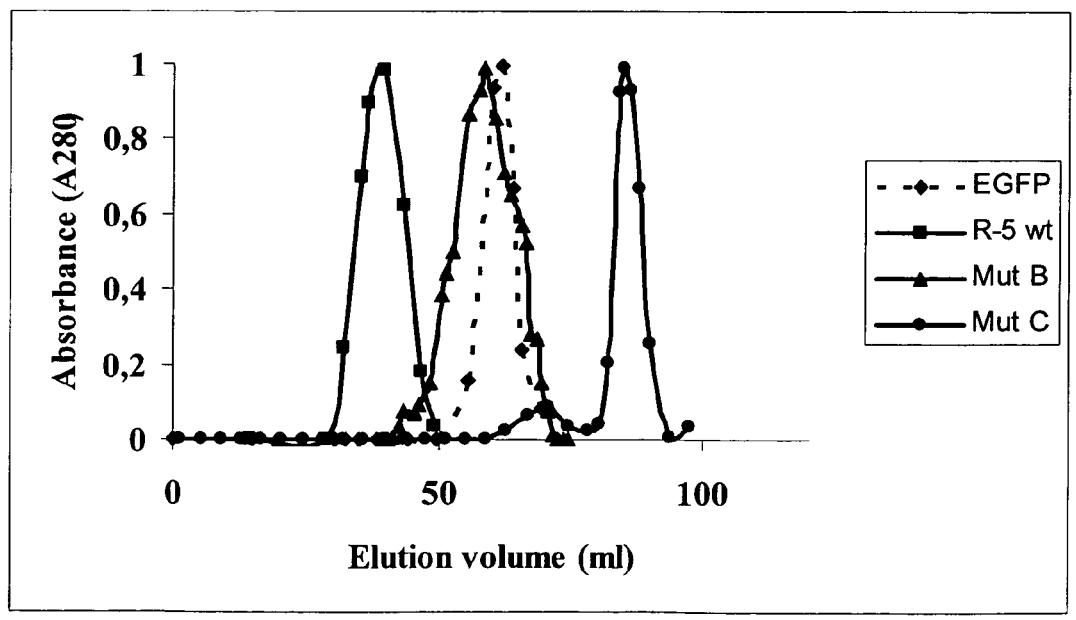
FIG. 6 is a diagram that shows absorbance plotted against elution volume in size exclusion chromatography of the wild-type FP wt R-5 (SEQ ID NO: 79), the double mutant Mut B (SEQ ID NO: 92) and the triple mutant Mut C (SEQ ID NO: 93) as well as EGFP.

The wild-type fluorescent proteins have a tendency to self-aggregate and form tetramers. Among the limited number of new FPs that we so far have analyzed, no monomeric variant has been observed, but the tendency to self-aggregate appears to vary among individual variants. In order to generate a pure monomeric variant, which would be advantageous for certain applications, the protein R-5 (SEQ ID NO: 79) was subjected to limited mutagenesis after extensive 3-D modelling. Three amino acid residues were chosen as suitable candidates for mutagenesis, and three mutants with single, double and triple mutations were constructed and custom made by an external laboratory. After expression in *E. coli* and purification their aggregation state were analyzed by gel-chromatography on a HiPrep Sephacryl S-200 column. The conditions used (i.e. high protein concentrations) were chosen to promote aggregation, and EGFP, which is a weak forming dimer, did elute as a peak with an apparent molecular weight of ~60 kDa, i.e. as a dimer. As shown in FIG. 6, the double mutant of R-5 (Mut B), SEQ ID NO: 92, also eluted as a dimer whereas the triple mutant (Mut C), SEQ ID NO: 93, eluted with an apparent molecular weight of ~30 kDa, i.e. as a monomer.

b. Characteristics of Mutant Fluorescent Proteins

Figure 7:
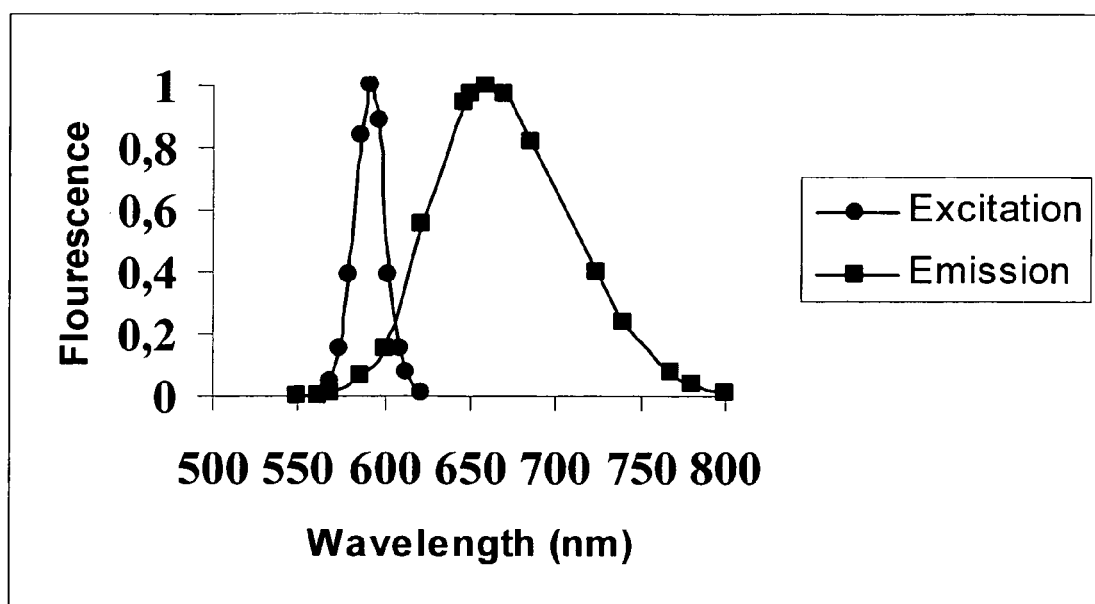
FIG. 7 is a diagram that shows normalized fluorescence plotted against wavelength in excitation and emission spectra of mutant R-5C, SEQ ID NO: 93. The emission spectra were recorded after excitation at 590 nm.

The dimeric mutant (Mut B), SEQ ID NO: 92, has a diminished tendency to self-aggregate, but folds less efficiently than the wild-type protein. The optical properties appear to be the same as the wild-type R-5 (SEQ ID NO: 79) protein. Neither excitation-emission spectra, nor brightness or stability appear different from the wild-type protein. However, the monomeric mutant (Mut C), SEQ ID NO: 93, has lost much of the brightness of the wild-type protein, and—probably due to a maturation defect—has its major emission peak shifted to the orange part of the spectra. Interestingly, the mutants, including the monomeric variant, have also a new emission peak with a maximum at ~660 nm with excitation at 590 nm. The emission peak is quite wide and although the overall intensity is low, there is a clear emission up to 750 nm, thus extending into the infrared part of the spectra (FIG. 7), which is a clear benefit for in vivo applications.

The invention claimed is:

1. A vector comprising a structural gene encoding a fluorescent protein, wherein said structural gene comprises the sequence of SEQ ID NO: 50.

2. A host cell comprising the vector of claim 1.

3. A host cell comprising a transgene, wherein said transgene comprises the sequence of SEQ ID NO: 50.

* * * * *